US007910691B2

(12) United States Patent
Zavada et al.

(10) Patent No.: US 7,910,691 B2
(45) Date of Patent: *Mar. 22, 2011

(54) MN GENE AND PROTEIN

(75) Inventors: Jan Zavada, Prague (CZ); Silvia Pastorekova, Bratislava (SK); Jaromir Pastorek, Bratislava (SK)

(73) Assignee: Institute of Virology of the Slovak Academy of Sciences, Bratislava (SK)

( * ) Notice: Subject to any disclaimer, the term of this patent is extended or adjusted under 35 U.S.C. 154(b) by 448 days.
This patent is subject to a terminal disclaimer.

(21) Appl. No.: 11/929,351

(22) Filed: Oct. 30, 2007

(65) Prior Publication Data
US 2008/0193951 A1  Aug. 14, 2008

Related U.S. Application Data

(63) Continuation of application No. 09/807,949, filed as application No. PCT/US99/24879 on Oct. 22, 1999, now Pat. No. 7,713,704.

(51) Int. Cl.
*C07K 5/00* (2006.01)

(52) U.S. Cl. .................................... 530/300; 530/328

(58) Field of Classification Search .................. 530/300, 530/328
See application file for complete search history.

(56) References Cited

U.S. PATENT DOCUMENTS

| 5,387,676 A | 2/1995 | Zavada et al. ................. 536/23.5 |
| 5,585,479 A | 12/1996 | Hoke et al. .................... 536/24.5 |

FOREIGN PATENT DOCUMENTS

| WO | 8808854 | 11/1988 |
| WO | 9318152 | 9/1993 |
| WO | 9534650 | 12/1995 |

OTHER PUBLICATIONS

Zavada et al. (Br. J. Cancer. Jun. 2000; 82 (11): 1808-1813).*
Anton et al., "Localized renal-cell carcinoma: detection of abnormal cells in peritumoral tissue. A cytophotometry and immunocytochemistry study," *World J. Urol.*, 13(3): 149-152 (1995).
Bander et al., "Renal cancer imaging with monoclonal antibody G250," *J. Urol.*, 155 (5 Suppl.): 583A (Abstract 1088) (1996).
Brewer et al., "A Study of Biomarkers in Cervical Carcinoma and Clinical Correlation of the Novel Biomarker MN," *Gynecologic Onocology*, 63: 337-344 (1996).
Cho et al., "Hypomethylation of MN/CA9 promoter region contributes to its expression in human renal cell carcinomas," Abstract 2922, *Proceedings of the American Association for Cancer Research*, Apr. 10-14, 1999, Philadelphia, PA, vol. 40 (Mar. 1999).
Costa et al., "MN Protein Immunolocalization in Uterine Cervix Carcinoma With Glandular Differentiation—A Clinicopathologic Study of a New Cancer-specific Biomarker," *International Journal of Surgical Pathology*, 3(2): 73-82 (1995).
Costa, M., "MN and Ki67 (MIB-1) in Uterine Cervix Carcinoma: Novel Biomarkers With Divergent Utility," *Human Pathology*, 27(3): 217-219 (Mar. 1996).
Cote, "Protein Antigen Helps Identify Early Cervical Abnormalities," *Women's Health Weekly*: News Section, p. 7 (Mar. 30, 1998).

Divgi et al., "Scintigraphy of Renal Cell Carcinoma with I-131 Labelled Monoclonal Antibody (MAB) G250," *European Journal of Nuclear Medicine*, 19(8): 578 (Abstract 121-3) (Aug. 23, 1992).
Divgi et al., "Radioimmunotherapy (RIT) with I-131 Monoclonal Antibody (Mab) G250 in Metastatic Renal Cancer," *Proceedings of the 41st Annual Meeting*, 35(5): 101P (Abstract #401) (May 1994).
Divgi et al., "Radioimmunotherapy with I-131-G250 in Metastatic Renal Cell Cancer (RCC)," *J. Nucl. Med.*, 36 (5 Suppl.): 913P (Abstract 956; May 1995).
Frohman et al., "Rapid production of full-length cDNAs from rare transcripts: Amplification using a single gene-specific oligonucleotide primer," *PNAS* (USA), 85: 8998-9002 (Dec. 1988).
Frosch et al., "Cloning and characterisation of an immunodominant major surface antigen of *Echinococcus multilocularis*," *Molecular and Biochemical Parasitology*, 48: 121-130 (1991).
Ivanov et al., "Down-regulation of transmembrane carbonic anhydrases in renal cell carcinoma cell lines by wild-type von Hippel-Lindau transgenes," *PNAS* (USA) 95: 12956-12601 (Oct. 1998).
Ivanov et al., "Activation of transmembrane carbonic anhydrases in cancer development," Abstract 4549, *Proceedings of the American Association for Cancer Research*, Apr. 10-14, 1999, Philadelphia, PA, vol. 40 (Mar. 1999).
Karttunen et al., "Colorectal Tumors Show Abnormal Expression of MN/CA IX," *Pathology Research and Practice 193/5-6*: 392 Abstract No. P198 (Abstract from European Congress on Pathology at Maastricht; Aug. 31-Sep. 4, 1997).
Kranenborg et al., "Development and Characterization of Anti-Renal Cell Carcinoma X Antichelate Bispecific Monoclonal Antibodies for Two-Phase Targeting of Renal Cell Carcinoma," *Cancer Res.*, 55 (23 Suppl.) 5864s-5867s (1995).
Kurth et al., "Characterization of Human Renal Cell Carcinoma Tumor Lines by Means of Monoclonal Antibodies," *Prostate*, 6(4): 451 (Abstract) (1985).
Liao et al., "Identification of the MN Antigen as a Diagnostic Biomarker of Cervical Intraepithelial Squamous and Glandular Neoplasia and Cervical Carcinomas," *American Journal of Pathology*, 145(3): 598-609 (Sep. 1994).

(Continued)

*Primary Examiner* — Stephen L Rawlings
(74) *Attorney, Agent, or Firm* — Leona L. Lauder; Joan C. Harland; Barbara A. Shimei

(57) ABSTRACT

Identified herein is the location of the MN protein binding site, and MN proteins/polypeptides that compete for attachment to vertebrate cells with immobilized MN protein. Such MN proteins/polypeptides prevent cell-cell adhesion and the formation of intercellular contacts. The MN protein binding site is a therapeutic target that can be blocked by organic or inorganic molecules, preferably organic molecules, more preferably proteins/polypeptides that specifically bind to that site. Therapeutic methods for inhibiting the growth of pre-neoplastic/neoplastic vertebrate cells that abnormally express MN protein are disclosed. Vectors are provided that encode the variable domains of MN-specific antibodies and a flexible linker polypeptide separating those domains. Further vectors are disclosed that encode a cytotoxic protein/polypeptide operatively linked to the MN gene promoter, and which vectors preferably further encode a cytokine. The MN gene promoter is characterized, and the binding site for a repressor of MN transcription is disclosed.

9 Claims, 13 Drawing Sheets

OTHER PUBLICATIONS

Liao and Stanbridge, "Expression of the MN Antigen in Cervical Papanicolaou Smears Is an Early Diagnostic Biomarker of Cervical Dysplasia," *Cancer Epidemiology, Biomarkers & Prevention*, 5: 549-557 (Jul. 1996).

Liao et al., "Identification of the MN/CA9 Protein As a Reliable Diagnostic Biomarker of Clear Cell Carcinoma of the Kidney," *Cancer Research*, 57: 2827-2831 (Jul. 15, 1997).

Liao and Stanbridge, "Expression of MN/CA9 Protein in Papanicolaou Smears Containing Atypical Glandular Cells of Undetermined Significance Is a Diagnostic Biomarker of Cervical Dysplasia and Neoplasia," *Cancer*, 88(5): 1108-1121 (2000).

Lieskovska et al., "Study of in vitro conditions modulating expression of MN/CA IX protein in human cell lines derived from cervical carcinoma," *NEOPLASMA*, 46: 17-24 (1999).

Luiten et al., "Target-Specific Activation of Mast Cells by Immunoglobulin E Reactive with a Renal Cell Carcinoma-Associated Antigen," *Laboratory Investigation*, 74(2): 467-475 (1996).

Luiten et al., "Generation of chimeric bispecific G250/anti-CD3 monoclonal antibody, a tool to combat renal cell carcinoma," *British Journal of Cancer*, 74(5): 735-744 (1996).

Luner et al., "Monoclonal Antibodies to Kidney and Tumor-associated Surface Antigens of Human Renal Cell Carcinoma," *Cancer Res.*, 46(11): 5816-5820 (1986).

McKiernan et al., "Expression of the Tumor-associated Gene *MN*: A Potential Biomarker for Human Renal Cell Carcinoma," *Cancer Research*, 57: 2362-2365 (Jun. 15, 1997).

McKiernan et al., "Molecular Detection of Clear Cell Carcinoma of the Kidney Via a Blood Test for MN/CA9 and Prostate Specific Membrane Antigen," (Abstract No. 1272) 35$^{th}$ ASCO Annual Meeting in Atlanta, GA (May 15-18, 1999).

McKiernan et al., "First kidney cancer blood test may prevent organ removal, say researchers," *Clinica*, 859: 18 (May 24, 1999).

McKiernan et al., "The Detection of Renal Carcinoma Cells in the Perpheral Blood with an Enhanced Reverse Transcriptase-Polymerase Chain Reaction Assay for MN/CA9," *Cancer*, 86(3): 492-497 (Aug. 1, 1999).

Moon et al., "A Highly Restricted Antigen for Renal Cell Carcinoma Defined by a Monoclonal Antibody," *Hybridoma*, 4(2): 163-172 (1985).

Mulders et al., "G250, A Tumor Antigen with Therapeutic Potential in Renal Cell Carcinoma (RCC)," *Journal of Urology*, 164(4): Abstract 652 (Apr. 1999).

Murakami, et al., "*MN/CA9* gene expression as a potential biomarker in renal cell carcinoma," *BJU International*, 83: 743-747 (1999).

Nakagawa et al., "MN as a Potential Target in Renal Cell Carcinoma," *J. Urology*, 159 (5 Suppl.): 187, Abstract 720 (May 1998).

Nakagawa, et al., "MN targeting immunotherapy for human renal cell carcinoma: Curative protective tools," Abstract 3136, *Proceedings of the American Association for Cancer Research*, Apr. 10-14, 1999, Philadelphia, PA, vol. 40 (Mar. 1999).

Oosterwijk and Debruyne, "Radiolabeled monoclonal antibody G250 in renal-cell carcinoma," *World Journal of Urology*, 13: 186-190 (1995).

Oosterwijk et al., "The Expression of Renal Antigens in Renal Cell Carcinoma," *World Journal of Urology*, 2(2): 156-158 (1984).

Oosterwijk et al., "Monoclonal Antibodies that Discriminate Between Renal Cell Carcinomas (RCC) and Other Malignancies," *Prostate*, 6(4): 451-452 (Abstract) (1985).

Oosterwijk et al., "Immunohistochemical Analysis of Monoclonal Antibodies to Renal Antigens—Application in the Diagnosis of Renal Cell Carcinoma," *American Journal of Pathology*, 123(2): 301-309 (May 1986).

Oosterwijk et al., "Monoclonal Antibody G250 Recognizes a Determinant Present in Renal-Cell Carcinoma and Absent from Normal Kidney," *Int. J. Cancer*, 38: 489-494 (1986).

Oosterwijk et al., "Relationship between DNA Ploidy, Antigen Expression and Survival in Renal Cell Carcinoma," *Int. J. Cancer*, 42: 703-708 (1988).

Oosterwijk et al., "Expression of Intermediate-sized Filaments in Developing and Adult Human Kidney and Renal Cell Carcinoma," *The Journal of Histochemistry and Cytochemistry*, 38(3): 385-392 (1990).

Oosterwijk et al., "Antibody Localization in Human Renal Cell Carcinoma: A Phase I Study of Monoclonal Antibody G250," *Journal of Clinical Oncology*, 11(4): 738-750 (Apr. 1993).

Oosterwijk et al., "The Use of Monoclonal Antibody G250 in the Therapy of Renal-Cell Carcinoma," *Seminars in Oncology*, 22(1): 34-41 (Feb. 1995).

Oosterwijk et al., "Molecular characterization of the Renal Cell Carcinoma-associated antigen G250," *Proceedings of the American Association for Cancer Research*, 37: 461 (Abstract #3147) (Mar. 1996).

Oosterwijk et al., "Molecular Characterization of the Renal Cell Carcinoma-Associated Antigen G250," *J. Urol.*, 155: 925 (May 1996).

Opavsky et al., "Regulation of MN Expression," *Cell Biology International*, 18(5): Abstract No. Mo-58 (1994).

Opavsky et al., "Human MN/CA9 Gene a Novel Member of the Carbonic Anhydrase Family: Structure and Exon to Protein Domain Relationships," *Genomics*, 33: 480-487 (1996).

Ou et al., MN Promoter Activity in Renal Cell Carcinoma Cell Lines: A Potential for Tissue Restrictive Gene Therapy, *Journal of Urology*, 164(4): Abstract 554 (Apr. 1999).

Pastorek et al., "The Structure and Expression of MN Gene, Coding for a Tumor-Associated Protein p54/58N," *J. Cancer Res., Clin. Oncol*, 119 (Suppl. 1) 10/113 (1993).

Pastorek et al., "Cloning and characterization of MN, a human tumor-associated protein with a domain homologous to carbonic anhydrase and a putative helix-loop-helix DNA binding segment," *Oncogene*, 9: 2877-2888 (1994).

Pastorek et al., "MN—A Novel Type of Oncoprotein," *Cell Biology International*, 18(5): Abstract No. Mo-57 (1994).

Pastorekova et al., "A Novel Quasi-viral Agent, MaTU, Is a Two-Component System," *Virology*, 187: 620-626 (1992).

Pastorekova et al., "Transformation of Mammalian Cells by MN Oncogene," *Cell Biology International*, 18(5): Abstract No. Mo-56 (1994).

Pastorekova et al., "MN/CA IX, a Carbonic Anhydrase Isoenzyme Implicated in Carcinogenesis," Abstract submitted to International Conference on Experimental and Clinical Oncology, Greece (Oct. 3-5, 1996).

Pastorekova et al., "Carbonic Anhydrase IX, MN/CA IX: Analysis of Stomach Complementary DNA Sequence and Expression in Human and Rat Aligemtary Tracts," *Gastroenterology*, 112: 398-408 (1997).

Resnick et al., "Viral and Histopathologic Correlates of MN and MIB-1 Expression in Cervical Intraepithelial Neoplasia," *Human Pathology*, 27(3): 234-239 (Mar. 1996).

Reuters News Report, "Biomarker Resolves Ambiguous Pap Smears" (Mar. 26, 1998).

Saarnio et al., "Distribution of carbonic anhydrase isoenzymes I, II, IV, V, VI and MN/CA IX in the human intestine. An immunohistochemical study," Abstract submitted to to the meeting for United European Gastroenterological Week, Paris, (Nov. 2-6, 1996).

Saarnio et al., "Expression of a Novel Carbonic Anhydrase Isoenzyme, MN/CA IX, In Gallbladder and Hepatitic Tumours," *Gut*, 41(3): PA186-A186 (1997).

Saarnio et al., "Immunohistochemistry of Carbonic Anhydrase Isozyme IX (MN/CA IX) in Human Gut Reveals Polarized Expression in the Epithelial Cells with the Highest Proliferative Capacity," *Journal of Histochemistry & Cytochemistry 46* (4): 497-504 (1998).

Saarnio et al., "Immunohistochemical Study of Colorectal Tumors for Expression of a Novel Transmembrane Carbonic Anhydrase, MN/CA IX, with Potential Value as a Marker of Cell Proliferation," *American Journal of Pathology*, 153(1): 279-285 (Jul. 1998).

Stanbridge, E., "Cervical marker can help resolve ambiguous Pap smears," *Diagnositcs Intelligence*, 10(5): 11 (1998).

Steffens et al., "Radioimmunotargeting with I$^{131}$ labeled chimeric G250 monoclonal antibody in patients with renal cell carcinoma," *J. Nucl. Med.*, 37 (5 Suppl.): 169P (1996).

Steffens et al., "Targeting of Renal Cell Carcinoma with Iodine-131-Labeled Chimeric Monoclonal Antibody G250," *Journal of Clinical Oncology*, 15(4): 1529-1537 (Apr. 1997).

Steffens et al., "Radioimmunotherapy with [131]I-cG250 Monoclonal antibody in Patients with Metastasized RCC, Phase I/II Study," *J. Urology*, 159 (5 Suppl.): Abstract 562 (May 1998).

Surfus et al., "Anti-Renal-Cell Carcinoma Chimeric Antibody G250 Facilitates Antibody-Dependent Cellular Cytotoxicity with In Vitro and In Vivo Interleukin-2-Activated Effectors," *Journal of Immunotherapy* 19(3): 184-191 (1996).

Surfus et al., "Renal Cell Human-Mouse Chimeric Antibody G250 Mediates Antibody Dependent Cellular Cytotoxicity (ADCC)," *Biological Abstracts*, 47(9): 161224 (Abstract 3922) (1995).

Turner et al., "MN Antigen Expression in Normal, Preneoplastic, and Neoplastic Esophagus: a Clinicopathological Study of a New Cancer-Associated Biomarker," *Hum. Pathol.*, 28(6): 740-744 (Jun. 1997).

Tweedie and Edwards, "Mouse Carbonic Anhydrase III: Nucleotide Sequence and Expression Studies," *Biochemical Genetics*, 27(1/2): 17-30 (1989).

Uemura et al., "Internal Image Anti-Idiotype Antibodies Related to Renal-Cell Carcinoma-Associated Antigen G250," *Int. J. Cancer*, 56: 609-614 (1994).

Uemura et al., "Vaccination with Anti-Idiotype Antibodies Mimicking a Renal Cell Carcinoma-Associated Antigen Induces Tumor Immunity," *Int. J. Cancer*, 58: 555-561 (1994).

Uemura et al., "Immunization with Anti-Idiotype Monoclonal Antibodies Bearing the Internal Image of the Renal-Cell Carcinoma-Associated Antigen G250 Induces Specific Cellular Immune Responses," *Int. J. Cancer*, 59: 802-807 (1994).

Uemura et al., "Anti-tumor effects of vaccination with internal image anti-idiotype monoclonal antibodies," *Biotherapy* (Japan), 9(3): 294-295 (1995) (English Language Summary).

Uemura et al., "Possible tools for active specific immunotherapy with anit-idiotype antibodies in human renal cell carcinoma," *Biotherapy* (Japan), 10(3): 241-244 (1996) (English Language Summary).

Uemura et al., "Expression of Tumor-Associated Antigen MN/G250 in Urologic Carcinoma: Potential Therapeutic Target," *Journal Urology*, 157 (4 Supp.): 377 (Apr. 16, 1997)

Uemura et al., "MN Target Immunotherapy for Renal Cell Carcinoma," *J. Urology*, 159 (5 Suppl.): 187, Abstract No. 724 (1998).

Uemura et al., "MN/CA IX/G250 as a potential target for immunotherapy of renal call carcinomas," *Br. J. Cancer*, 81(4): 741-746 (Oct. 1999).

Van Dijk et al., "Induction of Tumor-Cell Lysis by Bi-Specific Monoclonal Antibodies Recognizing Renal-Cell Carcinoma and CD3 Antigen," *Int. J. Cancer*, 43: 344-349 (1989).

Van Dijk et al., "Therapeutic Effects of Monoclonal Antibody G250, Interferons and Tumor Necrosis Factor, In Mice with Renal-Cell Carcinoma Xenografts," *Int. J. Cancer*, 56: 262-268 (1994).

Vermylen et al., "Expression of the MN antigen as a biomarker of lung carcinoma and associated precancerous conditions," *Proceedings of the American Association for Cancer Research*, (Abstract #2280) (Mar. 1998).

Vermylen et al., "Carbonic anhydrase IX antigen differentiates between preneoplastic malignant lesions in non-small cell lung carcinoma," *Eur Respir J*, 14: 806-811 (1999).

Vessella et al., "Monoclonal antibodies to human renal cell carcinoma: recognition of shared and restricted tissue antigens," *Cancer Res.*, 45 (12, Pt. 1): 6131-6139 (1985).

Vissers et al., "Immunogenicity of the renal cell carcinoma antigen G250," Abstract 2804, *Proceedings of the American Association for Cancer Research*, Apr. 10-14, 1999, Philadelphia, PA, vol. 40 (Mar. 1999).

Young and Davis, "Efficient Isolation of Genes by Using Antibody Probes," *PNAS* (USA) 80: 1194-1198 (Mar. 1983).

Zavada, "The Pseudotypic Paradox," *J. gen. Virol.*, 63: 15-24 (1982).

Zavada and Zavadova, "A Transmissible Antigen Detected in Two Cell Lines Derived from Human Tumours," *J. gen. Virol.*, 24: 327-337 (1974).

Zavada and Zavadova, "An unusual transmissible agent—MaTu," *Arch. Virol.*, 118: 189-197 (1991).

Zavada et al., "VSV Pseudotype Produced in Cell Line derived from Human Mammary Carcinoma," *Nature New Biology*, 240: 124-125 (Nov. 22, 1972).

Zavada et al., "Tumorigenicity-Related Expression of MaTu Proteins in HeLa × Fibroblast Hybrids," Abstract presented at the XIX Meeting of the European Tumor Virus Group (May 1-4, 1991).

Zavada et al., "A Presumed New Oncoprotein—MN—Used as Experimental Antitumor Vaccine," *J. Cancer Res. Clin. Oncol.*, 119, (Suppl. 1) 2/24 (1993).

Zavada et al., "Expression of MaTu-MN Protein in Human Tumor Cultures and in Clinical Specimens," *Int. J. Cancer*, 54: 268-274 (1993).

Zavada et al., "MN—A Novel Type of Human Oncogene," Abstract submitted to EMBL Conference: Oncogenes & Growth Control, Heidelberg (Apr. 21-24, 1996).

Zavada et al., "A novel oncoprotein, MN, implicated in cervical carcinoma," Abstract submitted to ETVG Meeting, Innsbruck (Mar. 1997).

Zavada et al., "Transient transformation of mammalian cells by MN protein, a tumor-associated cell adhesion molecule with carbonic anhydrase activity," *International Journal of Oncology*, 10: 857-863 (1997).

Zavadova et al., "Novel tumor-associated MN protein is a cell adhesion molecule," for conference on Molecular Genetics of Cancer, Oxford, Sep. 1997.

* cited by examiner

| | | | | | | | | | | | | |
|---|---|---|---|---|---|---|---|---|---|---|---|---|
| 1 1 | ACA | GTC | AGC | CGC | M<br>ATG | A<br>GCT | P<br>CCC | L<br>CTG | C<br>TGC | P<br>CCC | S<br>AGC | P<br>CCC | W<br>TGG | L<br>CTC | P<br>CCT | L<br>CTG | 12<br>48 |
| 13 49 | L<br>TTG | I<br>ATC | P<br>CCG | A<br>GCC | P<br>CCT | A<br>GCT | P<br>CCA | G<br>GGC | L<br>CTC | T<br>ACT | V<br>GTG | Q<br>CAA | L<br>CTG | L<br>CTG | S<br>TCA | 28<br>96 |
| 29 97 | L<br>CTG | L<br>CTT | M<br>ATG | L<br>CTG | M<br>ATG | P<br>CCT | V<br>GTC | H<br>CAT | P<br>CCC | Q<br>CAG | R<br>AGG | L<br>TTG | P<br>CCC | R<br>CGG | M<br>ATG | Q<br>CAG | 44<br>144 |
| 45 145 | E<br>GAG | D<br>GAT | S<br>TCC | P<br>CCC | L<br>TTG | G<br>GGA | G<br>GGA | G<br>GGC | S<br>TCT | Q<br>CAG | G<br>GGG | E<br>GAA | R<br>AGG | D<br>GAT | D<br>GAC | P<br>CCA | L<br>CTG | 60<br>192 |
| 61 193 | G<br>GGC | E<br>GAG | E<br>GAG | D<br>GAT | L<br>CTG | P<br>CCC | S<br>AGT | E<br>GAA | E<br>GAA | D<br>GAT | S<br>TCA | E<br>GAG | E<br>GAG | E<br>GAG | E<br>GAG | D<br>GAT | 76<br>240 |
| 77 241 | P<br>CCA | P<br>CCC | G<br>GGA | E<br>GAG | E<br>GAG | L<br>CTA | P<br>CCT | S<br>TCA | P<br>CCC | D<br>GAT | L<br>CTA | P<br>CCT | R<br>AGA | E<br>GAG | P<br>CCT | G<br>GGA | E<br>GAG | 92<br>288 |
| 93 289 | E<br>GAG | D<br>GAT | L<br>CTA | P<br>CCT | E<br>GAA | V<br>GTT | K<br>AAG | P<br>CCT | T<br>ACT | V<br>GTT | E<br>GAG | A<br>GCT | P<br>CCT | S<br>TCA | E<br>GAA | S<br>TCC | L<br>CTG | 108<br>336 |
| 109 337 | K<br>AAG | L<br>TTA | E<br>GAG | D<br>GAT | D<br>GAT | L<br>CTA | H<br>CAC | A<br>GCC | K<br>AAA | R<br>AGG | D<br>GAC | K<br>AAA | E<br>GAA | G<br>GGG | D<br>GAT | D<br>GAC | Q<br>CAG | E<br>GAA | H<br>CAT | 124<br>384 |
| 125 385 | P<br>CCC | Q<br>CAG | N<br>AAT | N<br>AAT | A<br>GCC | H<br>CAC | R<br>AGG | D<br>GAC | K<br>AAA | E<br>GAA | G<br>GGG | D<br>GAT | D<br>GAC | Q<br>CAG | S<br>AGT | H<br>CAT | 140<br>432 |
| 141 433 | W<br>TGG | R<br>CGC | Y<br>TAT | G<br>GGA | G<br>GGA | D<br>GAC | P<br>CCG | P<br>CCC | W<br>TGG | P<br>CCC | R<br>CGG | V<br>GTG | S<br>TCC | P<br>CCA | A<br>GCC | C<br>TGC | 156<br>480 |
| 157 481 | A<br>GCG | G<br>GGC | R<br>CGC | F<br>TTC | Q<br>CAG | S<br>TCC | P<br>CCG | V<br>GTG | D<br>GAT | I<br>ATC | R<br>CGC | P<br>CCC | Q<br>CAG | L<br>CTC | A<br>GCC | A<br>GCC | 172<br>528 |

FIG._1A

| | F | C | P | A | L | R | P | L | E | L | L | G | F | Q | L | P | 188 |
|---|---|---|---|---|---|---|---|---|---|---|---|---|---|---|---|---|---|
| 173 | TTC | TGC | CCG | GCC | CTG | CGC | CCC | CTG | GAA | CTC | CTG | GGC | TTC | CAG | CTC | CCG | 576 |
| | P | L | P | E | L | R | L | R | N | N | G | H | S | V | Q | L | 204 |
| 189 | CCG | CTC | CCA | GAA | CTG | CGC | CTG | CGC | AAC | AAT | GGC | CAC | AGT | GTG | CAA | CTG | 624 |
| | T | L | P | P | Q | L | E | M | A | A | L | G | R | E | Y | 220 |
| 205 | ACC | CTG | CCT | GGG | CTA | CAG | GAG | ATG | GCT | CTG | GGG | GCA | GGT | CGG | GAG | TAC | 672 |
| | R | A | L | Q | L | H | W | H | G | A | P | A | G | R | P | G | 236 |
| 221 | CGG | GCT | CTG | CAG | CTG | CAT | TGG | CAC | GGC | GCA | GCT | GGG | CGA | CGT | CCG | GGC | 720 |
| | S | E | H | T | V | E | R | F | P | A | E | I | H | V | 252 |
| 237 | TCG | GAG | CAC | ACT | GTG | GAA | CGT | TTC | CCT | GCC | GAG | ATC | CAC | GTG | 768 |
| | V | H | L | S | T | A | A | F | A | R | L | D | E | L | G | R | 268 |
| 253 | GTT | CAC | CTC | AGC | ACC | GCC | TTT | GCC | CGT | AGA | TTG | GAC | GAG | CTG | GGG | CGC | 816 |
| | P | G | G | L | A | V | E | Q | L | L | A | E | E | E | I | A | 284 |
| 269 | CCG | GGA | GGC | CTG | GCC | GTG | GAG | CAG | TTG | CTG | GCC | GAG | GAG | GAA | ATC | GCT | 864 |
| | E | N | S | A | Y | E | T | L | S | R | L | D | I | S | A | L | 300 |
| 285 | GAA | AAC | AGT | GCC | TAT | GAG | ACT | CTG | TCT | CGC | TTG | GAC | ATA | TCT | GCA | CTC | 912 |
| | E | G | S | D | F | R | Y | Q | P | G | Y | E | G | S | L | T | 316 |
| 301 | GAG | GGC | TCA | GAG | GAC | TTC | AGC | CGC | TAC | CAA | CCA | GGA | TAT | GAG | GGG | CTC | 960 |
| | L | P | S | D | F | S | R | Y | Q | P | V | F | Y | E | G | S | L | T | 332 |
| 317 | CTG | CCC | TCT | GAC | TTC | AGC | CGC | TAC | CAA | CCA | GTC | TTC | TAT | GAG | GGG | TCT | CTG | ACT | 1008 |
| | T | P | C | A | Q | G | V | I | W | T | V | F | N | Q | T | 348 |
| 333 | ACA | CCG | CCC | TGT | GCC | CAG | GGT | GTC | ATC | TGG | ACT | GTG | TTT | AAC | CAG | ACA | 1056 |

```
349  V   M   L   S   A   K   Q   L   H   T   L   S   D   T   L   W   364
1057 GTG ATG CTG AGT GCT AAG CAG CTC CAC ACC CTC TCT GAC ACC CTG TGG 1104

365  G   P   G   D   S   R   L   Q   N   F   R   A   T   Q   P   380
1105 GGA CCT GGT GAC TCT CGG CTA CAG AAC TTC CGA GCG ACG CAG CCT 1152

381  L   N   G   R   V   I   E   A   S   F   P   A   G   V   D   S   396
1153 TTG AAT GGG CGA GTG ATT GAG GCC TCC TTC CCT GCT GGA GTG GAC AGC 1200

397  S   P   R   A   A   L   V   Q   L   N   S   C   L   F   A   A   412
1201 AGT CCT CGG GCT GCT CTA GTC CAG CTG AAT TCC TGC CTG TTT GCT GCT 1248

413  G   D   I   A   F   L   V   M   R   R   Q   H   L   L   R   R   428
1249 GGT GAC ATC GCC CTA CTT GTT CAG ATG AGA AGG CAG CAC CTC CTT CGT 1296

429  V   A   F   L   V   Q   R   Y   P   A   E   R   A   E   T   G   K   444
1297 GTC GCG TTC CTT GTG CAG CGC TAC CCA GCA GAG AGG GCT GAG ACT GGA ACC AAA 1344

445  G   G   V   S   Y   P   A   E   V   A   R   G   A   *   460
1345 GGG GGT GTG AGC TAC CGC CCA GCA GAG GTA GCC ACT GGA GCC TAG 1392

1393 AGG CTG GAT CTT GGA GAA TGT CCT GTC CTG CTC ATT ATG CCA AGA GGC ATC TGA GGG 1440

1441 GGA GCC GGT AAC TGT CCT GTC CTG CTC ATT ATG CCA CTT CCT TTT AAC 1488

1489 TGC CAA GAA ATT TTT TAA AAT AAA TAT TTA TAA T 1522
```

FIG._1

| |
|---|
| FIG._1A |
| FIG._1B |
| FIG._1C |

```
   1 ggatcctgtt gactcgtgac cttaccccca accctgtgct ctctgaaaca tgagctgtgt
  61 ccactcaggg ttaaatggat taagggcggt gcaagatgtg cttgttaaa cagatgcttg
 121 aaggcagcat gctcgttaag agtcatcacc aatccctaat ctcaagtaat caggacaca
 181 aacactgcgg aaggccgcag ggtcctctgc ctaggaaaac cagagacctt tgttcacttg
 241 tttatctgac cttccctcca ctattgtcca tgaccctgcc aatccccct ctgtgagaaa
 301 cacccaagaa ttatcaataa aaaataaat ttaaaaaaaa aatacaaaaa aaaaaaaaa
 361 aaaaaaaaaa gacttacgaa tagttattga taaatgaata gctattggta aagccaagta
 421 aatgatcata ttcaaaacca dacggccatc atcacagctc agtctacct gatttgatct
 481 ctttatcatt gtcattcttt ggattcacta gattagtcat catcctcaaa attctccccc
 541 aagttctaat tacgttccaa acattaggg gttacatgaa gctgaacct actaccttct
 601 ttgcttttga gccatgagtt gtaggaatga tgagtttaca cctacatgc tggattaa
 661 tttaaactt accctctaagt cagttgggta gcctttggct tatttttgta gctaattttg
 721 tagttaatgg atgcactgtg aatcctgcta tgatagttt cctccacact ttgccactag
 781 gggtaggtag gtactcagtt ttcagtaatt gcttacctaa gacccctaagc cctattctc
 841 ttgtactggc ctttatctgt aatatgggca tatttaatac aatataattt ttgagtttt
 901 tttgttttgtt tgttgttttg ttttttttgag acggagtctt gcatctgtca tgcccaggct
 961 ggagtagcag tggtgccatc tcggctcact gcaagctcca cctcccgagt tcacgccatt
1021 ttcctgcctc agcctcccga gtagctggga ctacaggcgc ccgccaccat gcccggctaa
1081 ttttttgtat ttttggtaga cacggggttt caccgtgtta gccagaatgg tctcgatctc
1141 ctgacctcgt gatccaccg cctcgcctc ccaagtgct gggattacag gtgtgagcca
1201 ccgcacctgg ccaatttttt gagtctttta agtaaaat atgtcttgta agctggtaac
1261 tatggtacat ttccttttat taatgtggtg ctgacggtca tataggttct tttgagtttg
1321 gcatgcatat gctactttt gcagtccttt cattacattt ttctctcttc atttgaagag
1381 catgttatat cttttagctt cacttgctt aaaaggttct tcattagcc taacacagtg
1441 tcattgttgg taccacttgg atcataagtg gaaaaacagt caagaaattg cacagtaata
1501 cttgtttgta agaggatga ttcaggtgaa tctgacacta agaaactcc ctacctgagg
1561 tctgagattc ctctgacatt gctgtatata gctcttttcct ttgacagcct gtgactgcgg
1621 actattttc ttaagcaaga tatgctaaag tttgtgagc ctttttccag agagaggtct
1681 catatctgca tcaagtgaga acatatataaag tctgcatgtt tccatatttc aggaatgttt
1741 gcttgtgttt tatgcttta tatagacagg gaaacttgtt cctcagtgac ccaaaagagg
1801 tgggaattgt ttattgatat catcattggc ccacgctttc tgacctttga aacaattaag
1861 ggttcataat ctcaattctg tcagaattgg tacaagaaat agctgctatg tttcttgaca
1921 ttccacttgg taggaaataa gaatgtgaaa ctcttcagtt ggtgtgtc cct?gttttt
```

FIG._2A

```
1981 ttgcaatttc ctccttactg tgttaaaaaa aagtatgatc ttgctctgag aggtgaggca
2041 ttcttaatca tgatctttaa agatcaataa tataatcctt tcaaggatta tgtctttatt
2101 ataataaaga taatttgtct ttaacagaat caataatata atcccttaaa ggattatatc
2161 tttgctgggc gcagtggctc acacctgtaa tcccagcact ttgggtggcc aaggtggaag
2221 gatcaaattt gcctactcct atattatctt ctaaagcaga attcatctct cttccctcaa
2281 tatgatgata ttgacaggt ttgcctcac tcactagatt gtgagctcct gctcaggca
2341 ggtagcgttt tttgttttg tttgttttt tctttttga gacagggtct tgctctgtca
2401 cccaggccag agtgcaatgg tacagtctca gctcactgca gcctcaaccg cctcggctca
2461 aaccatcatc ccatttcagc ctcctgagta gctgggacta caggcacatg ccattacacc
2521 tgctaattt tttgtattt ctagtagaga cagggtttg ccatgttgcc cgggctggtc
2581 tcgaactcct ggactcaagc aatccaccca cctcagcctc ccaaaatgag ggaccgtgtc
2641 ttattcattt ccatgtccct agtccatagc ccagtgctgg acctatggta gtactaaata
2701 aatattgtt gaatgcaata gtaaatagca tttcaggag caagaactag attaacaaag
2761 gtggtaaaag gttggagaa aaaataata gttaatttg gctagagtat gagggagagt
2821 agtaggagac aagatggaaa ggtctcttgg gcaaggtttt gaaggaagtt ggaagtcaga
2881 agtacacaat gtgcatatcg tggcaggcag tggggagcca atgaaggctt ttgagcagga
2941 gagtaatgtg ttgaaaaata aatataggtt aaacctatca gagcccctct gacacataca
3001 ctgctttc attcaagctc aagtttgtct cccacatacc cattacttaa ctcaccctcg
3061 ggctcccta gcagcctgcc ctacctctt acctgcttcc tggtggagtc agggatgtat
3121 acatgagctg ctttccctct cagccagagg acatgggggg cccagctcc cctgcttc
3181 cccttctgtg cctgagctg ggaagcaggc caggttagc tgaggctggc tggcaagcag
3241 ctgggtggtg ccaggagag cctgcatagt gccaggtggt gccttgggtt ccaagctagt
3301 ccatgccccc gataaccttc tgcctgtgca cacacctgcc cctcactcca ccccatcct
3361 agctttggta tgggggagag ggcacagggc cagacaaaacc tgtgagactt tgctccatc
3421 tctgcaaaag ggcgctctgt gagtcagcct gctcccctcc agcttgctc ctccccacc
3481 cagctctcgt ttccaatgca cgtacagccc gtacacaccg tgtgctggga caccCACAG
3541 TCAGCCGCAT GGCTCCCCTG TGCCCCAGCC CCTGGCTCCC TCTGTTGATC CCGGCCCCTG
3601 CTCCAGGCCT CACTGTGCAA CTGCTGCTGT TCTGGTGCCT GTCCATCCCC
3661 AGAGGTTGCC CCGGATGCAG GAGGATTCCC CCTTGGGAGG AGGCTCTTCT GGGGAAGATG
3721 ACCCACTGGG CGAGGAGGAT CTGCCCAGTG AAGAGGATTC ACCCAGAGAG GAGGATCCAC
3781 CCGGAGAGGA GGATCTACCT GGAGAGGAGG ATCTACCTGG AGAGGATGAT CTACCTGAAG
3841 TTAAGCCTAA ATCAGAAGAA GAGGGCTCCC TGAAGTTAGA GGATCTACCT ACTGTTGAGG
3901 CTCCTGGAGA TCCTCAAGAA CCCCAGAATA ATGCCCACAG GGACAAAGAA Ggtaagtggt
```

FIG._2B

```
3961 catcaatctc caaatccagg ttccaggagg ttcatgactc ccctcccata cccagccta
4021 ggctctgttc actcaggaa ggaggggaga ctgtactccc cacagaagcc cttccagagg
4081 tccatacca atatccccat ccccactctc ggaggtagaa agggacagat gtggagagaa
4141 aataaaaagg gtgcaaaagg agagaggtga gctggatgag atgggagaga aggggaggc
4201 tggagaagag aaaggggatga gaactgcaga tgagagaaaa aatgtgcaga cagaggaaaa
4261 aaataggtgg agaaggagag tcagagagtt tgaggggaag agaaaaggaa agctggag
4321 gtgaagtggg taccagagac aagcaagaag agctggtaga agtcatctca tcttaggcta
4381 caatgaggaa ttgagaccta ggaagaaggg acacagcagg tagagaaacg tggcttcttg
4441 actcccaagc caggaatttg gggaaagggg ttgagacca tacaaggcag agggatgagt
4501 ggggagaaga aagaaggag aaagaaaaga tggtgtactc actcatttgg gactcaggac
4561 tgaagtgccc actcactttt tttttttttt tttttgagac aaactttcac tttgttgcc
4621 caggctggag tgcaatggcg cgatctcggc tcactgcaac ctccacctcc cgggtcaag
4681 tgattctcct gcctcagcct ctagccaagt agctgcgatt acaggcatgc gccaccacgc
4741 ccggctaatt tttgtatttt tagtagagac gggtttcgc catgttggtc agctggtct
4801 cgaactcctg atctcaggtg atccaaccac cctggcctcc caaagtgctg ggattatagg
4861 cgtgagccac agcgcctgc ctgaagcagc ctgaattgtt tacagaccct aagacaatga
4921 tgtcaagctg gtaggattgc tgttggccc ggtgttgagt accgtaatg ttgggtgcgg
4981 tctcctgtgc tttgcacctg gttgtgacatc gcccgcttaa ggcatttgtt accgtaatg ctcctgtaag
5041 gcatctgcgt ttgtgcatc gttttggtcg ccaggaaggg attgggctc ctgtgatct cccctacagc
5101 cggttcatcc ttttcattta tacagGGGAT GACCAGAGTC ATTGGCGCTA TGGAGgtgag cccctcacct
5161 acaccaccc gctgcacaga cccaatctgg gaaccagct cccgccgcc accgtcccac tatactctcc
5221 cgtccctgaa cactgtccc gggcgtccca ggccgtgac acttcctcac acttcctcac GCTTCCAGTC
5281 tttctacccg ggttccctaa gttcctgacc taggcgtcag GCCCTGCGCC CCCTGAACT
5341 caccccagGC GACCCGCCCT GGCCCCGGGT GTCCCCAGCC CTTCTGCCCG CGCCTGCGCC CCCTGAACT
5401 CCCGGTGGAT ATCCGCCGC AGCTCGCCGC CGCTCCCCGA ACTGCGCCTG CGCAACAATG GCCACAGTGg
5461 CCTGGGCTTC CAGTCCCCGC CGCTCCCCGA gacttgggga tgggcgggg cgcaggaag ggaaccgtcg
5521 tgagggggtc tccccgccga gacttgggga tgggctggcc ctaccggcg gggccggctc acttgcctct
5581 cgcagtgcct gccgggggt tgggctggcc ctgcctcct GGGCTAGAGA TGGCTCTGGG TCCGGGCGG
5641 ccctacgcag TGCAACTGAC CCTGCCTCCT GCATCTGCAC TGGGGGGCTG CAGGTCGTCC GGGCTCGGAG
5701 GAGTACCGGG CTCTGCAGCT GCATCTGCAC TTTCCCTGCC GAGtgagcg cggactgcc gagaagggc
5761 CACACTGTGG AAGGCCACCG TTTCCCTGCC ggcagagac cctaccctcg tgtccttttc
5821 aaaggagcgg ggcgacggg ggcagagac cctaccctcg tgtccttttc
5881 agATCCACGT GGTTCACCTC AGCACCGCTC TTGCCAGAGT TGACGAGGCC TTGGGGCGCC
```

FIG._2C

```
5941 CGGGAGGCCT GGCCGTGTTG GCCGCCTTTC TGGAGtacc  agatcctgga  cacccctac
6001 tcccgcttt  cccatcccat gctcctcccg gactctatcg  tgagccaga   gacccatcc
6061 cagcaagctc actcaggccc ctggctgaca aactcattca  cgcactgttt  gttcatttaa
6121 cacccactgt gaaccaggca ccagccccca acaaggattc  tgaagctgta  ggtccttgcc
6181 tctaaggagc ccacagccag tggggaggc  tgacatgaca  gacacatagg  aaggacatag
6241 taaagatggt ggtcacagag gaggtgacac ttaaagcctt  cactggtaga  aaagaaaagg
6301 agtgttcat  tgcagaggaa acagaatgtg caaagactca  gaatatggcc  tatttaggga
6361 atggctacat acaccatgat tagaggaggc ccagtaaagg  gaagggatgg  tgagatgcct
6421 gctaggttca ctcactcact tttattattt tatttatttt  tttgacagtc  tctctgtcgc
6481 ccaggctgga gtgcagtggt gtgatcttgg gtcactgcaa  cttccgcctc  ccgggttcaa
6541 gggattctcc tgcctcagct tcctgagtag ctggggttac  agtgtgtgc   caccatgccc
6601 agctaatttt tttttgtatt tttagtagac agggtttcac  catgttggtc  aggctggtct
6661 caaactcctg gcctcaagtg atccgcctga ctcagcctga  caaagtgctg  attacaagtg
6721 tgagccaccg tgcccagcca cactcactga ttctttaatg  ccagccacac  agcacaaagt
6781 tcagagaaat gcctccatca tagcatgtca atatgttcat  actcttaggt  tcatgatgtt
6841 cttaacatta ggttcataag caaataaaga aaaagaata   ataaataaaa  gaagtggcat
6901 gtcaggacct cacctgaaaa gccaaacaca gaatcatgaa  ggtgaatgca  gaggtgacac
6961 caacacaaag gtgtatatat ggtttcctgt ggggagtatg  tacggaggca  gcagtgagtg
7021 agactgcaaa cgtcagaagg gcacgggtca ctgagagcct  agtatcctag  taaagtgggc
7081 tctctccctc tctctccagc ttgtcattga aaaccagtcc  accaagcttg  ttggttcgca
7141 cagcaagagt acatagagtt tgaaataata catagagatt  taagagggag  acactgtctc
7201 taaaaaaaaa aacaacagca acaacaaaca acaacaaaca  ttacaatttt  atgttccctc
7261 agcattctca gagctgagga atgggaggg  actatgggaa  ccccctcat   gttccggcct
7321 tcagccatgg ccctgatac  atgcactcat ctgtcttaca  atgtcattcc  cccagGAGGG
7381 CCCGGAAGAA AACAGTGCCT ATGAGCAGTT GCTGTCTCGC  TTGGAAGAAA  TCGCTGAGGA
7441 AGtcagttt  gttggtctgg ccactaatct ctgtggccta  gttcataaag  aatcacccttt
7501 tggagcttca ggtctgaggc tggagatggg ctccctccag  tgcaggaggg  attgaagcat
7561 gagccagcgc tcatccttgat aataaccatg aagctgacag aagctgacac  acacagttac  ccgcaaacgg
7621 ctgcctacag attgaaaaacc aagcaaaaac cgccgggcac  ggtggctcac  gcctgtaatc
7681 ccagcacttt gggaggccaa ggcaggtgga tcacgaggtc  aagagatcaa  gaccatcctg
7741 gccaacatgg tgaaacccca tctctactaa aaatacgaaa  aaatagccag  gcgtggtggc
7801 gggtgcctgt aatcccagct actcgggagg ctgaggcagg  agaatggcag  aacccggga
7861 gcagagtt   gcagtgagcc gagatcgtgc cactgcactc  cagcctgggc  aacagagcga
```

FIG._2D

```
7921 gactcttgtc tcaaaaaaaa aaaaaaaaaa gaaaaccaag caaaaaccaa aatgagacaa
7981 aaaaaacaag accaaaaaat ggtgtttgga aattgtcaag gtcaagtctg gagagctaaa
8041 cttttctga gaactgttta tctttaataa gcatcaaata tttaactttt gtaaatactt
8101 ttgttgaaaa tcgttctctt cttagtcact ctgggtcat tttaaatctc acttactcta
8161 ctagaccttt taggttttctg ctagactagg tagaactctg cctttgcatt tcttgtgtct
8221 gttttgtata gttatcaata ttcatattta tttacaagtt attcagatca ttttttttt
8281 tctttttttt tttttttttt tttttacat cttagtaga gacagggttt caccatattg
8341 gccaggctgc tctcaaactc ctgacccttgt gatccaccag cctcggcctc ccaaagtgct
8401 gggattcatt tttttttttt aatttgctct gggcttaaac ttgtggccca gcacttatg
8461 atggtacaca gagttaagag tgtagactca gacggtcttt ctccttttcct tctcttcctt
8521 cctcccttcc ctcccacctt ccctctctc ctccttctct ttctccttct cttgcttcct
8581 caggcctctt ccagttgctc caaagccctg tactttttt tgagttaacg tcttatggga
8641 agggcctgca cttagtgaag aagtggtctc agagttgagt taccttggct tctgggaggt
8701 gaaactgtat ccctataccc tgaagcttta agggggtgca atgtagatga gacccaaca
8761 tagatccctct tcacagGCTC AGAGACTCAG GTCCCAGGAC TGGACATATC TGCACTCCTG
8821 CCCTCTGACT TCAGCCGCTA CTTCCAATAT GAGGGGTCTC TGACTACACC GCCCTGTGCC
8881 CAGGGTGTCA TCTGGACTGT GTTTAACCAG ACAGTGATGC TGAGTGCTAA GCAGgtgggc
8941 ctggggtgtg tgtggacaca gtgggtgcgg gggaaagagg atgtaagatg agatgagaaa
9001 caggagaaga aagaaatcaa ggctgggctc tgtgcttac gcctataatc ccaccacgtt
9061 gggaggctga ggtggagaa tggtttgagc ccaggagttc aagacaaggc gggcaacat
9121 agtgtgaccc catctctacc aaaaaaaccc caacaaaacc aaaaatagcc gggcatggtg
9181 gtatgcggcc tagtcccagc tactcaagga ggctgaggtg ggaagatcgc ttgattccag
9241 gagtttgaga ctgcagtgag ctatgatccc accactgcct accatccttta ggatacattt
9301 atttatttat aaaagaaatc aagaggctgg atggggaata caggagctgg agggtggagc
9361 cctgaggtgc tggttgtgag ctggcctggg acccttgttt cctgtcatgc catgaaccca
9421 cccacactgt ccactgacct ccctagCTCC ACACCCTCTC TGACACCCTG TGGGGACCTG
9481 GTGACTCTCG GCTACAGCTG AACTTCCAGG CGACGCAGCC TTTGAATGGG CGAGTGATTG
9541 AGGCCTCCTT CCCTGCTGGA GTGGACAGCA GTCCTCGGGC TGCTGAGCCA Ggtacagctt
9601 tgtctgtttt cccccagcc agtagtccct tatcctccca tgtgtgcc agtgtctgtc
9661 attggtggtc acagcccgcc tctcacatct cctttttctc tccagTCCAG CTGAATTCCT
9721 GCCTGGCTGC TGgtgagtct gccccctcc ttggtcctga tgccaggaga ctcctcagca
9781 ccattcagcc ccaggctgc tcagaccgc tctgctccc tctcctttc tgcagaacag
9841 acccaaccc caatattaga gaggcagatc atggtgggga ttccccatt gtcccagag
```

FIG._2E

```
 9901 gctaattgat tagaatgaag cttgagaaat ctcccagcat ccctctcgca aaagaatccc
 9961 ccccccttt tttaaagata gggtctcact ctgtttgccc caggctgggg tgttgtggca
10021 cgatcatagc tcactgcagc ctcgaactcc taggctcagg caatccttc accttagctt
10081 ctcaaagcac tgggactgta ggcatgagcc actgtgcctg gcccaaaacg gcccttttac
10141 ttggcttta ggaagcaaaa acgtgctta tcttaccct tctcgtgtat ccaccctcat
10201 cccttggctg gcctcttctg gagactgagg cactatgggg ctgcctgaga actcggggca
10261 ggggtgtgg agtgcactga ggcaggtgtt gaggaactct gcagacccct cttccttccc
10321 aaagcagccc tctctgctct ccatcgcagG TGACATCCTA GCCCTGGTTT TTGGCCTCCT
10381 TTTTGCTGTC ACCAGCGTCG CGTTCCTTGT GCAGATGAGA AGGCAGCACA Gtattacac
10441 tgacccttc ttcaggcaca agcttccccc acccttgtgg agtcacttca tgcaaagcgc
10501 atgcaaatga gctgcctg gccagtttt ggccagtagcc ctgattagcc tttcctgttg tgtacacaca
10561 gAAGGGGAAC CAAAGGGGGT GTGAGCTACC GCCCAGCAGA GGTAGCCGAG ACTGGAGCCT
10621 AGAGGCTGGA TCTTGGAGAA TGTGAGAAGC CAGCCAGAGG CATCTGAGGG GGAGCCGGTA
10681 ACTGTCCTGT CCTGCTCATT ATGCCACTTC CTTTTAACTG CCAAGAAATT TTTTAAAATA
10741 AATATTTATA ATaaaatatg tgttagtcac ctttgttccc caaatcagaa ggagtattt
10801 gaatttccta ttactgttat tagcaccaat ttagtggtaa tgcatttatt ctattacagt
10861 tcggcctcct tccacacatc actccaatgt gttgctcc
```

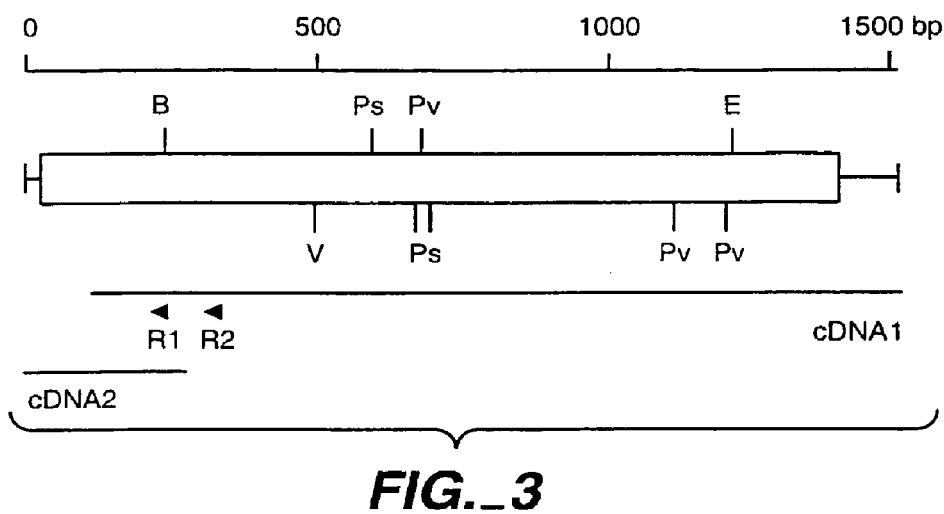
FIG._3
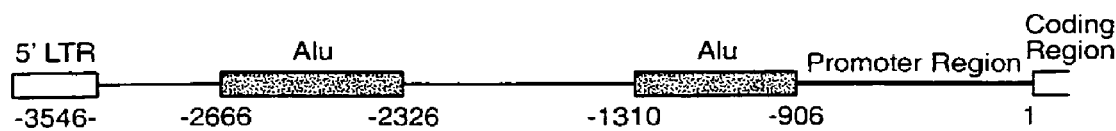
FIG._4
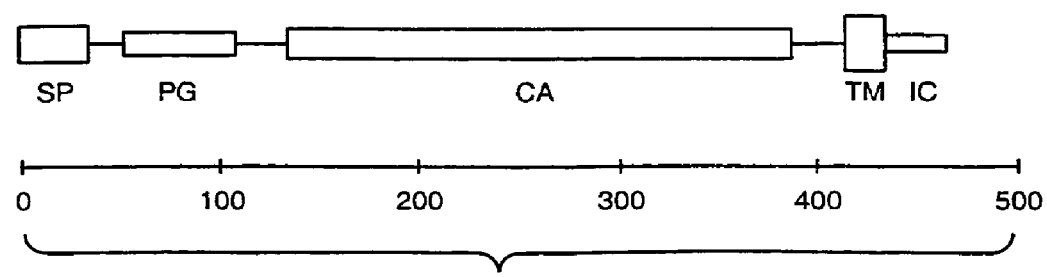
FIG._8

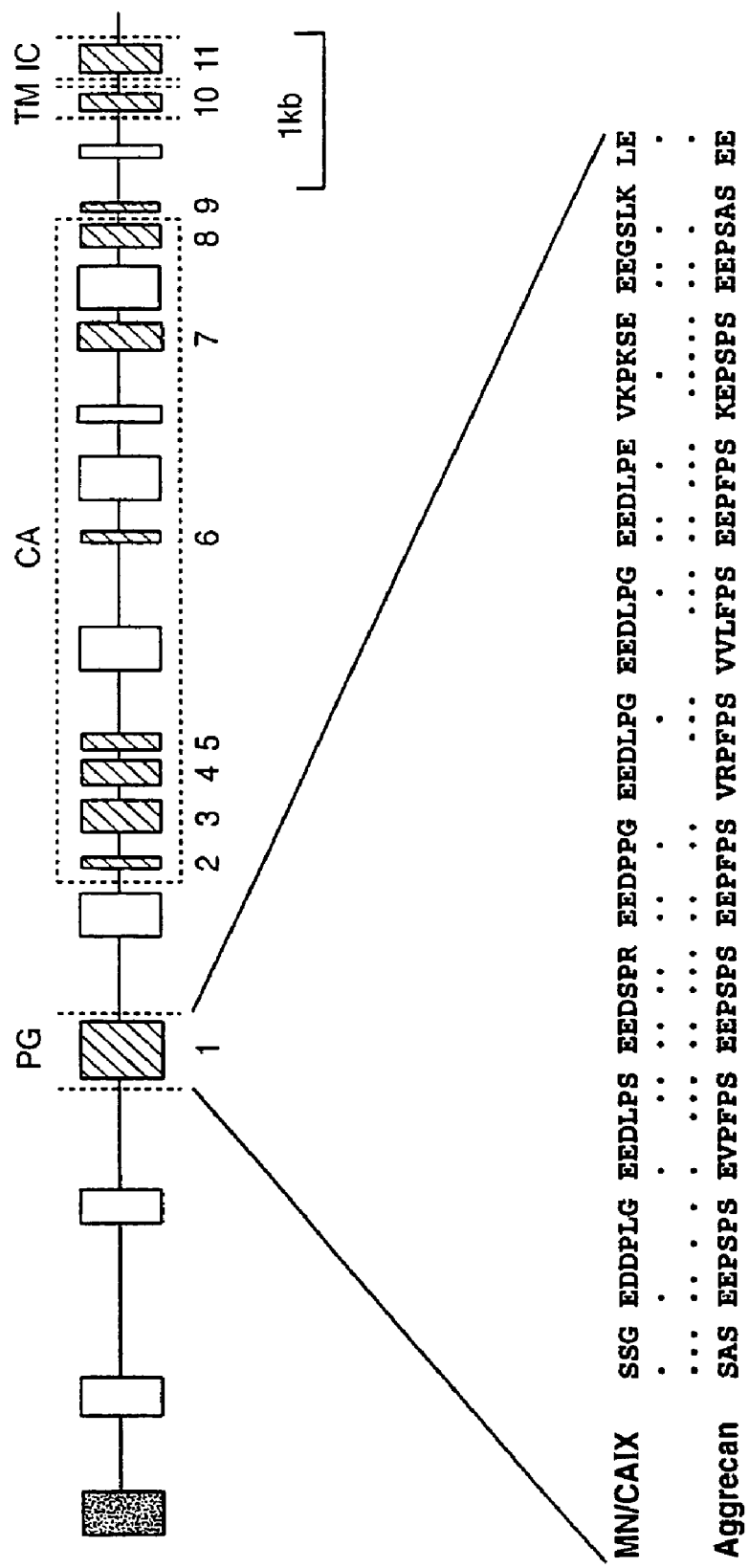
FIG._5

```
-506                   CTTGCTTTTC ATTCAAGCTC AAGTTTGTCT CCCACATACC CATTACTTAA CTCACCCTCG

-446  GGCTCCCCTA GCAGCCTGCC CTACCTCTTT ACCTGCTTCC TGGTGGAGTC AGGGATGTAT
           AP2

-386  ACATGAGCTG CTTTCCCTCT CAGCCAGAGG ACATGGGGGG CCCCAGCTCC CCTGCCTTTC

-326  CCCTTCTGTG CCTGGAGCTG GGAAGCAGGC CAGGGTTAGC TGAGGCTGGC TGGCAAGCAG

-266  CTGGGTGGTG CCAGGGAGAG CCTGCATAGT GCCAGGTGGT GCCTTGGGTT CCAAGCTAGT
                                              VII                       p53

-206  CCATGGCCCC GATAACCTTC TGCCTGTGCA CACACCTGCC CCTCACTCCA CCCCCATCCT
            VI                                                    Inr       V

-146  AGCTTTGGTA TGGGGGAGAG GGCACAGGGC CAGACAAACC TGTGAGACTT TGGCTCCATC
                                              IV                 AP1           III   Inr

-86   TCTGCAAAAG GGCGCTCTGT GAGTCAGCCT GCTCCCCCTC AGGCTTGCTC CTCCCCCACC
                                  AP1                       p53        I   AP2
                                  ***

-26   CAGCTCTCGT TTCCAATGCA CGTACACGCCC GTACACACCG TGTGCTGGGA CACCCCACAG
```

FIG._6

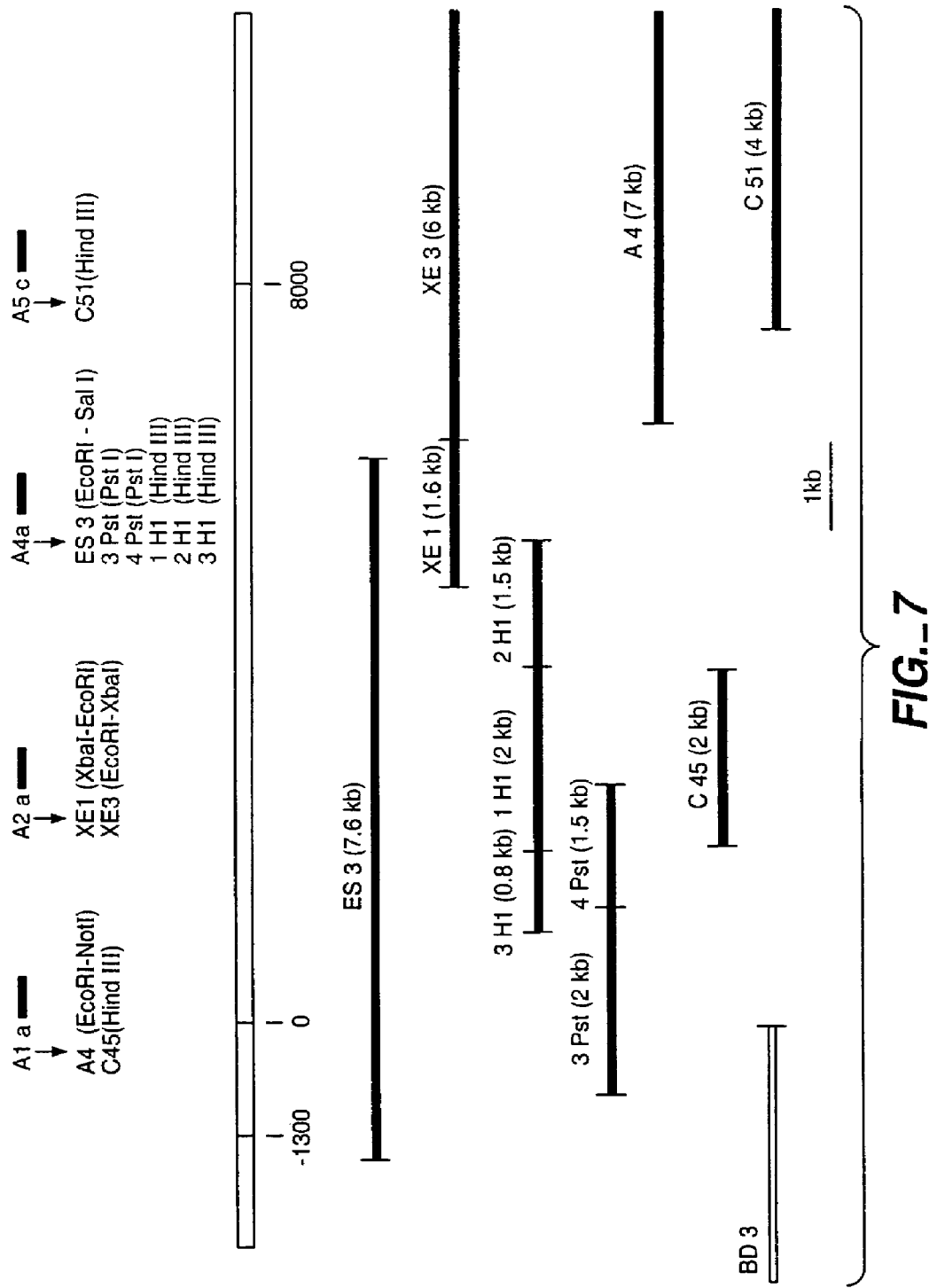
FIG._7

MN GENE AND PROTEIN

This application is a continuation of U.S. Ser. No. 09/807,949 (filed Aug. 9, 2001), now U.S. Pat. No. 7,713,704, herein incorporated by reference, which is a national stage filing of PCT/US99/24879 (filed Oct. 22, 1999), and is a continuation-in-part of U.S. Ser. No. 09/177,776 (filed Oct. 23, 1998), now U.S. Pat. No. 6,297,051, and U.S. Ser. No. 09/178,115 (filed Oct. 23, 1998), now U.S. Pat. No. 6,297,041.

FIELD OF THE INVENTION

The present invention is in the general area of medical genetics and in the fields of biochemical engineering, immunochemistry and oncology. More specifically, it relates to the MN gene—a cellular gene considered to be an oncogene, which encodes the oncoprotein now known alternatively as the MN protein, the MN/CA IX isoenzyme or the MN/G250 protein.

REFERENCE TO SEQUENCE LISTING

The Sequence Listing, filed electronically and identified as U.S. Ser. No. 11/939,351-SEQ-LISTING, was created on Feb. 21, 2008, is 78.9 kb in size and is hereby incorporated by reference.

BACKGROUND OF THE INVENTION

Zavada et al., International Publication Number WO 93/18152 (published 16 Sep. 1993) and U.S. Pat. No. 5,387,676 (issued Feb. 7, 1996), describe the elucidation of the biological and molecular nature of MaTu which resulted in the discovery of the MN gene and protein. The MN gene was found to be present in the chromosomal DNA of all vertebrates tested, and its expression to be strongly correlated with tumorigenicity.

The MN protein was first identified in HeLa cells, derived from a human carcinoma of cervix uteri. It is found in many types of human carcinomas (notably uterine cervical, ovarian, endometrial, renal, bladder, breast, colorectal, lung, esophageal, and prostate, among others). Very few normal tissues have been found to express MN protein to any significant degree. Those MN-expressing normal tissues include the human gastric mucosa and gallbladder epithelium, and some other normal tissues of the alimentary tract. Paradoxically, MN gene expression has been found to be lost or reduced in carcinomas and other preneoplastic/neoplastic diseases in some tissues that normally express MN, e.g., gastric mucosa.

In general, oncogenesis may be signified by the abnormal expression of MN protein. For example, oncogenesis may be signified: (1) when MN protein is present in a tissue which normally does not express MN protein to any significant degree; (2) when MN protein is absent from a tissue that normally expresses it; (3) when MN gene expression is at a significantly increased level, or at a significantly reduced level from that normally expressed in a tissue; or (4) when MN protein is expressed in an abnormal location within a cell.

Zavada et al., WO 93/18152 and Zavada et al., WO 95/34650 (published 21 Dec. 1995) disclose how the discovery of the MN gene and protein and the strong association of MN gene expression and tumorigenicity led to the creation of methods that are both diagnostic/prognostic and therapeutic for cancer and precancerous conditions. Methods and compositions were provided therein for identifying the onset and presence of neoplastic disease by detecting and detecting or quantitating abnormal MN gene expression in vertebrates.

Abnormal MN gene expression can be detected or detected and quantitated by a variety of conventional assays in vertebrate samples, for example, by immunoassays using MN-specific antibodies to detect or detect and quantitate MN antigen, by hybridization assays or by PCR assays, such as RT-PCR, using MN nucleic acids, such as, MN cDNA, to detect or detect and quantitate MN nucleic acids, such as, MN mRNA.

Zavada et al, WO 93/18152 and WO 95/34650 describe the production of MN-specific antibodies. A representative and preferred MN-specific antibody, the monoclonal antibody M75 (Mab M75), was deposited at the American Type Culture Collection (ATCC) in Manassus, Va. (USA) under ATCC Number HB 11128. The M75 antibody was used to discover and identify the MN protein and can be used to identify readily MN antigen in Western blots, in radioimmunoassays and immunohistochemically, for example, in tissue samples that are fresh, frozen, or formalin-, alcohol-, acetone- or otherwise fixed and/or paraffin-embedded and deparaffinized. Another representative and preferred MN-specific antibody, Mab MN12, is secreted by the hybridoma MN 12.2.2, which was deposited at the ATCC under the designation HB 11647. Example 1 of Zavada et al., WO 95/34650 provides representative results from immunohistochemical staining of tissues using MAb M75, which results support the designation of the MN gene as an oncogene.

Many studies have confirmed the diagnostic/prognostic utility of MN. The following articles discuss the use of the MN-specific MAb M75 in diagnosing/prognosing precancerous and cancerous cervical lesions: Leff, D. N., "Half a Century of HeLa Cells: Transatlantic Antigen Enhances Reliability of Cervical Cancer Pap Test, Clinical Trials Pending," *BioWorld® Today: The Daily Biotechnology Newspaper*, 9(55) (Mar. 24, 1998); Stanbridge, E. J., "Cervical marker can help resolve ambiguous Pap smears," *Diagnostics Intelligence*, 10(5): 11 (1998); Liao and Stanbridge, "Expression of the MN Antigen in Cervical Papanicolaou Smears is an Early Diagnostic Biomarker of Cervical Dysplasia," *Cancer Epidemiology, Biomarkers & Prevention*, 5: 549-557 (1996); Brewer et al., "A Study of Biomarkers in Cervical Carcinoma and Clinical Correlation of the Novel Biomarker MN," *Gynecologic Oncology*, 63: 337-344 (1996); and Liao et al., "Identification of the MN Antigen as a Diagnostic Biomarker of Cervical Intraepithelial Squamous and Glandular Neoplasia and Cervical Carcinomas," *American Journal of Pathology*, 145(3): 598-609 (1994).

Premalignant and Malignant Colorectal Lesions. MN has been detected in normal gastric, intestinal, and biliary mucosa. [Pastorekova et al., *Gastroenterology*, 112: 398-408 (1997).] Immunohistochemical analysis of the normal large intestine revealed moderate staining in the proximal colon, with the reaction becoming weaker distally. The staining was confined to the basolateral surfaces of the cryptal epithelial cells, the area of greatest proliferative capacity. As MN is much more abundant in the proliferating cryptal epithelium than in the upper part of the mucosa, it may play a role in control of the proliferation and differentiation of intestinal epithelial cells. Cell proliferation increases abnormally in premalignant and malignant lesions of the colorectal epithelium, and therefore, is considered an indicator of colorectal tumor progression. [Risio, M., *J. Cell Biochem*, 16G: 79-87 (1992); and Moss et al., *Gastroenterology*, 111: 1425-1432 (1996).]

The MN protein is now considered to be the first tumor-associated carbonic anhydrase (CA) isoenzyme that has been described. Carbonic anhydrases (CAs) form a large family of genes encoding zinc metalloenzymes of great physiological importance. As catalysts of reversible hydration of carbon dioxide, these enzymes participate in a variety of biological processes, including respiration, calcification, acid-base balance, bone resorption, formation of aqueous humor, cerebrospinal fluid, saliva and gastric acid [reviewed in Dodgson et al., *The Carbonic Anhydrases*, Plenum Press, New York-London, pp. 398 (1991)]. CAs are widely distributed in different living organisms.

In mammals, at least seven isoenzymes (CA I-VII) and a few CA-related proteins (CARP/CA VIII, RPTP-β, RPTP-τ) had been identified [Hewett-Emmett and Tashian, *Mol. Phyl. Evol.*, 5: 50-77 (1996)], when analysis of the MN deduced amino acid sequence revealed a striking homology between the central part of the MN protein and carbonic anhydrases, with the conserved zinc-binding site as well as the enzyme's active center. Then MN protein was found to bind zinc and to have CA activity. Based on that data, the MN protein is now considered to be the ninth carbonic anhydrase isoenzyme MN/CA IX. [Opavsky et al., *Genomics*, 33: 480-487 (May 1996)]. [See also, Hewett-Emmett, supra, wherein CA IX is suggested as a nomenclatural designation.]

CAs and CA-related proteins show extensive diversity in both their tissue distribution and in their putative or established biological functions [Tashian, R. E., *Adv. in Genetics*, 30: 321-356 (1992)]. Some of the CAs are expressed in almost all tissues (CA II), while the expression of others appears to be more restricted (CA VI and CA VII in salivary glands). In cells, they may reside in the cytoplasm (CA I, CA II, CA III, and CA VII), in mitochondria (CA V), in secretory granules (CA VI), or they may associate with membrane (CA IV). Occasionally, nuclear localization of some isoenzymes has been noted [Parkkila et al., *Gut*, 35: 646-650 (1994); Parkkilla et al., *Histochem. J.*, 27: 133-138 (1995); Mori et al., *Gastroenterol.*, 105: 820-826 (1993)].

The CAs and CA-related proteins also differ in kinetic properties and susceptibility to inhibitors [Sly and Hu, *Annu. Rev. Biochem.*, 64: 375-401 (1995)]. In the alimentary tract, carbonic anhydrase activity is involved in many important functions, such as saliva secretion, production of gastric acid, pancreatic juice and bile, intestinal water and ion transport, fatty acid uptake and biogenesis in the liver. At least seven CA isoenzymes have been demonstrated in different regions of the alimentary tract. However, biochemical, histochemical and immunocytochemical studies have revealed a considerable heterogeneity in their levels and distribution [Swensen, E. R., "Distribution and functions of carbonic anhydrase in the gastrointestinal tract," In: *The Carbonic Anhydrases. Cellular Physiology and Molecular Genetics*, (Dodgson et al. eds.) Plenum Press, New York, pages 265-287 (1991); and Parkkila and Parkkila, *Scan J. Gastroenterol.*, 31: 305-317 (1996)]. While CA II is found along the entire alimentary canal, CA IV is linked to the lower gastrointestinal tract, CA I, III and V are present in only a few tissues, and the expression of CA VI and VII is restricted to salivary glands [Parkkila et al., *Gut*, 35: 646-650 (1994); Fleming et al., *J. Clin. Invest.*, 96: 2907-2913 (1995); Parkkila et al., *Hepatology*, 24: 104 (1996)].

MN/CA IX has a number of properties that distinguish it from other known CA isoenzymes and evince its relevance to oncogenesis. Those properties include its density dependent expression in cell culture (e.g., HeLa cells), its correlation with the tumorigenic phenotype of somatic cell hybrids between HeLa and normal human fibroblasts, its close association with several human carcinomas and its absence from corresponding normal tissues [e.g., Zavada et al., *Int. J. Cancer*, 54: 268-274 (1993): Pastorekova et al., *Virology*, 187: 620-626 (1992); Liao et al., *Am. J. Pathol.*, 145: 598-609 (1994); Pastorek et al., *Oncogene*, 9: 2788-2888 (1994); Cote, *Women's Health Weekly: News Section*, p. 7 (Mar. 30, 1998); Liao et al., *Cancer Res.*, 57: 2827 (1997); Vermylen et al., "Expression of the MN antigen as a biomarker of lung carcinoma and associated precancerous conditions," *Proceedings AACR*, 39: 334 (1998); McKiernan et al., *Cancer Res.*, 57: 2362 (1997); and Turner et al., *Hum. Pathol.*, 28(6): 740 (1997)]. In addition, the in vitro transformation potential of MN/CA IX cDNA has been demonstrated in NIH 3T3 fibroblasts [Pastorek et al., id.].

The MN protein has also been identified with the G250 antigen. Uemura et al., "Expression of Tumor-Associated Antigen MN/G250 in Urologic Carcinoma: Potential Therapeutic Target," *J. Urol.*, 157 (4 Suppl.): 377 (Abstract 1475; 1997) states: "Sequence analysis and database searching revealed that G250 antigen is identical to MN, a human tumor-associated antigen identified in cervical carcinoma (Pastorek et al., 1994)."

SUMMARY OF THE INVENTION

Identified herein is the location of the MN protein binding site. Of particular importance is the region within the proteoglycan-like domain, aa 61-96 (SEQ ID NO: 97) which contains a 6-fold tandem repeat of 6 amino acids, and within which the epitope for the M75 MAb resides in at least two copies, and within which the MN binding site is considered to be located. An alternative MN binding site may be located in the CA domain.

Also identified are MN proteins and MN polypeptides that compete for attachment to cells with immobilized MN protein. Such MN proteins/polypeptides prevent cell-cell adhesion and the formation of intercellular contacts.

Disclosed herein are cell adhesion assay methods that are used to identify binding site(s) on the MN protein to which vertebrate cells, preferably mammalian cells, more preferably human cells, bind. Such a MN binding site is then identified as a therapeutic target which can be blocked with MN-specific antibodies, or inorganic or organic molecules, preferably organic molecules, more preferably proteins/polypeptides that specifically bind to said site.

Further disclosed are therapeutic methods to treat patients with preneoplastic/neoplastic disease associated with or characterized by abnormal MN expression, which methods are based on blocking said MN binding site with molecules, inorganic or organic, but preferably organic molecules, more preferably proteins/polypeptides, that bind specifically to said binding site. The growth of a vertebrate preneoplastic/neoplastic cell that abnormally expresses MN protein can be inhibited by administering such organic or inorganic molecules, preferably organic molecules, more preferably proteins/polypeptides in a therapeutically effective amount in a physiologically acceptable formulation. Such a preferred therapeutic protein/polypeptide is herein considered to comprise an amino acid sequence selected from the group consisting of SEQ ID NOS: 107-109. Such heptapeptides are considered to be comprised by MN protein partner(s). Blocking the interaction between MN protein and its binding partner(s), is expected to lead to a decrease of tumor growth.

Further provided are other therapeutic methods wherein the growth of a vertebrate, preferably mammalian, more preferably human, preneoplastic or neoplastic cell that abnormally expresses MN protein is inhibited. Said methods comprise transfecting said cell with a vector comprising an expression control sequence operatively linked to a nucleic acid encoding the variable domains of an MN-specific antibody, wherein said domains are separated by a flexible linker peptide, preferably SEQ ID NO: 116. Preferably said expression control sequence comprises the MN gene promoter.

Still further therapeutic methods comprise transfecting said cell with a vector comprising a nucleic acid that encodes a cytotoxic protein/polypeptide, such as HSVtk, operatively linked to the MN gene promoter. Such a therapeutic vector may also comprise a nucleic acid encoding a cytokine, such as, IL-2 or IFN.

Aspects of the instant invention disclosed herein are described in more detail as follows. The therapeutic use of organic or inorganic molecules, preferably organic molecules, is disclosed. Preferred such molecules bind specifically to a site on MN protein to which vertebrate cells adhere in a cell adhesion assay, wherein said molecule when tested in vitro inhibits the adhesion of cells to MN protein. Further preferred are such molecules, which when in contact with a vertebrate preneoplastic or neoplastic cell that abnormally expresses MN protein, inhibit the growth of said cell. Said vertebrate cells are preferably mammalian and more preferably human.

Preferably such a molecule is organic, and more preferably such a organic molecule is a protein or a polypeptide. Still further preferably, said protein or polypeptide comprises an amino acid sequence selected from the group consisting of SEQ ID NOS: 107, 108, 109, 137 and 138. Even more preferably, said polypeptide is selected from the group consisting of SEQ ID NOS: 107, 108, 109, 137 and 138.

The site on MN proteins to which vertebrate cells adhere in said cell adhesion assay is preferably within the proteoglycan-like domain [SEQ ID NO: 50] or within the carbonic anhydrase domain [SEQ ID NO: 51] of the MN protein. Preferably that site comprises an amino acid sequence selected from the group consisting of SEQ ID NOS: 10 and 97-106. Still further preferably, that site has an amino acid sequence selected from the group consisting of SEQ ID NOS: 10 and 97-106.

Another aspect of this invention concerns MN proteins and MN polypeptides which mediate attachment of vertebrate cells in a cell adhesion assay, wherein said MN protein or MN polypeptide when introduced into the extracellular fluid environment of vertebrate cells prevents the formation of intercellular contacts and the adhesion of said vertebrate cells to each other. Such MN proteins and MN polypeptides may be useful to inhibit the growth of vertebrate preneoplastic or neoplastic cells that abnormally express MN protein, when such MN proteins or MN polypeptides are introduced into the extracellular fluid environment of such vertebrate cells. Said vertebrate cells are preferably mammalian, and more preferably human.

Said MN proteins or MN polypeptides which mediate attachment of vertebrate cells in a cell adhesion assay, preferably have amino acid sequences from SEQ ID NO: 97, from SEQ ID NO: 50, or from SEQ ID NO: 51, more preferably from SEQ ID NO: 50. Still more preferably such MN proteins or MN polypeptides comprise amino acid sequences selected from the group consisting of SEQ ID NOS: 10 and 97-106. Alternatively, said MN polypeptides are selected from the group consisting of SEQ ID NOS: 10 and 97-106.

Representative MN proteins and MN polypeptides which mediate attachment of vertebrate cells in a cell adhesion assay, are specifically bound by either the M75 monoclonal antibody that is secreted from the hybridoma VU-M75, which was deposited at the American Type Culture Collection under ATCC No. HB 11128, or by the MN12 monoclonal antibody that is secreted from the hybridoma MN 12.2.2, which was deposited at the American Type Culture Collection under ATCC No. HB 11647, or by both said monoclonal antibodies.

Another aspect of the instant invention is a method of identifying a site on an MN protein to which vertebrate cells adhere by testing a series of overlapping polypeptides from said MN protein in a cell adhesion assay with vertebrate cells, and determining that if cells adhere to a polypeptide from said series, that said polypeptide comprises a site on said MN protein to which vertebrate cells adhere.

Still another aspect of the instant invention is a vector comprising an expression control sequence operatively linked to a nucleic acid encoding the variable domains of a MN-specific antibody, wherein said domains are separated by a flexible linker polypeptide, and wherein said vector, when transfected into a vertebrate preneoplastic or neoplastic cell that abnormally expresses MN protein, inhibits the growth of said cell. Preferably said expression control sequence comprises the MN gene promoter operatively linked to said nucleic acid. Further preferably, said flexible linker polypeptide has the amino acid sequence of SEQ ID NO: 116, and even further preferably, said MN gene promoter has the nucleotide sequence of SEQ ID NO: 27.

Another further aspect of the instant invention concerns a vector comprising a nucleic acid that encodes a cytotoxic protein or cytotoxic polypeptide operatively linked to the MN gene promoter, wherein said vector, when transfected into a vertebrate preneoplastic or neoplastic cell that abnormally expresses MN protein, inhibits the growth of said cell. In one preferred embodiment said cytotoxic protein is HSV thymidine kinase. Preferably, said vector further comprises a nucleic acid encoding a cytokine operatively linked to said MN gene promoter. In alternative and preferred embodiments, said cytokine is interferon or interleukin-2.

The MN gene promoter is characterized herein. The identification of the binding site for a repressor of MN transcription is disclosed. Mutational analysis indicated that the direct repeat AGGGCacAGGGC [SEQ ID NO: 143] is required for efficient repressor binding.

Identification of the protein that binds to the repressor and modification of its binding properties is another route to modulate MN expression leading to cancer therapies. Suppression of MN expression in tumor cells by over expression of a negative regulator is expected to lead to a decrease of tumor growth. A repressor complex comprising at least two subunits was found to bind to SEQ ID NO: 115 of the MN gene promoter. A repressor complex, found to be in direct contact with SEQ ID NO: 115 by UV crosslinking, comprised two proteins having molecular weights of 35 and 42 kilodaltons, respectively.

ABBREVIATIONS

The following abbreviations are used herein:

| | |
|---|---|
| aa | amino acid |
| ATCC | American Type Culture Collection |
| bp | base pairs |
| BLV | bovine leukemia virus |
| BSA | bovine serum albumin |
| BRL | Bethesda Research Laboratories |
| CA | carbonic anhydrase |
| CAM | cell adhesion molecule |
| CARP | carbonic anhydrase related protein |
| CAT | chloramphenicol acetyltransferase |
| Ci | curie |
| cm | centimeter |
| CMV | cytomegalovirus |
| cpm | counts per minute |
| C-terminus | carboxyl-terminus |

| | -continued |
|---|---|
| CTL | cytotoxic T lymphocytes |
| °C. | degrees centigrade |
| DEAE | diethylaminoethyl |
| DMEM | Dulbecco modified Eagle medium |
| ds | double-stranded |
| EDTA | ethylenediaminetetraacetate |
| EGF | epidermal growth factor |
| EIA | enzyme immunoassay |
| ELISA | enzyme-linked immunosorbent assay |
| EMSA | electrophoretic mobility shift assay |
| F | fibroblasts |
| FACS | cytofluorometric study |
| FCS | fetal calf serum |
| FITC | fluorescein isothiocyanate |
| FTP | DNase 1 footprinting analysis |
| GST-MN | fusion protein MN glutathione S-transferase |
| GVC | ganciclovir |
| H | HeLa cells |
| H-E | haematoxylin-eosin |
| HEF | human embryo fibroblasts |
| HeLa K | standard type of HeLa cells |
| HeLa S | Stanbridge's mutant HeLa D98/AH.2 |
| H/F-T | hybrid HeLa fibroblast cells that are tumorigenic; derived from HeLa D98/AH.2 |
| H/F-N | hybrid HeLa fibroblast cells that are nontumorigenic; derived from HeLa D98/AH.2 |
| HPV | Human papilloma virus |
| HRP | horseradish peroxidase |
| HSV | Herpes simplex virus |
| IC | intracellular |
| IFN | interferon |
| IL-2 | interleukin-2 |
| Inr | initiator |
| IPTG | isopropyl-beta-D-thiogalacto-pyranoside |
| kb | kilobase |
| kbp | kilobase pairs |
| kd or kDa | kilodaltons |
| KS | keratan sulphate |
| LCMV | lymphocytic choriomeningitis virus |
| LTR | long terminal repeat |
| M | molar |
| mA | milliampere |
| MAb | monoclonal antibody |
| MCSF | macrophage colony stimulating factor |
| ME | mercaptoethanol |
| MEM | minimal essential medium |
| min. | minute(s) |
| mg | milligram |
| ml | milliliter |
| mM | millimolar |
| MMC | mitomycin C |
| mmol | millimole |
| MLV | murine leukemia virus |
| N | normal concentration |
| NEG | negative |
| ng | nanogram |
| nm | nanometer |
| nt | nucleotide |
| N-terminus | amino-terminus |
| ODN | oligodeoxynucleotide |
| ORF | open reading frame |
| PA | Protein A |
| PBS | phosphate buffered saline |
| PCR | polymerase chain reaction |
| PEST | combination of one-letter abbreviations for proline, glutamic acid, serine, threonine |
| PG | proteoglycan |
| pI | isoelectric point |
| PMA | phorbol 12-myristate 13-acetate |
| POS | positive |
| Py | pyrimidine |
| RACE | rapid amplification of cDNA ends |
| RCC | renal cell carcinoma |
| RIA | radioimmunoassay |
| RIP | radioimmunoprecipitation |
| RIPA | radioimmunoprecipitation assay |
| RNP | RNase protection assay |
| RT-PCT | reverse transcription polymerase chain reaction |
| SAC | *Staphylococcus aureus* cells |
| *S. aureus* | *Staphylococcus aureus* |

| | -continued |
|---|---|
| sc | subcutaneous |
| SDRE | serum dose response element |
| SDS | sodium dodecyl sulfate |
| SDS-PAGE | sodium dodecyl sulfate-polyacrylamide gel electrophoresis |
| SINE | short interspersed repeated sequence |
| SP | signal peptide |
| SP-RIA | solid-phase radioimmunoassay |
| SSDS | synthetic splice donor site |
| SSH | subtractive suppressive PCR |
| SSPE | NaCl (0.18M), sodium phosphate (0.01M), EDTA (0.001M) |
| TBE | Tris-borate/EDTA electrophoresis buffer |
| TC | tissue culture |
| TCA | trichloroacetic acid |
| TC media | tissue culture media |
| TC | tissue culture |
| tk | thymidine kinase |
| TM | transmembrane |
| TMB | tetramethylbenzidine |
| Tris | tris (hydroxymethyl) aminomethane |
| μCi | microcurie |
| μg | microgram |
| μl | microliter |
| μM | micromolar |
| VSV | vesicular stomatitis virus |
| VV | vaccinia virus |
| X-MLV | xenotropic murine leukemia virus |

| Cell Lines | |
|---|---|
| AGS | cell line derived from a primary adenogastric carcinoma [Barranco and Townsend, Cancer Res., 43: 1703 (1983) and Invest. New Drugs, 1: 117 (1983)]; available from the ATCC under CRL-1739; |
| BL-3 | bovine B lymphocytes [ATCC CRL-8037; leukemia cell suspension; J. Natl. Cancer Inst. (Bethesda) 40: 737 (1968)]; |
| C33 | a cell line derived from a human cervical carcinoma biopsy [Auersperg, N., J. Nat'l. Cancer Inst. (Bethesda), 32: 135-148 (1964)]; available from the ATCC under HTB-31; |
| C33A | human cervical carcinoma cells [ATCC HTB-31; J. Natl. Cancer Inst. (Bethesda) 32: 135 (1964)]; |
| COS | simian cell line [Gluzman, Y., Cell, 23: 175 (1981)]; |
| HeLa K | standard type of HeLa cells; aneuploid, epithelial-like cell line isolated from a human cervical adenocarcinoma [Gey et al., Cancer Res., 12: 264 (1952); Jones et al., Obstet. Gynecol., 38: 945-949 (1971)] obtained from Professor B. Korych, [Institute of Medical Microbiology and Immunology, Charles University; Prague, Czech Republic]; |
| HeLa D98/AH.2 (also HeLa s) | Mutant HeLa clone that is hypoxanthine guanine phosphoribosyl transferase-deficient (HGPRT') kindly provided by Eric J. Stanbridge [Department of Microbiology, College of Medicine, University of California, Irvine, CA (USA) and reported in Stanbridge et al., Science, 215: 252-259 (15 Jan. 1982); parent of hybrid cells H/F-N and H/F-T, also obtained from E.J. Stanbridge; |
| KATO III | cell line prepared from a metastatic form of a gastric carcinoma [Sekiguichi et al., Japan J. Exp. Med., 48: 61 (1978)]; available from the ATCC under HTB-103; |
| NIH-3T3 | murine fibroblast cell line reported in Aaronson, Science, 237: 178 (1987). |
| QT35 | quail fibrosarcoma cells [ECACC: 93120832; Cell, 11: 95 (1977)]; |
| Raj | human Burkitt's lymphoma cell line [ATCC CCL-86; Lancet, 1: 238 (1964)]; |
| Rat2TK | cell line (rat embryo, thymidine kinase mutant) was derived from a subclone of a 5'-bromo-deoxyuridine resistant strain of the Fischer rat fibroblast 3T3-like cell line Rat1; the cells lack appreciable levels of nuclear thymidine kinase [Ahrens, B., Virology, 113: 408 (1981)]; |
| SiHa | human cervical squamous carcinoma cell line [ATCC HTB-35; Friedl et al., Proc. Soc. Exp. Biol. Med., 135: 543 (1990)]; |

-continued

| Cell Lines | |
|---|---|
| XC | cells derived from a rat rhabdomyosarcoma induced with Rous sarcoma virus-induced rat sarcoma [Svoboda, J., Natl. Cancer Center Institute Monograph No. 17, IN: "International Conference on Avian Tumor Viruses" (J.W. Beard ed.), pp. 277-298 (1964)], kindly provided by Jan Svoboda [Institute of Molecular Genetics, Czechoslovak Academy of Sciences; Prague, Czech Republic]; and |
| CGL1 | H/F-N hybrid cells (HeLa D98/AH.2 derivative); |
| CGL2 | H/F-N hybrid cells (HeLa D98/AH.2 derivative); |
| CGL3 | H/F-T hybrid cells (HeLa D98/AH.2 derivative); |
| CGL4 | H/F-T hybrid cells (HeLa D98/Ah.2 derivative). |

Nucleotide and Amino Acid Sequence Symbols

The following symbols are used to represent nucleotides herein:

| Base Symbol | Meaning |
|---|---|
| A | adenine |
| C | cytosine |
| G | guanine |
| T | thymine |
| U | uracil |
| I | inosine |
| M | A or C |
| R | A or G |
| W | A or T/U |
| S | C or G |
| Y | C or T/U |
| K | G or T/U |
| V | A or C or G |
| H | A or C or T/U |
| D | A or G or T/U |
| B | C or G or T/U |
| N/X | A or C or G or T/U |

There are twenty main amino acids, each of which is specified by a different arrangement of three adjacent nucleotides (triplet code or codon), and which are linked together in a specific order to form a characteristic protein. A three-letter or one-letter convention is used herein to identify said amino acids, as, for example, in FIG. 1 as follows:

| Amino acid name | 3 Ltr. Abbrev. | 1 Ltr. Abbrev. |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Unknown or other | | X |

BRIEF DESCRIPTION OF THE FIGURES

FIG. 1A-C provides the nucleotide sequence for a MN cDNA [SEQ ID NO: 1] clone isolated as described herein. FIG. 1A-C also sets forth the predicted amino acid sequence [SEQ ID NO: 2] encoded by the cDNA.

FIG. 2A-F provides a 10,898 bp complete genomic sequence of MN [SEQ ID NO: 5]. The base count is as follows: 2654 A; 2739 C; 2645 G; and 2859 T. The 11 exons are in general shown in capital letters, but exon 1 is considered to begin at position 3507 as determined by RNase protection assay.

FIG. 3 is a restriction map of the full-length MN cDNA. The open reading frame is shown as an open box. The thick lines below the restriction map illustrate the sizes and positions of two overlapping cDNA clones. The horizontal arrows indicate the positions of primers R1 [SEQ ID NO: 7] and R2 [SEQ ID NO: 8] used for the 5' end RACE. Relevant restriction sites are BamHI (B). EcoRV (V), EcoRI (E), PstI (Ps), PvuII (Pv).

FIG. 4 schematically represents the 5' MN genomic region of a MN genomic clone wherein the numbering corresponds to transcription initiation sites estimated by RACE.

FIG. 5 provides an exon-intron map of the human MN/CA IX gene. The positions and sizes of the exons (numbered, cross-hatched boxes), Alu repeat elements (open boxes) and an LTR-related sequence (first unnumbered stippled box) are adjusted to the indicated scale. The exons corresponding to individual MN/CA IX protein domains are enclosed in dashed frames designated PG (proteoglycan-like domain), CA (carbonic anhydrase domain), TM (transmembrane anchor) and IC (intracytoplasmic tail). Below the map, the alignment of amino acid sequences illustrates the extent of homology between the MN/CA IX protein PG region (aa 53-111) [SEQ ID NO: 50] and the human aggrecan (aa 781-839) [SEQ ID NO: 54].

FIG. 6 is a nucleotide sequence for the proposed promoter of the human MN gene [SEQ ID NO: 27]. The nucleotides are numbered from the transcription initiation site according to RNase protection assay. Potential regulatory elements are overlined. Transcription start sites are indicated by asterisks (RNase protection) and dots (RACE) above the corresponding nucleotides. The sequence of the 1st exon begins under the asterisks. FTP analysis of the MN4 promoter fragment revealed 5 regions (I-V) protected at both the coding and noncoding strands, and two regions (VI and VII) protected at the coding strand but not at the noncoding strand.

FIG. 7 provides a schematic of the alignment of MN genomic clones according to their position related to the transcription initiation site. All the genomic fragments except Bd3 were isolated from a lambda FIX II genomic library derived from HeLa cells. Clone Bd3 was derived from a human fetal brain library.

FIG. 8 schematically represents the MN protein structure. The abbreviations are the same as used in FIG. 5. The scale indicates the number of amino acids.

DETAILED DESCRIPTION

The terms "MN/CA IX" and "MN/CA9" are herein considered to be synonyms for MN. Also, the G250 antigen is considered to refer to MN protein/polypeptide. [Uemura et al., *J. Urol.*, 157 (4 Suppl.): 377 (Abstract 1475; 1997).]

MN/CA IX was first identified in HeLa cells, derived from human carcinoma of cervix uteri, as both a plasma membrane and nuclear protein with an apparent molecular weight of 58 and 54 kilodaltons (kDA) as estimated by Western blotting. It is N-glycosylated with a single 3 kDa carbohydrate chain and under non-reducing conditions forms S—S-linked oligomers [Pastorekova et al., *Virology*, 187: 620-626 (1992); Pastorek et al., *Oncogene*, 9: 2788-2888 (1994)]. MN/CA IX is a transmembrane protein located at the cell surface, although in some cases it has been detected in the nucleus [Zavada et al., *Int. J. Cancer*, 54: 268-274 (1993); Pastorekova et al., supra].

MN is manifested in HeLa cells by a twin protein, p54/58N. Immunoblots using a monoclonal antibody reactive with p54/58N (MAb M75) revealed two bands at 54 kDa and 58 kDa. Those two bands may correspond to one type of protein that most probably differs by post-translational processing. Herein, the phrase "twin protein" indicates p54/58N.

Zavada et al., WO 93/18152 and/or WO 95/34650 disclose the MN cDNA sequence (SEQ ID NO: 1) shown herein in FIG. 1A-1C, the MN amino acid sequence (SEQ ID NO: 2) also shown in FIG. 1A-1C, and the MN genomic sequence (SEQ ID NO: 5) shown herein in FIG. 2A-2F. The MN gene is organized into 11 exons and 10 introns.

The first thirty seven amino acids of the MN protein shown in FIG. 1A-1C is the putative MN signal peptide [SEQ ID NO: 6]. The MN protein has an extracellular domain [amino acids (aa) 38-414 of FIG. 1A-1C (SEQ ID NO: 87)], a transmembrane domain [aa 415-434 (SEQ ID NO: 52)] and an intracellular domain [aa 435-459 (SEQ ID NO: 53)]. The extracellular domain contains the proteoglycan-like domain [aa 53-111 (SEQ ID NO: 50)] and the carbonic anhydrase (CA) domain [aa 135-391 (SEQ ID NO: 51].

Anticancer Drugs and Antibodies that Block Interaction of MN Protein and Receptor Molecules MN protein is considered to be a uniquely suitable target for cancer therapy for a number of reasons including the following. (1) It is localized on the cell surface, rendering it accessible. (2) It is expressed in a high percentage of human carcinomas (e.g., uterine cervical, renal, colon, breast, esophageal, lung, head and neck carcinomas, among others), but is not normally expressed to any significant extent in the normal tissues from which such carcinomas originate.

(3) It is normally expressed only in the stomach mucosa and in some epithelia of the digestive tract (epithelium of gallbladder and small intestine). An anatomic barrier thereby exists between the MN-expressing preneoplastic/neoplastic and MN-expressing normal tissues. Drugs, including antibodies, can thus be administered which can reach tumors without interfering with MN-expressing normal tissues.

(4) MAb M75 has a high affinity and specificity to MN protein. (5) MN cDNA and MN genomic clones which encompass the protein-coding and gene regulatory sequences have been isolated. (6) MN-specific antibodies have been shown to have among the highest tumor uptakes reported in clinical studies with antitumor antibodies in solid tumors, as shown for the MN-specific chimeric antibody G250 in animal studies and in phase I clinical trials with renal carcinoma patients. [Steffens et al., *J. Clin. Oncol.*, 15: 1529 (1997).] Also, MN-specific antibodies have low uptake in normal tissues.

Data, e.g. as presented herein, are consistent with the following theory concerning how MN protein acts in normal tissues and in preneoplastic/neoplastic tissues. In normal tissues (e.g., in stomach mucosa), MN protein is considered to be a differentiation factor. It binds with its normal receptor S (for stomach). Stomach carcinomas have been shown not to contain MN protein.

Ectopic expression of MN protein in other tissues causes malignant conversion of cells. Such ectopic expression is considered to be caused by the binding of MN protein with an alternative receptor H (for HeLa cells), coupled to a signal transduction pathway leading to malignancy. Drugs or antibodies which block the binding site of MN protein for receptor H would be expected to cause reversion of preneoplastic/neoplastic cells to normal or induce their death.

Design and Development of MN-Blocking Drugs or Antibodies

A process to design and develop MN-blocking drugs, e.g., peptides with high affinity to MN protein, or antibodies, has several steps. First, is to test for the binding of MN protein to receptors based on the cell adhesion assay described infra. That same procedure would also be used to assay for drugs blocking the MN protein binding site. In view of the alternative receptors S and H, stomach epithelial cells or revertants (containing preferentially S receptors), HeLa cells (containing the H receptor and lacking the S receptor) would be used in the cell adhesion assay.

To identify the receptor binding site of MN protein, deletion variants of MN protein lacking different domains can be used to identify region(s) responsible for interaction of MN protein with a receptor. Example 2 identifies and illustrates how to detect other binding sites on MN protein. A preferred MN binding site is considered to be closely related or identical to the epitope for MAb M75, which is located in at least 2 copies within the 6-fold tandem repeat of 6 amino acids [aa 61-96 (SEQ ID NO: 97)] in the proteoglycan-like domain of the MN protein. Smaller deletion variants can be prepared within that relevant domain, e.g., fusion proteins with only small segments of MN protein can be prepared. Also, controlled digestion of MN protein with specific proteases followed by separation of the products can be performed.

Further, peptides comprising the expected binding site can be synthesized. All of those products can be tested in cell adhesion assays, as exemplified below. [See, e.g., Pierschbacher and Ruoslahti, *PNAS*, 81:5985 (1984); Ruoslahti and Pierschbacher, *Science*, 238: 491.]

Molecules can be constructed to block the MN receptor binding site. For example, use of a phage display peptide library kit [as Ph.D®-7 Peptide 7-Mer Library Kit from New England Biolabs; Beverly, Mass. (USA)] as exemplified in Examples 2 and 3, can be used to find peptides with high affinity to the target molecules. Biologic activity of the identified peptides will be tested in vitro by inhibition of cell adhesion to MN protein, by effects on cell morphology and growth characteristics of MN-related tumor cells (HeLa) and of control cells, [Symington, *J. Biol. Chem.*, 267: 25744 (1992).] In vivo screening will be carried out in nude mice that have been injected with HeLa cells.

Peptides containing the binding site of the MN protein will be prepared [e.g. MAPs (multiple antigen peptides); Tam, J. P., *PNAS* (USA) 85: 5409 (1988); Butz et al., *Peptide Res.*, 7: 20 (1994)]. The MAPs will be used to immunize animals to obtain antibodies (polyclonal and/or monoclonal) that recognize and block the binding site. [ee, e.g., Brooks et al., *Cell*, 79: 1157 (1994).] "Vaccination" would then be used to test for protection in animals. Antibodies to the MN binding site could potentially be used to block MN protein's interaction(s) with other molecules.

Computer modeling can also be used to design molecules with specific affinity to MN protein that would mediate steric inhibition between MN protein and its receptor. A computer model of the MN binding site for the receptor will contain spatial, electrostatic, hydrophobic and other characteristics of this structure. Organic molecules complementary to the structure, that best fit into the binding site, will be designed. Inorganic molecules can also be similarly tested that could block the MN binding site.

The use of oncoproteins as targets for developing new cancer therapeutics is considered conventional by those of skill in the art. [See, e.g., Mendelsohn and Lippman, "Growth Factors," pp. 114-133, IN: DeVita et al. (eds.), *Cancer: Principles and Practice of Oncology* (4th Ed.; Lippincott; Philadelphia, 1993).] In its broadest sense, the design of blocking drugs can be based in competitive inhibition experiments. Such experiments have been used to invent drugs since the discovery of sulfonamides (competitive inhibitors of para-aminobenzoic acid, a precursor of folic acid). Also, some cytostatics are competitive inhibitors (e.g., halogenated pyrimidines, among others).

However, the application of such approaches to MN is new. In comparison to other tumor-related molecules (e.g. growth factors and their receptors), MN has the unique property of being differentially expressed in preneoplastic/neoplastic and normal tissues, which are separated by an anatomic barrier.

MN Gene—Cloning and Sequencing

FIG. 1A-C provides the nucleotide sequence for a full-length MN cDNA clone isolated as described below [SEQ ID NO: 1]. FIG. 2A-F provides a complete MN genomic sequence [SEQ ID NO: 5]. FIG. 6 shows the nucleotide sequence for a proposed MN promoter [SEQ ID NO: 27].

It is understood that because of the degeneracy of the genetic code, that is, that more than one codon will code for one amino acid [for example, the codons TTA, TTG, CTT, CTC, CTA and CTG each code for the amino acid leucine (leu)], that variations of the nucleotide sequences in, for example, SEQ ID NOS: 1 and 5 wherein one codon is substituted for another, would produce a substantially equivalent protein or polypeptide according to this invention. All such variations in the nucleotide sequences of the MN cDNA and complementary nucleic acid sequences are included within the scope of this invention.

It is further understood that the nucleotide sequences herein described and shown in FIGS. 1, 2 and 6, represent only the precise structures of the cDNA, genomic and promoter nucleotide sequences isolated and described herein. It is expected that slightly modified nucleotide sequences will be found or can be modified by techniques known in the art to code for substantially similar or homologous MN proteins and polypeptides, for example, those having similar epitopes, and such nucleotide sequences and proteins/polypeptides are considered to be equivalents for the purpose of this invention. DNA or RNA having equivalent codons is considered within the scope of the invention, as are synthetic nucleic acid sequences that encode proteins/polypeptides homologous or substantially homologous to MN proteins/polypeptides, as well as those nucleic acid sequences that would hybridize to said exemplary sequences [SEQ. ID. NOS. 1, 5 and 27] under stringent conditions, or that, but for the degeneracy of the genetic code would hybridize to said cDNA nucleotide sequences under stringent hybridization conditions. Modifications and variations of nucleic acid sequences as indicated herein are considered to result in sequences that are substantially the same as the exemplary MN sequences and fragments thereof.

Stringent hybridization conditions are considered herein to conform to standard hybridization conditions understood in the art to be stringent. For example, it is generally understood that stringent conditions encompass relatively low salt and/or high temperature conditions, such as provided by 0.02 M to 0.15 M NaCl at temperatures of 50° C. to 70° C. Less stringent conditions, such as, 0.15 M to 0.9 M salt at temperatures ranging from 20° C. to 55° C. can be made more stringent by adding increasing amounts of formamide, which serves to destabilize hybrid duplexes as does increased temperature.

Exemplary stringent hybridization conditions are described in Sambrook et al., *Molecular Cloning: A Laboratory Manual*, pages 1.91 and 9.47-9.51 (Second Edition, Cold Spring Harbor Laboratory Press; Cold Spring Harbor, N.Y.; 1989); Maniatis et al., *Molecular Cloning: A Laboratory Manual*, pages 387-389 (Cold Spring Harbor Laboratory; Cold Spring Harbor, N.Y.; 1982), Tsuchiya et al., *Oral Surgery, Oral Medicine, Oral Pathology*, 71(6): 721-725 (June 1991).

Zavada et al., WO 95/34650 described how a partial MN cDNA clone, a full-length MN cDNA clone and MN genomic clones were isolated and sequenced. Also, Zavada et al., *Int. J. Cancer*, 54: 268 (1993) describes the isolation and sequencing of a partial MN cDNA of 1397 bp in length. Briefly attempts to isolate a full-length clone from the original cDNA library failed. Therefore, the inventors performed a rapid amplification of cDNA ends (RACE) using MN-specific primers, R1 and R2 [SEQ ID NOS: 7 and 8], derived from the 5' region of the original cDNA clone. The RACE product was inserted into pBluescript, and the entire population of recombinant plasmids was sequenced with an MN-specific primer ODN1 [SEQ ID NO: 3]. In that way, a reliable sequence at the very 5' end of the MN cDNA as shown in FIG. 1 [SEQ ID NO: 1] was obtained.

Specifically, RACE was performed using 5' RACE System [GIBCO BRL; Gaithersburg, Md. (USA)] as follows. 1 µg of mRNA (the same as above) was used as a template for the first strand cDNA synthesis which was primed by the MN-specific antisense oligonucleotide, R1 (5'-TGGGGTTCTTGAG-GATCTCCAGGAG-3') [SEQ ID NO: 7]. The first strand product was precipitated twice in the presence of ammonium acetate and a homopolymeric C tail was attached to its 3' end by TdT. Tailed cDNA was then amplified by PCR using a nested primer, R2 (5'-CTCTAACTTCAGGGAGCCCTCT-TCTT-3') [SEQ ID NO: 8] and an anchor primer that anneals to the homopolymeric tail (5'-CUACUACUACUAGGC-CACGCGTCGAC TAGTACGGGI IGGGIIGGGIIG-3') [SEQ ID NO: 9]. The amplified product was digested with BamHI and SalI restriction enzymes and cloned into pBluescript II KS plasmid. After transformation, plasmid DNA was purified from the whole population of transformed cells and used as a template for sequencing with the MN-specific primer ODN1 [SEQ ID NO: 3; a 29-mer 5' CGC-CCAGTGGGTCATCTTCCCCAGAAGAG 3'].

To study MN regulation, MN genomic clones were isolated. One MN genomic clone (Bd3) was isolated from a human cosmid library prepared from fetal brain using both MN cDNA as a probe and the MN-specific primers derived from the 5' end of the cDNA ODN1 [SEQ ID NO: 3, supra] and ODN2 [SEQ. ID NO.: 4; 19-mer (5' GGAATCCTCCT-GCATCCGG 3')]. Sequence analysis revealed that that genomic clone covered a region upstream from a MN transcription start site and ending with the BamHI restriction site localized inside the MN cDNA. Other MN genomic clones can be similarly isolated.

FIG. 7 provides a schematic of the alignment of MN genomic clones according to the transcription initiation site. Plasmids containing the A4a clone and the XE1 and XE3 subclones were deposited at the American Type Culture Collection (ATCC) on Jun. 6, 1995, respectively under ATCC Deposit Nos. 97199, 97200, and 97198.

Exon-Intron Structure of Complete MN Genomic Region

The complete sequence of the overlapping clones contains 10,898 bp (SEQ ID NO: 5). FIG. 5 depicts the organization of the human MN gene, showing the location of all 11 exons as well as the 2 upstream and 6 intronic Alu repeat elements. All the exons are small, ranging from 27 to 191 bp, with the exception of the first exon which is 445 bp. The intron sizes range from 89 to 1400 bp. The CA domain is encoded by exons 2-8, while the exons 1, 10 and 11 correspond respectively to the proteoglycan-like domain, the transmembrane anchor and cytoplasmic tail of the MN/CA IX protein. Table 1 below lists the splice donor and acceptor sequences that conform to consensus splice sequences including the AG-GT motif [Mount, Nucleic Acids Res. 10: 459-472 (1982)].

TABLE 1

Exon-Intron Structure of the Human MN Gene

| Exon | Size | Genomic Position** | SEQ ID NO | 5'splice donor | SEQ ID NO |
|---|---|---|---|---|---|
| 1 | 445 | *3507-3951 | 28 | AGAAG gtaagt | 67 |
| 2 | 30 | 5126-5155 | 29 | TGGAG gtgaga | 68 |
| 3 | 171 | 5349-5519 | 30 | CAGTC gtgagg | 69 |
| 4 | 143 | 5651-5793 | 31 | CCGAG gtgagc | 70 |
| 5 | 93 | 5883-5975 | 32 | TGGAG gtacca | 71 |
| 6 | 67 | 7376-7442 | 33 | GGAAG gtcagt | 72 |
| 7 | 158 | 8777-8934 | 34 | AGCAG gtgggc | 73 |
| 8 | 145 | 9447-9591 | 35 | GCCAG gtacag | 74 |
| 9 | 27 | 9706-9732 | 36 | TGCTG gtgagt | 75 |
| 10 | 82 | 10350-10431 | 37 | CACAG gtatta | 76 |
| 11 | 191 | 10562-10752 | 38 | ATAAT end | |

| Intron | Size | Genomic Position** | SEQ ID NO | 3'splice acceptor | SEQ ID NO |
|---|---|---|---|---|---|
| 1 | 1174 | 3952-5125 | 39 | atacag GGGAT | 77 |
| 2 | 193 | 5156-5348 | 40 | ccccag GCGAC | 78 |
| 3 | 131 | 5520-5650 | 41 | acgcag TGCAA | 79 |
| 4 | 89 | 5794-5882 | 42 | tttcag ATCCA | 80 |
| 5 | 1400 | 5976-7375 | 43 | ccccag GAGGG | 81 |
| 6 | 1334 | 7443-8776 | 44 | tcacag GCTCA | 82 |
| 7 | 512 | 8935-9446 | 45 | ccctag CTCCA | 83 |
| 8 | 114 | 9592-9705 | 46 | ctccag TCCAG | 84 |
| 9 | 617 | 9733-10349 | 47 | tcgcag GTGACA | 85 |
| 10 | 130 | 10432-10561 | 48 | acacag AAGGG | 86 |

**positions are related to nt numbering in whole genomic sequence including the 5' flanking region [FIG. 2A-F]
*number corresponds to transcription initiation site determined below by RNase protection assay Mapping of MN Gene Transcription Initiation and Termination Sites Zavada et al., WO 95/34650 describes the process of mapping the MN gene transcription initiation and termination sites. A RNase protection assay was used for fine mapping of the 5' end of the MN gene. The probe was a uniformly labeled 470 nucleotide copy RNA (nt –205 to +265) [SEQ ID NO: 55], which was hybridized to total RNA from MN-expressing HeLa and CGL3 cells and analyzed on a sequencing gel. That analysis has shown that the MN gene transcription initiates at multiple sites, the 5' end of the longest MN transcript being 30 nt longer than that previously characterized by RACE.

Characterization of the 5'Flanking Region

The Bd3 genomic clone isolated from human fetal brain cosmid library was found to cover a region of 3.5 kb upstream from the transcription start site of the MN gene. It contains no significant coding region. Two Alu repeats are situated at positions –2587 to –2296 [SEQ ID NO: 56] and –1138 to –877 [SEQ ID NO: 57] (with respect to the transcription start determined by RNP).

Nucleotide sequence analysis of the DNA 5' to the transcription start (from nt –507) revealed no recognizable TATA box within the expected distance from the beginning of the first exon. However, the presence of potential binding sites for transcription factors suggests that this region might contain a promoter for the MN gene. There are several consensus sequences for transcription factors AP1 and AP2 as well as for other regulatory elements, including a p53 binding site [Locker and Buzard, J., DNA Sequencing and Mapping, 1: 3-11 (1990); Imagawa et al. Cell, 51: 251-260 (1987), El Deiry et al., Nat. Genet., 1: 44-49 (1992)]. Although the putative promoter region contains 59.3% C+G, it does not have additional attributes of CpG-rich islands that are typical for TATA-less promoters of housekeeping genes [Bird, Nature, 321: 209-213 (1986)]. Another class of genes lacking TATA box utilizes the initiator (Inr) element as a promoter. Many of these genes are not constitutively active, but they are rather regulated during differentiation or development. The Inr has a consensus sequence of PyPyPyCAPyPyPyPyPy [SEQ ID NO: 23] and encompasses the transcription start site [Smale and Baltimore, Cell, 57: 103-113 (1989)]. There are two such consensus sequences in the MN putative promoter; however, they do not overlap the transcription start (FIG. 6).

An interesting region was found in the middle of the MN gene. The region is about 1.4 kb in length [nt 4,600-6,000 of the genomic sequence; SEQ ID NO: 49] and spans from the 3' part of the 1st intron to the end of the 5th exon. The region has the character of a typical CpG-rich island, with 62.8% C+G content and 82 CpG: 131 GpC dinucleotides. Moreover, there are multiple putative binding sites for transcription factors AP2 and Sp1 [Locker and Buzard, supra; Briggs et al., Science, 234: 47-52 (1986)] concentrated in the center of this area. Particularly the 3rd intron of 131 bp in length contains three Sp1 and three AP2 consensus sequences. That data indicates the possible involvement of that region in the regulation of MN gene expression. However, functionality of that region, as well as other regulatory elements found in the proposed 5' MN promoter, remains to be determined.

MN Promoter

Study of the MN promoter has shown that it is TATA-less and contains regulatory sequences for AP-1, AP-2, as well as two p53 binding sites. The sequence of the 5' end of the 3.5 kb flanking region upstream of the MN gene has shown extensive homology to LTR of HERV-K endogenous retroviruses. Basal transcription activity of the promoter is very weak as proven by analyses using CAT and neo reporter genes. However, expression of the reporter genes is severalfold increased when driven from the 3.5 kb flanking region, indicating involvement of putative enhancers.

Functional characterization of the 3.5 kb MN 5' upstream region by deletion analysis lead to the identification of the [–173, +31] fragment [SEQ ID NO: 21] (also alternatively, but less preferably, the nearly identical –172, +31 fragment [SEQ ID NO: 91]) as the MN promoter. In vitro DNase I footprinting revealed the presence of five protected regions (PR) within the MN promoter. Detailed deletion analysis of the promoter identified PR 1 and 2 (numbered from the transcription start) as the most critical for transcriptional activity. PR4 [SEQ ID NO: 115] negatively affected transcription as its deletion led to increased promoter activity and was confirmed to function as a promoter-, position- and orientation-independent silencer element. Mutational analysis indicated that the direct repeat AGGGCacAGGGC [SEQ ID NO: 143] is required for efficient repressor binding. Two components of the repressor complex (35 and 42 kDa) were found to be in direct contact with PR4 by UV crosslinking. Increased cell density, known to induce MN expression, did not affect levels of PR4 binding in HeLa cells. Significantly reduced repressor level seems to be responsible for MN up-regulation in the case of tumorigenic CGL3 as compared to non-tumorigenic CGL1 HeLa×normal fibroblast hybrid cells.

Utility of MN Promoter as a Tumor-Specific Promoter for Gene Therapy

Being investigated is whether the MN gene promoter can be used as a tumor-specific promoter to drive the expression of a suicide gene [thymidine kinase (tk) of HSV)] and mediate the direct and bystander killing of tumor cells. HSVtk gene transferred to tumor cells converts nucleoside analogue ganciclovir (GCV) to toxic triphosphates and mediates the death of transduced and also neighboring tumor cells. The control of HSVtk by the MN gene promoter would allow its expression only in tumor cells, which are permissive for the biosynthesis of MN protein, and selectively kill such tumor cells, but not normal cells in which MN expression is repressed.

A plasmid construct in which HSVtk was cloned downstream of the MN promoter region Bd3, containing both proximal and distant regulatory elements of MN, was prepared. That plasmid pMN-HSVtk was transfected to Rat2TK- cells and C33 human cervical carcinoma cells using calcium phosphate precipitation and lipofection, respectively. Transfectants were tested for expression of HSVtk and GVC sensitivity. Analysis of the transfectants has shown the remarkable cytotoxic in vitro effect of GVC even in low concentrations (up to 95% of cells killed).

Polyclonal rabbit antiserum against HSVtk, using fusion protein with GST in pGEX-3X, has been prepared to immunodetect HSVtk synthesized in transfected cells. This model system is being studied to estimate the bystander effect, the inhibition of cloning efficiency and invasiveness of transduced and GVC-treated cells to collagen matrices. A recombinant retroviral vector with the MN promoter-driven HSVtk is to be prepared to test its in vivo efficacy using an animal model (e.g., SCID-mouse).

MN Promoter Analysis

Since the MN promoter is weak, a classical approach to study it would be limited due to the relatively low efficiency of transient transfections (up to 10%). Therefore, stable clonal cell lines expressing constructs containing the MN promoter fused to the CAT gene were prepared. In such clonal lines, 100% of the cells express the CAT gene driven from the MN promoter, and thus, the activity of the promoter is detectable easier than in transient experiments. Also, the promoter activity can be analysed repeatedly in the same cells under different conditions or treated by different factors and drugs. This approach allows for the study of the mechanisms underlying MN regulation at the level of transcription initiation.

Several types of transfections with promoter constructs linked to a reporter CAT gene (calcium precipitation, DEAE dextran combined with DMSO shock and/or chloroquine, as well as electroporation), different methods of CAT activity assay (scintillation method, thin layer chromatography) and several recipient cell lines differing in the level of MN expression and in transfection efficiency (HeLa, SiHa, CGL3, KATO III, Rat2TK⁻ and C33 cells). Activity of the MN promoter was detected preferably by the electroporation of CGL3 cells and thin layer chromatography. Further preferably, C33 cells cotransfected with MN promoter-CAT constructs and pSV2neo were used.

1. To detect basal activity of the MN promoter and to estimate the position of the core promoter, expression of the CAT gene from constructs pMN1 to pMN7 after transfection to CGL3 cells was analyzed. Plasmids with progressive 5' deletions were transfected into CGL3 cells and activity was analyzed by CAT assay. [8 µg of DNA was used for transfection in all cases except pBLV-LTR (2 µg).]

Only very weak CAT activity was detected in cells transfected by pMN1 and pMN2 (containing respectively 933 bp and 600 bp of the promoter sequence). A little higher activity was exhibited with the constructs pMN3, pMN4 and pMN6 (containing respectively 446 bp, 243 bp and 58 bp of the promoter). A slight peak of activity was obtained with pMN5 (starting at position −172 with respect to the transcription start.) Thus, the function of the MN core promoter can be assigned to a region of approximately 500 bp immediately upstream from the MN transcription initiation site.

Interestingly, the activity of the large Bd3 region (covering 3.5 kbp upstream of the transcription start) was severalfold higher than the activity of the core promoter. However, its level was still much lower than that exhibited by a positive control, i.e., BLV-LTR transactivated by Tax, and even lower than the activity of BLV-LTR without transactivation. That the activity of Bd3 was elevated in comparison to the core promoter suggests the presence of some regulatory elements. Such elements are most probably situated in the sequence between pMN1 and Bd3 (i.e. from −1 kbp to −3.5 kbp) [SEQ ID NO: 58]. The cloning and transfection of several deletion versions of Bd3 covering the indicated region can be used to determine the location of the putative regulatory elements.

Similar results were obtained from transfecting KATO III cells with Bd3 and pMN4. The transfected cells expressed a lower level of MN than the CGL3 cells. Accordingly, the activity of the MN promoter was found to be lower than in CGL3 cells.

2. In a parallel approach to study the MN promoter, an analysis based on G418 selection of cells transfected by plasmids containing the promoter of interest cloned upstream from the neo gene was made. This approach is suitable to study weak promoters, since its sensitivity is much higher than that of a standard CAT assay. The principle underlying the method is as follows: an active promoter drives expression of the neo gene which protects transfected cells from the toxic effect of G418, whereas an inactive promoter results in no neo product being made and the cells transfected thereby die upon the action of G418. Therefore, the activity of the promoter can be estimated according to the number of cell colonies obtained after two weeks of selection with G418. Three constructs were used in the initial experiments—pMN1neo, pMN4neo and pMN7neo. As pMN7neo contains only 30 bp upstream of the transcription start site, it was considered a negative control. As a positive control, pSV2neo with a promoter derived from SV40 was used. Rat2TK⁻ cells were chosen as the recipient cells, since they are transfectable with high efficiency by the calcium precipitation method.

After transfection, the cells were subjected to two weeks of selection. Then the medium was removed, the cells were rinsed with PBS, and the colonies were rendered visible by staining with methylene blue. The results obtained from three independent experiments corroborated the data from the CAT assays. The promoter construct pMN4neo exhibited higher transcriptional activity than pMN1 neo. However, the difference between the positive control and pMN4neo was not so striking as in the CAT assay. That may have been due to both lower promoter activity of pSV2neo compared to Tax-transactivated pBLV-LTR and to different conditions for cell growth after transfection. From that point of view, stable transfection is probably more advantageous for MN expression, since the cells grow in colonies with close cell to cell contact, and the experiment lasts much longer, providing a better opportunity to detect promoter activity.

3. Stable transfectants expressing MN promoter-CAT chimeric genes were prepared by the cotransfection of relevant plasmids with pSV2neo. As recipient cells, HeLa cells were used first. However, no clones expressing the promoter-CAT constructs were obtained. That negative result was probably caused by homologic recombination of the transfected genomic region of MN (e.g. the promoter) with the corresponding endogenous sequence. On the basis of that experience, C33 cells derived from a HPV-negative cervical carcinoma were used. C33 cells do not express MN, since during the process of tumorigenesis, they lost genetic material including chromosomal region 9p which contains the MN gene. In these experiments, the absence of the MN gene may represent an advantage as the possibility of homologic recombinations is avoided.

C33 Cells Transfected with MN Promoter-CAT Constructs

C33 cells expressing the CAT gene under MN promoter regions Bd3 (−3500/+31) [SEQ ID NO: 90] and MN5 (−172/+31) [SEQ ID NO: 91] were used for initial experiments to analyze the influence of cell density on the transcriptional activity of the MN promoter. The results indicated that signals generated after cells come into close contact activate transcription of the CAT protein from the MN promoter in proportion to the density of the cell culture. Interestingly, the data indicated that the MN protein is not required for this phase of signal transduction, since the influence of density is clearly demonstrated in MN-negative C33 cells. Rather, it appears that MN protein acts as an effector molecule produced in dense cells in order to perform a certain biological function (i.e., to perturb contact inhibition). Also interestingly, the MN promoter activity is detectable even in very sparse cell cultures suggesting that MN is expressed at a very low level also is sparse subconfluent culture.

Deletion Variants. Deletion variants of the Bd3-CAT promoter construct were then prepared. The constructs were cotransfected with pSV2neo into C33 cervical cells. After selection with G418, the whole population of stably transfected cells were subjected to CAT ELISA analysis. Expression of the deletion constructs resulted in the synthesis of similar levels of CAT protein to that obtained with the Bd3-CAT construct. On the basis of that preliminary data, the inventors proposed that sequences stimulating transcription of MN are located between −3506 and −3375 bp [SEQ ID NO: 92] upstream from the transcription start. That is the sequence exhibiting homology to HERV-K LTR.

However, transient transfection studies in CGL3 cells repeatedly revealed that the LTR region is not required for the enhancement of basal MN promoter activity. Further, results obtained in CGL3 cells indicate that the activating element is localized in the region from −933 to −2179 [SEQ ID NO: 110] with respect to transcription initiation site (the position of the region having been deduced from overlapping sequences in the Bd3 deletion mutants).

Interaction of Nuclear Proteins with MN Promoter Sequences

In order to identify transcription factors binding to the MN promoter and potentially regulating its activity, a series of analyses using an electrophoretic mobility shift assay (EMSA) and DNase I footprinting analysis (FTP) were performed.

EMSA

In the EMSA, purified promoter fragments MN4 (−243/+31) [SEQ ID NO: 93], MN5 (−172/+31) [SEQ ID NO: 91], MN6 (−58/+31) [SEQ ID NO: 94] and pMN7 (−30/+31) [SEQ ID NO: 95], labeled at the 3' ends by Klenow enzyme, were allowed to interact with proteins in nuclear extracts prepared from CGL1 and CGL3 cells. [40 µg of nuclear proteins were incubated with 30,000 cpm end-labeled DNA fragments in the presence of 2 µg poly(dIdC).] DNA-protein complexes were analysed by PAGE (native 6%), where the complexes created extra bands that migrated more slowly than the free DNA fragments, due to the shift in mobility which is dependent on the moiety of bound protein.

The EMSA of the MN4 and MN5 promoter fragments revealed several DNA-protein complexes; however, the binding patterns obtained respectively with CGL1 and CGL3 nuclear extracts were not identical. There is a single CGL-1 specific complex.

The EMSA of the MN6 promoter fragment resulted in the formation of three identical complexes with both CGL1 and CGL3 nuclear extracts, whereas the MN7 promoter fragment did not bind any nuclear proteins.

The EMSA results indicated that the CGL1 nuclear extract contains a specific factor, which could participate in the negative regulation of MN expression in CGL1 cells. Since the specific DNA-protein complex is formed with MN4 (−243/+31) [SEQ. ID NO.: 93] and MN5 (−172/+31) [SEQ. ID NO.: 91] promoter fragments, but not with MN6 (−58/+31) [SEQ ID NO: 94], it appears that the binding site of the protein component of that specific complex is located between −173 and −58 bp [SEQ. ID NO.: 96] with respect to transcription initiation.

The next step was a series of EMSA analyses using double stranded (ds) oligonucleotides designed according to the protected regions in FTP analysis. A ds oligonucleotide derived from the protected region PR2 [covering the sequence from −72 to −56 bp (SEQ ID NO: 111)] of the MN promoter provided confirmation of the binding of the AP-1 transcription factor in competitive EMSA using commercial ds oligonucleotides representing the binding site for AP-1.

EMSA of ds oligonucleotides derived from the protected regions of PR1 [−46 to −24 bp (SEQ ID NO: 112)], PR2 [−72 to −56 bp (SEQ ID NO: 111)], PR3 [−102 to −85 (SEQ ID NO: 113)] and PR5 [−163 to −144 (SEQ ID NO: 114)] did not reveal any differences in the binding pattern of nuclear proteins extracted from CGL1 and CGL3 cells, indicating that those regions do not bind crucial transcription factors which control activation of the MN gene in CGL3, or its negative regulation in CGL1. However, EMSA of ds oligonucleotides from the protected region PR4 [−133 to −108; SEQ ID NO: 115] repeatedly showed remarkable quantitative differences between binding of CGL1 and CGL3 nuclear proteins. CGL1 nuclear proteins formed a substantially higher amount of DNA-protein complexes, indicating that the PR4 region contains a binding site for specific transcription factor(s) that may represent a negative regulator of MN gene transcription in CGL1 cells. That fact is in accord with the previous EMSA data which showed CGL-1 specific DNA-protein complex with the promoter fragments pMN4 (−243/+31; SEQ ID NO: 93) and pMN5 (−172/+31; SEQ ID NO: 91), but not with pMN6 (−58/+31; SEQ ID NO: 94).

To identify the protein involved or the formation of a specific complex with the MN promoter in the PR4 region, relevant ds oligonucleotides covalently bound to magnetic beads will be used to purify the corresponding transcription factor. Alternatively the ONE Hybrid System® [Clontech (Palo Alto, Calif. (USA)] will be used to search for and clone transcription factors involved in regulation of the analysed promoter region. A cDNA library from HeLa cells will be used for that investigation.

FTP

To determine the precise location of cis regulatory elements that participate in the transcriptional regulation of the MN gene, FTP was used. Proteins in nuclear extracts prepared respectively from CGL1 and CGL3 cells were allowed to interact with a purified ds DNA fragment of the MN promoter (MN4, −243/+31) [SEQ ID NO: 93] which was labeled at the 5' end of one strand. [MN4 fragments were labeled either at Xho1 site (−243/+31*) or at Xba1 site (*−243/+31).] The DNA-protein complex was then subjected to DNase I attack, which causes the DNA chain to break at certain bases if they are not in contact with proteins. [A control used BSA instead of DNase.] Examination of the band pattern of the denatured DNA after gel electrophoresis [8% denaturing gel] indicates which of the bases on the labeled strand were protected by protein.

FTP analysis of the MN4 promoter fragment revealed 5 regions (I-V) protected at both the coding and noncoding strand, as well as two regions (VI and VII) protected at the coding strand but not at the noncoding strand. FIG. 6 indicates the general regions on the MN promoter that were protected.

The sequences of the identified protected regions (PR) were subjected to computer analysis using the SIGNALSCAN program to see if they corresponded to known consensus sequences for transcription factors. The data obtained by that computer analyses are as follows:

| | |
|---|---|
| PR I | coding strand - AP-2, p53, GAL4 noncoding strand - JCV-repeated |
| PR II | coding strand - AP-1, CGN4 noncoding strand - TCF-1, dFRA, CGN4 |
| PR III | coding strand - no known consensus sequence, only partial overlap of AP1 noncoding strand - 2 TCF-1 sites |
| PR IV | coding strand - TCF-1, ADR-1 noncoding strand - CTCF, LF-A1, LBP-1 |
| PR V | coding strand - no known consensus motif noncoding strand - JCV repeated |
| PR VI | coding strand - no known consensus motif noncoding strand - T antigen of SV 40, GAL4 |
| PR VII | coding strand - NF-uE4, U2snRNA.2 noncoding strand - AP-2, IgHC.12, MyoD. |

In contrast to EMSA, the FTP analysis did not find any differences between CGL1 and CGL3 nuclear extracts. However, the presence of specific DNA-protein interactions detected in the CGL1 nuclear extracts by EMSA could have resulted from the binding of additional protein to form DNA protein-protein complex. If that specific protein did not contact the DNA sequence directly, its presence would not be detectable by FTP.

EMSA Supershift Analysis

The results of the FTP suggests that transcription factors AP-1, AP-2 as well as tumor suppressor protein p53 are potentially involved in the regulation of MN expression. To confirm binding of those particular proteins to the MN promoter, a supershift analysis using antibodies specific for those proteins was performed. For this analysis, DNA-protein complexes prepared as described for EMSA were allowed to interact with MAbs or polyclonal antibodies specific for proteins potentially included in the complex. The binding of antibody to the corresponding protein results in an additional shift (supershift) in mobility of the DNA-protein-antibody complex which is PAGE visualized as an additional, more slowly migrating band.

By this method, the binding of AP-2 to the MN promoter was confirmed. However, this method did not evidence binding of the AP-1 transcription factor. It is possible that MN protein binds AP-1-related protein, which is antigenically different from the AP-1 recognized by the antibodies used in this assay.

Also of high interest is the possible binding of the p53 tumor suppressor protein to the MN promoter. It is well known that wt p53 functions as a transcription factor, which activates expression of growth-restricting genes and down-modulates, directly or indirectly, the expression of genes that are required for ongoing cell proliferation. Transient co-transfection experiments using the pMN4-CAT promoter construct in combination with wt p53 cDNA and mut p53 cDNA, respectively, suggested that wt p53, but not mut p53, negatively regulates expression of MN. In addition, one of two p53-binding sites in the MN promoter is protected in FTP analysis (FIG. 6), indicating that it binds to the corresponding protein. Therefore, supershift analysis to prove that p53 binds to the MN promoter with two p53-specific antibodies, e.g. Mabs 421 and DO-1 [the latter kindly provided by Dr. Vojtesek from Masaryk Memorial Cancer Institute in Brno, Czech Republic] are to be performed with appropriate nuclear extracts, e.g. from MCF-7 breast carcinoma cells which express wt p53 at a sufficient level.

Regulation of MN Expression and MN Promoter

MN appears to be a novel regulatory protein that is directly involved in the control of cell proliferation and in cellular transformation. In HeLa cells, the expression of MN is positively regulated by cell density. Its level is increased by persistent infection with LCMV. In hybrid cells between HeLa and normal fibroblasts, MN expression correlates with tumorigenicity. The fact that MN is not present in nontumorigenic hybrid cells (CGL1), but is expressed in a tumorigenic segregant lacking chromosome 11, indicates that MN is negatively regulated by a putative suppressor in chromosome 11.

Evidence supporting the regulatory role of MN protein was found in the generation of stable transfectants of NIH 3T3 cells that constitutively express MN protein. As a consequence of MN expression, the NIH 3T3 cells acquired features associated with a transformed phenotype: altered morphology, increased saturation density, proliferative advantage in serum-reduced media, enhanced DNA synthesis and capacity for anchorage-independent growth. Further, flow cytometric analyses of asynchronous cell populations indicated that the expression of MN protein leads to accelerated progression of cells through G1 phase, reduction of cell size and the loss of capacity for growth arrest under inappropriate conditions. Also, MN expressing cells display a decreased sensitivity to the DNA damaging drug mitomycin C.

Nontumorigenic human cells, CGL1 cells, were also transfected with the full-length MN cDNA. The same pSG5C-MN construct in combination with pSV2neo plasmid as used to transfect the NIH 3T3 cells was used. Out of 15 MN-positive clones (tested by SP-RIA and Western blotting), 3 were chosen for further analysis. Two MN-negative clones isolated from CGL1 cells transfected with empty plasmid were added as controls. Initial analysis indicates that the morphology and growth habits of MN-transfected CGL1 cells are not changed dramatically, but their proliferation rate and plating efficiency is increased.

MN Promoter—Sense/Antisense Constructs

When the promoter region from the MN genomic clone, isolated as described above, was linked to MN cDNA and transfected into CGL1 hybrid cells, expression of MN protein was detectable immediately after selection. However, then it gradually ceased, indicating thus an action of a feedback regulator. The putative regulatory element appeared to be acting via the MN promoter, because when the full-length cDNA (not containing the promoter) was used for transfection, no similar effect was observed.

An "antisense" MN cDNA/MN promoter construct was used to transfect CGL3 cells. The effect was the opposite of that of the CGL1 cells transfected with the "sense" construct. Whereas the transfected CGL1 cells formed colonies several times larger than the control CGL1, the transfected CGL3 cells formed colonies much smaller than the control CGL3 cells. The same result was obtained by antisense MN cDNA transfection in SiHa and HeLa cells.

For those experiments, the part of the promoter region that was linked to the MN cDNA through a BamHI site was derived from a NcoI-BamHI fragment of the MN genomic clone [Bd3] and represents a region a few hundred bp upstream from the transcription initiation site. After the ligation, the joint DNA was inserted into a pBK-CMV expression vector [Stratagene]. The required orientation of the inserted sequence was ensured by directional cloning and subsequently verified by restriction analysis. The transfection procedure was the same as used in transfecting the NIH 3T3 cells, but co-transfection with the pSV2neo plasmid was not necessary since the neo selection marker was already included in the pBK-CMV vector.

After two weeks of selection in a medium containing G418, remarkable differences between the numbers and sizes of the colonies grown were evident as noted above. Immediately following the selection and cloning, the MN-transfected CGL1 and CGL3 cells were tested by SP-RIA for expression and repression of MN, respectively. The isolated transfected CGL1 clones were MN positive (although the level was lower than obtained with the full-length cDNA), whereas MN protein was almost absent from the transfected CGL3 clones. However, in subsequent passages, the expression of MN in transfected CGL1 cells started to cease, and was then blocked perhaps evidencing a control feedback mechanism.

As a result of the very much lowered proliferation of the transfected CGL3 cells, it was difficult to expand the majority of cloned cells (according to SP-RIA, those with the lowest levels of MN), and they were lost during passaging. However, some clones overcame that problem and again expressed MN. It is possible that once those cells reached a higher quantity, that the level of endogenously produced MN mRNA increased over the amount of ectopically expressed antisense mRNA.

Identification of Specific Transcription Factors Involved in Control of MN Expression Control of MN expression at the transcription level involves regulatory elements of the MN promoter. Those elements bind transcription factors that are responsible for MN activation in tumor cells and/or repression in normal cells. The identification and isolation of those specific transcription factors and an understanding of how they regulate MN expression could result in their therapeutic utility in modulating MN expression.

EMSA experiments indicate the existence of an MN gene repressor. Using the One Hybrid System® [Clontech (Palo Alto, Calif.); an in vivo yeast genetic assay for isolating genes encoding proteins that bind to a target, cis-acting regulatory element or any other short DNA-binding sequence; Fields and Song, *Nature,* 340: 245 (1989); Wu et al., *EMBO J.,* 13: 4823 (1994)] and subtractive suppressive PCR (SSH). SSH allows the cloning of genes that are differentially expressed under conditions which are known to up or down regulate MN expression such as density versus sparsity of HeLa cells, and suspension versus adherent HeLa cells.

In experiments with HPV immobilized cervical cells (HCE 16/3), it was found that the regulation of MN expression differs from that in fully transformed carcinoma cells. For example, glucocorticoid hormones, which activate HPV transcription, negatively regulate MN expression in HCE, but stimulate MN in HeLa and SiHa. Further keratinocyte growth factors, which down regulates transcription of HPV oncogenes, stimulates MN expression in suspension HCE but not in adherent cells.

EGF and insulin are involved in the activation of MN expression in both immortalized and carcinoma cells. All the noted facts can be used in the search for MN-specific transcription factors and in the modulation of MN expression for therapeutic purposes.

Deduced Amino Acid Sequence

The ORF of the MN cDNA shown in FIG. 1 has the coding capacity for a 459 amino acid protein with a calculated molecular weight of 49.7 kd. The overall amino acid composition of the MN/CA IX protein is rather acidic, and predicted to have a pi of 4.3. Analysis of native MN/CA IX protein from CGL3 cells by two-dimensional electrophoresis followed by immunoblotting has shown that in agreement with computer prediction, the MN/CA IX is an acidic protein existing in several isoelectric forms with pis ranging from 4.7 to 6.3.

As assessed by amino acid sequence analysis, the deduced primary structure of the MN protein can be divided into four distinct regions. The initial hydrophobic region of 37 amino acids (aa) corresponds to a signal peptide. The mature protein has an N-terminal or extracellular part of 377 amino acids [aa 38-414 (SEQ ID NO: 87], a hydrophobic transmembrane segment of 20 amino acids [aa 415-434 (SEQ ID NO: 52)] and a C-terminal region of 25 amino acids [aa 435-459 (SEQ ID NO: 53)].

The extracellular part is composed of two distinct domains: (1) a proteoglycan-like domain [aa 53-111 (SEQ ID NO: 50)]; and (2) a CA domain, located close to the plasma membrane [aa 135-391 (SEQ ID NO: 51)]. [The amino acid numbers are keyed to those of FIG. 1.]

More detailed insight into MN protein primary structure disclosed the presence of several consensus sequences. One potential N-glycosylation site was found at position 346 of FIG. 1. That feature, together with a predicted membrane-spanning region are consistent with the results, in which MN was shown to be an N-glycosylated protein localized in the plasma membrane. MN protein sequence deduced from cDNA was also found to contain seven S/TPXX sequence elements [SEQ ID NOS: 25 AND 26] (one of them is in the signal peptide) defined by Suzuki, *J. Mol. Biol.,* 207: 61-84 (1989) as motifs frequently found in gene regulatory proteins. However, only two of them are composed of the suggested consensus amino acids.

Experiments have shown that the MN protein is able to bind zinc cations, as shown by affinity chromatography using Zn-charged chelating sepharose. MN protein immunoprecipitated from HeLa cells by Mab M75 was found to have weak catalytic activity of CA. The CA-like domain of MN has a structural predisposition to serve as a binding site for small soluble domains. Thus, MN protein could mediate some kind of signal transduction.

MN protein from LCMV-infected HeLA cells was shown by using DNA cellulose affinity chromatography to bind to immobilized double-stranded salmon sperm DNA. The binding activity required both the presence of zinc cations and the absence of a reducing agent in the binding buffer.

CA Domain Required for Anchorage Independence But for Increased Proliferation of Transfected NIH 3T3 Fibroblasts In transfected NIH 3T3 fibroblasts, MN protein induces morphologic transformation, increased proliferation and anchorage independence. The consequences of constitutive expression of two MN-truncated variants in NIH 3T3 cells were studied. It was found that the proteoglycan-like region is sufficient for the morphological alteration of transfected cells and displays the growth-promoting activity presumably related to perturbation of contact inhibition.

The CA domain is essential for induction of anchorage independence, whereas the TM anchor and IC tail are dispensable for that biological effect. The MN protein is also capable of causing plasma membrane ruffling in the transfected cells and appears to participate in their attachment to the solid support. The data evince the involvement of MN in the regulation of cell proliferation, adhesion and intercellular communication.

Sequence Similarities

Computer analysis of the MN cDNA sequence was carried out using DNASIS and PROSIS (Pharmacia Software packages). GenBank, EMBL, Protein Identification Resource and SWISS-PROT databases were searched for all possible sequence similarities. In addition, a search for proteins sharing sequence similarities with MN was performed in the MIPS databank with the FastA program [Pearson and Lipman, *PNAS* (USA), 85: 2444 (1988)].

The proteoglycan-like domain [aa 53-111 (SEQ ID NO: 50)], which is between the signal peptide and the CA domain, shows significant homology (38% identity and 44% positivity) with a keratan sulphate attachment domain of a human large aggregating proteoglycan aggrecan [Doege et al., *J. Biol. Chem.*, 266: 894-902 (1991)].

The CA domain [aa 135-391 (SEQ ID NO: 51)] is spread over 265 aa and shows 38.9% amino acid identity with the human CA VI isoenzyme [Aldred et al., *Biochemistry*, 30: 569-575 (1991)]. The homology between MN/CA IX and other isoenzymes is as follows: 35.2% with CA II in a 261 aa overlap [Montgomery et al., *Nucl. Acids. Res.*, 15; 4687 (1987)], 31.8% with CA I in a 261 aa overlap [Barlow et al., *Nucl. Acids Res.*, 15: 2386 (1987)], 31.6% with CA IV in a 266 aa overlap [Okuyama et al., PNAS (USA) 89: 1315-1319 (1992)], and 30.5% with CA III in a 259 aa overlap (Lloyd et al., *Genes. Dev.*, 1: 594-602 (1987)].

In addition to the CA domain, MN/CA IX has acquired both N-terminal and C-terminal extensions that are unrelated to the other CA isoenzymes. The amino acid sequence of the C-terminal part, consisting of the transmembrane anchor and the intracytoplasmic tail, shows no significant homology to any known protein sequence.

The MN gene was clearly found to be a novel sequence derived from the human genome. The overall sequence homology between the cDNA MN sequence and cDNA sequences encoding different CA isoenzymes is in a homology range of 48-50% which is considered by ones in the art to be low. Therefore, the MN cDNA sequence is not closely related to any CA cDNA sequences.

Only very closely related nt sequences having a homology of at least 80-90% would hybridize to each other under stringent conditions. A sequence comparison of the MN cDNA sequence shown in FIG. 1 and a corresponding cDNA of the human carbonic anhydrase II (CA II) showed that there are no stretches of identity between the two sequences that would be long enough to allow for a segment of the CA II cDNA sequence having 25 or more nucleotides to hybridize under stringent hybridization conditions to the MN cDNA or vice versa.

A search for nt sequences related to MN gene in the EMBL Data Library did not reveal any specific homology except for 6 complete and 2 partial Alu-type repeats with homology to Alu sequences ranging from 69.8% to 91% [Jurka and Milosavljevic, *J. Mol. Evol.* 32: 105-121 (1991)], Also a 222 bp sequence proximal to the 5' end of the genomic region is shown to be closely homologous to a region of the HERV-K LTR.

In general, nucleotide sequences that are not in the Alu or LTR-like regions, of preferably 25 bases or more, or still more preferably of 50 bases or more, can be routinely tested and screened and found to hybridize under stringent conditions to only MN nucleotide sequences. Further, not all homologies within the Alu-like MN genomic sequences are so close to Alu repeats as to give a hybridization signal under stringent hybridization conditions. The percent of homology between MN Alu-like regions and a standard Alu-J sequence are indicated as follows:

| Region of Homology within MN Genomic Sequence [SEQ ID NO: 5; FIG. 2A-F] | SEQ. ID. NOS. | |
|---|---|---|
| | | % Homology to Entire Alu-J Sequence |
| 921-1212 | 59 | 89.1% |
| 2370-2631 | 60 | 78.6% |
| 4587-4880 | 61 | 90.1% |
| 6463-6738 | 62 | 85.4% |
| 7651-7939 | 63 | 91.0% |
| 9020-9317 | 64 | 69.8% |
| | | % Homology to One Half of Alu-J Sequence |
| 8301-8405 | 65 | 88.8% |
| 10040-10122 | 66 | 73.2%. |

MN Proteins and/or Polypeptides

The phrase "MN proteins and/or polypeptides" (MN proteins/polypeptides) is herein defined to mean proteins and/or polypeptides encoded by an MN gene or fragments thereof. An exemplary and preferred MN protein according to this invention has the deduced amino acid sequence shown in FIG. 1. Preferred MN proteins/polypeptides are those proteins and/or polypeptides that have substantial homology with the MN protein shown in FIG. 1. For example, such substantially homologous MN proteins/polypeptides are those that are reactive with the MN-specific antibodies of this invention, preferably the Mabs M75. MN12, MN9 and MN7 or their equivalents.

A "polypeptide" or "peptide" is a chain of amino acids covalently bound by peptide linkages and is herein considered to be composed of 50 or less amino acids. A "protein" is herein defined to be a polypeptide composed of more than 50 amino acids. The term polypeptide encompasses the terms peptide and oligopeptide.

MN proteins exhibit several interesting features: cell membrane localization, cell density dependent expression in HeLa cells, correlation with the tumorigenic phenotype of HeLa× fibroblast somatic cell hybrids, and expression in several human carcinomas among other tissues. MN protein can be found directly in tumor tissue sections but not in general in counterpart normal tissues (exceptions noted infra as in normal gastric mucosa and gallbladder tissues). MN is also expressed sometimes in morphologically normal appearing areas of tissue specimens exhibiting dysplasia and/or malignancy. Taken together, these features suggest a possible involvement of MN in the regulation of cell proliferation, differentiation and/or transformation.

It can be appreciated that a protein or polypeptide produced by a neoplastic cell in vivo could be altered in sequence from that produced by a tumor cell in cell culture or by a transformed cell. Thus, MN proteins and/or polypeptides which have varying amino acid sequences including without limitation, amino acid substitutions, extensions, deletions, truncations and combinations thereof, fall within the scope of this invention. It can also be appreciated that a protein extant within body fluids is subject to degradative processes, such as, proteolytic processes; thus, MN proteins that are significantly truncated and MN polypeptides may be found in body fluids, such as, sera. The phrase "MN antigen" is used herein to encompass MN proteins and/or polypeptides.

It will further be appreciated that the amino acid sequence of MN proteins and polypeptides can be modified by genetic techniques. One or more amino acids can be deleted or substituted. Such amino acid changes may not cause any measurable change in the biological activity of the protein or polypeptide and result in proteins or polypeptides which are within the scope of this invention, as well as, MN muteins.

The MN proteins and polypeptides of this invention can be prepared in a variety of ways according to this invention, for example, recombinantly, synthetically or otherwise biologically, that is, by cleaving longer proteins and polypeptides enzymatically and/or chemically. A preferred method to prepare MN proteins is by a recombinant means. Particularly preferred methods of recombinantly producing MN proteins are described below for the GST-MN, MN 20-19, MN-Fc and MN-PA proteins.

Recombinant Production of MN Proteins and Polypeptides

A representative method to prepare the MN proteins shown in FIG. 1 or fragments thereof would be to insert the full-length or an appropriate fragment of MN cDNA into an appropriate expression vector as exemplified below. In Zavada et al., WO 93/18152, supra, production of a fusion protein GEX-3X-MN (now termed GST-MN) using the partial cDNA clone (described above) in the vector pGEX-3X (Pharmacia) is described. Nonglycosylated GST-MN (the MN fusion protein MN glutathione S-transferase) from XL1-Blue cells.

Zavada et al., WO 95/34650 describes the recombinant production of both a glycosylated MN protein expressed from insect cells and a nonglycosylated MN protein expressed from E. coli using the expression plasmid pEt-22b [Novagen Inc.; Madison, Wis. (USA)]. Recombinant baculovirus express vectors were used to infect insect cells. The glycosylated MN 20-19 protein was recombinantly produced in baculovirus-infected sf9 cells [Clontech; Palo Alto, Calif. (USA)]. The MN 20-19 protein misses the putative signal peptide (aas 1-37) of SEQ ID NO: 6 (FIG. 1), has a methionine (Met) at the N-terminus for expression, and a Leu-Glu-His-His-His-His-His-His [SEQ. ID NO.: 22] added to the C-terminus for purification.

In order to insert the portion of the MN coding sequence for the GST-MN fusion protein into alternate expression systems, a set of primers for PCR was designed. The primers were constructed to provide restriction sites at each end of the coding sequence, as well as in-frame start and stop codons. The sequences of the primers, indicating restriction enzyme cleavage sites and expression landmarks, are shown below.

```
Primer #20: N-terminus
                                         [SEQ. ID. NO. 17]
                         ┌Translation start
5'GTCGCTAGCTCCATGGGTCATATGCAGAGGTTGCCCCGGATGCAG 3'
    NheI NcoI       NdeI   └MN cDNA #1

Primer #19: C-terminus
                                         [SEQ. ID. NO. 18]
              ┌Translation stop
5'GAAGATGTCTTACTCGAGCATTCTCCAAGATCCAGCCTCTAGG 3'
    BgIII     XhoI  └MN cDNA
```

The SEQ ID NOS: 17 and 18 primers were used to amplify the MN coding sequence present in the GEX-3X-MN vector using standard PCR techniques. The resulting PCR product (termed MN 20-19) was electrophoresed on a 0.5% agarose/1X TBE gel; the 1.3 kb band was excised; and the DNA recovered using the Gene Clean II kit according to the manufacturers instructions [Bio101; LaJolla, Calif. (USA)].

Identification of MN Protein Partner(s)

A search for protein(s) interacting with MN was initiated using expression cloning of the corresponding cDNA(s) and a MN-Fc fusion protein as a probe. The chimerical MN-Fc cDNA was constructed in pSG5C vector by substitution of MN cDNA sequences encoding both the transmembrane anchor and the intracellular tail of MN protein with the cDNA encoding Fc fragment of the mouse IgG. The Fc fragment cDNA was prepared by RT-PCR from the mouse hybridoma producing IgG2a antibody.

The chimerical MN-Fc cDNA was expressed by transient transfection in COS cells. COS cells were transfected using leptofection. Recombinant MN-Fc protein was released to TC medium of the transfected cells (due to the lack of the transmembrane region), purified by affinity chromatography on a Protein A Sepharose and used for further experiments.

Protein extracts from mock-transfected cells and the cells transfected with pSG5C-MN-Fc were analysed by immunoblotting using the M75 MAb, SwαM-Px and ECL Detection® [ECL®—enhanced chemoluminescent system to detect phosphorylated tyrosine residues; Amersham; Arlington, Hts., Ill. (USA)]. The size of MN-Fc protein expressed from the pSG5C vector corresponds to its computer predicted molecular weight.

$^{35}$S-labeled MN-Fc protein was employed in cell surface binding assay. It was found to bind to several mammalian cells, e.g., HeLa, Raji, COS, QT35, BL3. Similar results were obtained in cell adhesion assay using MN-Fc protein dropped on bacterial Petri dishes. These assays revealed that KATO III human stomach adenocarcinoma cell line is lacking an ability to interact with MN-Fc protein. This finding allowed us to use KATO III cells for expression cloning and screening of the cDNA coding for MN-binding protein.

The cDNA expression library in pBK-CMV vector was prepared from dense HeLa cells and used for transfection of KATO III cells. For the first round of screening, KATO III cells were transfected by electroporation. After two days of incubation, the ligand-expressing cells were allowed to bind to MN-Fc protein, then to Protein A conjugated with biotin and finally selected by pulling down with streptavidin-coated magnetic beads. Plasmid DNA was extracted from the selected cells and transformed to E. coli. Individual E. coli colonies were picked and pools of 8-10 clones were prepared. Plasmid DNA from the pools was isolated and used in the second round of screening.

In the second round of screening, KATO III cells were transfected by DEAE dextran method. To identify the pool containing the cDNA for MN-binding protein, an ELISA method based on the binding of MN-Fc to the transfected cells, and detection using peroxidase labelled Protein A were used. Pools are selected by ability to bind MN-Fc.

In the third round of screening, plasmid DNAs isolated from individual bacterial colonies of selected pools are transfected to KATO III cells. The transfected cells are subjected to binding with MN-Fc and detection with Protein A as before. Such exemplary screening is expected to identify a clone containing the cDNA which codes for the putative MN protein partner. That clone would then be sequenced and the expression product confirmed as binding to MN protein by cell adhesion assay. (Far-Western blotting, co-precipitation etc.) Hybridomas producing Mabs to the expression product would then be prepared which would allow the analysis of the biological characteristics of the protein partner of MN.

Preparation of MN-Specific Antibodies

The term "antibodies" is defined herein to include not only whole antibodies but also biologically active fragments of antibodies, preferably fragments containing the antigen binding regions. Further included in the definition of antibodies are bispecific antibodies that are specific for MN protein and to another tissue-specific antigen.

Zavada et al., WO 93/18152 and WO 95/34650 describe in detail methods to produce MN-specific antibodies, and detail steps of preparing representative MN-specific antibodies as the M75, MN7, MN9, and MN12 monoclonal antibodies. Preferred MN antigen epitopes comprise: aa 62-67 (SEQ ID NO: 10); aa 61-66, aa 79-84, aa 85-90 and aa 91-96 (SEQ ID NO: 98); aa 62-65, aa 80-83, aa 86-89 and aa 92-95 (SEQ ID NO: 99); aa 62-66, aa 80-84, aa 86-90 and aa 92-96 (SEQ ID NO: 100); aa 63-68 (SEQ ID NO: 101); aa 62-68 (SEQ ID NO: 102); aa 82-87 and aa 88-93 (SEQ ID NO: 103); aa 55-60 (SEQ ID NO: 11); aa 127-147 (SEQ ID NO: 12); aa 36-51 (SEQ ID NO: 13); aa 68-91 (SEQ ID NO: 14); aa 279-291 (SEQ ID NO: 15); and aa 435-450 (SEQ ID NO: 16). Example 2 provides further description concerning preferred MN antigen epitopes.

Bispecific Antibodies. Bispecific antibodies can be produced by chemically coupling two antibodies of the desired specificity. Bispecific MAbs can preferably be developed by somatic hybridization of 2 hybridomas. Bispecific MAbs for targeting MN protein and another antigen can be produced by fusing a hybridoma that produces MN-specific MAbs with a hybridoma producing MAbs specific to another antigen. For example, a cell (a quadroma), formed by fusion of a hybridoma producing a MN-specific MAb and a hybridoma producing an anti-cytotoxic cell antibody, will produce hybrid antibody having specificity of the parent antibodies. [See, e.g., *Immunol, Rev.* (1979); *Cold Spring Harbor Symposium Quant. Biol.,* 41: 793 (1977), van Dijk et al., *Int. J. Cancer,* 43: 344-349 (1989).] Thus, a hybridoma producing a MN-specific MAb can be fused with a hybridoma producing, for example, an anti-T3 antibody to yield a cell line which produces a MN/T3 bispecific antibody which can target cytotoxic T cells to MN-expressing tumor cells.

It may be preferred for therapeutic and/or imaging uses that the antibodies be biologically active antibody fragments, preferably genetically engineered fragments, more preferably genetically engineered fragments from the $V_H$ and/or $V_L$ regions, and still more preferably comprising the hypervariable regions thereof. However, for some therapeutic uses bispecific antibodies targeting MN protein and cytotoxic cells would be preferred.

Epitopes

The affinity of a MAb to peptides containing an epitope depends on the context, e.g. on whether the peptide is a short sequence (4-6 aa), or whether such a short peptide is flanked by longer aa sequences on one or both sides, or whether in testing for an epitope, the peptides are in solution or immobilized on a surface. Therefore, it would be expected by ones of skill in the art that the representative epitopes described herein for the MN-specific MAbs would vary in the context of the use of those MAbs.

The term "corresponding to an epitope of an MN protein/polypeptide" will be understood to include the practical possibility that, in some instances, amino acid sequence variations of a naturally occurring protein or polypeptide may be antigenic and confer protective immunity against neoplastic disease and/or anti-tumorigenic effects. Possible sequence variations include, without limitation, amino acid substitutions, extensions, deletions, truncations, interpolations and combinations thereof. Such variations fall within the contemplated scope of the invention provided the protein or polypeptide containing them is immunogenic and antibodies elicited by such a polypeptide or protein cross-react with naturally occurring MN proteins and polypeptides to a sufficient extent to provide protective immunity and/or anti-tumorigenic activity when administered as a vaccine.

Epitope for M75 MAb

The M75 epitope is considered to be present in at least two copies within the 6× tandem repeat of 6 amino acids [aa 61-96 (SEQ ID NO: 97)] in the proteoglycan domain of the MN protein. Exemplary peptides representing that epitope depending on the context may include the following peptides from that tandem repeat: EEDLPS (SEQ ID NO: 10; aa 62-67); GEEDLP (SEQ ID NO: 98; aa 61-66; aa 79-84; aa 85-90; aa 91-96); EEDL (SEQ ID NO: 99; aa 62-65; aa 80-83; aa 86-89; aa 92-95); EEDLP (SEQ ID NO: 100; aa 62-66; aa 80-84; aa 86-90; aa 92-96); EDLPSE (SEQ ID NO: 101; aa 63-68); EEDLPSE (SEQ ID NO: 102; aa 62-68); and DLPGEE (SEQ ID NO: 103; aa 82-87, aa 88-93).

Three synthetic peptides from the deduced aa sequence for the EC domain of the MN protein shown in FIG. 1 were prepared. Those synthetic peptides are represented by aa 51-72 (SEQ ID NO: 104), aa 61-85 (SEQ ID NO: 105) and aa 75-98 (SEQ ID NO: 106). Each of those synthetic peptides contains the motif EEDLP (SEQ ID NO: 100) and were shown to be reactive with the M75 MAb.

Other Epitopes

Mab MN9, Monoclonal antibody MN9 (Mab MN9) reacts to the same epitope as Mab M75, as described above. As Mab M75, Mab MN9 recognizes both the GST-MN fusion protein and native MN protein equally well.

Mabs corresponding to Mab MN9 can be prepared reproducibly by screening a series of mabs prepared against an MN protein/polypeptide, such as, the GST-MN fusion protein, against the peptides representing the epitope for Mabs M75 and MN9. Alternatively, the Novatope system [Novagen] or competition with the deposited Mab M75 could be used to select mabs comparable to Mabs M75 and MN9.

Mab MN12. Monoclonal antibody MN12 (Mab MN12) is produced by the mouse lymphocytic hybridoma MN 12.2.2 which was deposited under ATCC HB 11647. Antibodies corresponding to Mab MN12 can also be made, analogously to the method outlined above for Mab MN9, by screening a series of antibodies prepared against an MN protein/polypeptide, against the peptide representing the epitope for Mab MN12. That peptide is aa 55-aa 60 of FIG. 1 [SEQ ID NO: 11]. The Novatope system could also be used to find antibodies specific for said epitope.

Mab MN7. Monoclonal antibody MN7 (Mab MN7) was selected from mabs prepared against nonglycosylated GST-MN as described above. It recognizes the epitope represented by the amino acid sequence from aa 127 to aa 147 [SEQ ID NO: 12] of the FIG. 1 MN protein. Analogously to methods described above for Mabs MN9 and MN12, mabs corresponding to Mab MN7 can be prepared by selecting mabs prepared against an MN protein/polypeptide that are reactive with the peptide having SEQ ID NO: 12, or by the stated alternative means.

MN-Specific Intrabodies—Targeted Tumor Killing Via Intracellular Expression of MN-Specific Antibodies to Block Transport of MN Protein to Cell Surface The gene encoding antibodies can be manipulated so that the antigen-binding domain can be expressed intracellularly. Such "intrabodies" that are targeted to the lumen of the endoplasmic reticulum provide a simple and effective mechanism for inhibiting the transport of plasma membrane proteins to the cell surface. [Marasco, W. A., "Review—Intrabodies: turning the humoral immune system outside in or intracellular immunization," *Gene Therapy*, 4: 11-15 (1997); Chen et al., "Intracellular antibodies as a new class of therapeutic molecules for gene therapy," *Hum. Gene Ther.*, 5(5): 595-601 (1994); Mhashilkar et al., *EMBO J.*, 14: 1542-1551 (1995); Mhashilkar et al., *J. Virol.*, 71: 6486-6494 (1997); Marasco (Ed.), *Intrabodies: Basic Research and Clinical Gene Therapy Applications*, (Springer Life Sciences 1998; ISBN 3-540-64151-3) (summarizes preclinical studies from laboratories worldwide that have used intrabodies); Zanetti and Capra (Eds.), "Intrabodies: From Antibody Genes to Intracellular Communication," The *Antibodies: Volume* 4, [Harwood Academic Publishers; ISBN 90-5702-559-0 (December 1997)]; Jones and Marasco, *Advanced Drug Delivery Reviews*, 31 (1-2): 153-170 (1998); Pumphrey and Marasco, *Biodrugs*, 9(3): 179-185 (1998); Dachs et al., *Oncology Res.*, 9(6-7); 313-325 (1997); Rondon and Marasco, *Ann. Rev. Microbiol.*, 51: 257-283 (1997)]; Marasco, W. A., *Immunotechnology*, 1(1): 1-19 (1995); and Richardson and Marasco, *Trends in Biotechnology*, 13(8): 306-310 (1995).]

MN-specific intrabodies may prevent the maturation and transport of MN protein to the cell surface and thereby prevent the MN protein from functioning in an oncogenic process. Antibodies directed to MN's EC, TM or IC domains may be useful in this regard. MN protein is considered to mediate signal transduction by transferring signals from the EC domain to the IC tail and then by associating with other intracellular proteins within the cell's interior. MN-specific intrabodies could disrupt that association and perturb that MN function.

Inactivating the function of the MN protein could result in reversion of tumor cells to a non-transformed phenotype. [Marasco et al. (1997), supra.] Antisense expression of MN cDNA in cervical carcinoma cells, as demonstrated herein, has shown that loss of MN protein has led to growth suppression of the transfected cells. It is similarly expected that inhibition of MN protein transport to the cell surface would have similar effects. Cloning and intracellular expression of the M75 MAb's variable region is to be studied to confirm that expectation.

Preferably, the intracellularly produced MN-specific antibodies are single-chain antibodies, specifically single-chain variable region fragments or scFv, in which the heavy- and light-chain variable domains are synthesized as a single polypeptide and are separated by a flexible linker peptide, preferably $(Gly_4-Ser)_3$ [SEQ ID NO: 116].

MN-specific intracellularly produced antibodies can be used therapeutically to treat preneoplastic/neoplastic disease by transfecting preneoplastic/neoplastic cells that are abnormally expressing MN protein with a vector comprising a nucleic acid encoding MN-specific antibody variable region fragments, operatively linked to an expression control sequence. Preferably said expression control sequence would comprise the MN gene promoter.

Antibody-Mediated Gene Transfer Using MN-Specific Antibodies or Peptides for Targeting MN-Expressing Tumor Cells An MN-specific antibody or peptide covalently linked to polylysine, a polycation able to compact DNA and neutralize its negative charges, would be expected to deliver efficiently biologically active DNA into an MN-expressing tumor cell. If the packed DNA contains the HSVtk gene under control of the MN promoter, the system would have double specificity for recognition and expression only in MN-expressing tumor cells. The packed DNA could also code for cytokines to induce CTL activity, or for other biologically active molecules. The M75 MAb (or, for example, as a single chain antibody, or as its variable region) is exemplary of such a MN-specific antibody.

The following examples are for purposes of illustration only and are not meant to limit the invention in any way.

Example 1

Transient Transformation of Mammalian Cells by MN Protein

This example (1) examines the biological consequences of transfecting human or mouse cells with MN-cDNA inserted into expression vectors, mainly from the viewpoint of the involvement of MN protein in oncogenesis; (2) determines if MN protein exerts carbonic anhydrase activity, and whether such activity is relevant for morphologic transformation of cells; and (3) tests whether MN protein is a cell adhesion molecule (CAM).
Synopsis
Methods: MN-DNA was inserted into 3 expression vectors and was used for transfecting human or mouse cells. MN protein was detected by Western blotting, radioimmunoassay or immunoperoxidase staining; in all tests the MN-specific monoclonal antibody M75 (MAb M75) was used. Carbonic anhydrase activity was determined by the acidification velocity of carbonate buffer in $CO_2$ atmosphere.
Results: (1) Cells (human CGL-1 and mouse NIH3T3 cells) transfected with MN-cDNA showed morphologic transformation, but reverted to normal phenotype after 4-5 weeks. (2) This reversion was not due to the loss, silencing or mutation of the MN insert. (3) MN protein has the enzyme activity of a carbonic anhydrase, which can be inhibited with acetazolamide; however, the inhibition of the carbonic anhydrase enzyme activity did not affect transformation. (4) MN protein is an adhesion protein, involved in cell-to-cell contacts.
Background
This example concerns transformation of mammalian cells by MN-cDNA inserted into expression vectors derived from retroviruses. Such vectors are suitable for efficient and stable integration into cellular DNA and for continuous expression of MN protein. Cells transfected with these constructs showed morphologic transformation, but after some time, they reverted to normal phenotype.

Sulfonamides, including acetazolamide, are very potent inhibitors of known carbonic anhydrases [Maren and Ellison, *Mol. Pharmacol.*, 3: 503-508 (1967)]. Acetazolamide was tested to determine if it inhibited also the MN-carbonic anhydrase, and if so, whether inhibition of the enzyme affected cell transformation.

There are reasons to believe that MN protein could be involved in direct cell-to-cell interactions: A) previous observations indicated a functional resemblance of MN protein to surface glycoproteins of enveloped viruses, which mediate virus adsorption to cell surface receptors, and MN participated in the formation of phenotypically mixed virions of vesicular stomatitis virus. B) Inducibility of MN protein expression by growing HeLa cells in densely packed monolayers suggests that it may be involved in direct interactions between cells. C) Finally, there is a structural similarity between the MN protein and receptor tyrosine phosphatase β, which also contains proteoglycan and carbonic anhydrase domains; those domains mediate direct contacts between cells of the developing nervous system [Peles et al., *Cell*, 82: 251-260 (1995)]. Therefore, MN protein was tested to see if it bound to cell surface receptors; the result was clearly positive that it does.

Materials and Methods

Cell Lines

Cells used in this example were: CGL1 and CGL3—respectively non-tumorigenic and tumorigenic HeLa×fibroblast hybrids [Stanbridge et al., *Somat. Cell Genet.*, 7: 699-712 (1981)], mouse cell line NIH3T3, HeLa cells and monkey Vero cells. The NIH3T3 cells were seeded at very low density to obtain colonies started from single cells. The most normal appearing colony, designated subclone 2, was picked for use in the experiments reported in this example.

Expression Vectors

Full-length MN cDNA was acquired from a pBluescript subclone [Pastorek et al., *Oncogene*, 9: 2877-2888 (1994)]. To remove 5' and 3' noncoding sequences, that might reduce subsequent gene expression, a polymerase chain reaction (PCR) was performed. The 5' primer TAGACAGATCTAC-GATGGCTCCCCTGTGCCCCAG [SEQ ID NO: 88] encompasses a translation start site and BglII cloning site, and the 3' primer ATTCCTCTAGACAGTTACCGGCTC-CCCCTCAGAT [SEQ ID NO: 89] encompasses a stop codon and XbaI cloning site. Full-length MN-cDNA as a template and Pfu DNA Polymerase [Stratagene; LaJolla, Calif. (USA)] were used in the reaction.

The PCR product was sequenced and found to be identical with the template; it carried no mutations. The PCR product harbouring solely the MN coding sequence was inserted into three vectors: 1. pMAMneo [Clontech, Palo Alto, Calif. (USA)] plasmid allowing dexamethasone-inducible expression driven by the MMTV-Long Terminal Repeat (LTR) promoter and containing a neo gene for selection of transformants in media supplemented with Geneticin (G418) antibiotics. 2. Retroviral expression vector pGD [Daley et al., *Science*, 247: 824-829 (1990); kindly provided by Prof. David Baltimore, New York-Cambridge)] containing MLV-LTR promoter and neo gene for G418 antibiotics selection. 3. Vaccinia virus expression vector pSC11 [Chakrabarti et al., *Mol. Cell. Biol.*, 5: 3403-3409 (1985)]. Transfection was performed via a calcium-phosphate precipitate according to Sambrook et al. (eds.), *Molecular cloning, A laboratory manual*, 2nd ed., Cold Spring Harbor Laboratory Press (1989).

Vaccinia virus strain Praha clone 13 was used as parental virus [Kutinova et al., *Vaccine*, 13: 487-493 (1995)]. Vaccinia virus recombinant was prepared by a standard procedure [Perkus et al., *Virology*, 152: 285-297 (1986)]. Recombinant viruses were selected and plaque purified twice in rat thymidine-kinase-less RAT2 cells [Topp, W. C., *Virology*, 113: 408-411 (1981)] in the presence of 5'-bromodeoxyuridine (100 μg/ml). Blue plaques were identified by overlaying with agar containing 5-bromo-4-chloro-3-indolyl-β-D-galactopyranoside (X-Gal) (200 μg/ml).

CA Assay

Carbonic anhydrase activity was measured by a micromethod [Brion et al., *Anal. Biochem.*, 175: 289-297 (1988)]. In principle, velocity of the reaction $CO_2+H_2O \rightarrow H_2CO_3$ is measured by the time required for acidification of carbonate buffer, detected with phenol red as a pH indicator. This reaction proceeds even in absence of the enzyme, with $t_0$=control time (this was set to 60 seconds). Carbonic anhydrase reduces the time of acidification to t; one unit of the enzyme activity reduces the time to one half of control time: $t/t_0 = \frac{1}{2}$.

For the experiment, MN protein was immunoprecipitated with Mab M75 from RIPA buffer (1% Triton X-100, 0.1% deoxycholate, 1 mM phenylmethylsulfonyl-fluoride and 200 trypsin-inhibiting units/ml of Trasylol in PBS, pH 7.2) extract of Vero cells infected with vaccinia-MN construct, after the cells developed cytopathic effect, or with "empty" vaccinia as a control. The MN+ antibody complex was subsequently adsorbed to protein A—*Staphylococcus aureus* cells [Kessler, S. W., *J. Immunol.*, 115; 1617-1624 (1975)] and rinsed 2× with PBS and 2× with 1 mM carbonate buffer, pH 8.0. The precipitate was resuspended in the same buffer and added to the reaction mixture. Acetazolamide (Sigma) was tested for inhibition of carbonic anhydrase [Maren and Ellison, supra]. In extracts of infected cells used for immunoprecipitation, the concentration of total proteins was determined by the Lowry method [Lowry et al., *J. Biol. Chem.*, 193: 265-275 (1951)] and that of MN protein by a competition radioimmunoassay as described in Zavada et al., *Int. J. Cancer*, 54: 268-274 (1993).

Western Blots

Western blotting and development of the blots using $^{125}$I-labelled M75 and autoradiography was performed as before [Pastorekova et al., *Virology*, 187: 620-626 (1992); and Zavada (1993), supra].

Adhesion Assay

For the adhesion assay [Hoffman S., "Assays of cell adhesion," IN: *Cell-cell Interactions*, (Stevenson et al. eds.) pp. 1-30 (IRL Press at Oxford University Press; Oxford, N.Y., Tokyo; 1992)], 25 μl aliquots MN protein (affinity purified pGEX-3X MN) [Zavada et al. (1993), supra] or of control proteins were spotted on 5 cm-diameter bacteriological Petri dishes and allowed to bind for 2 hours at room temperature. This yielded circular protein-coated areas of 4-5 mm diameter. MN protein was diluted to 10 μg/ml in 50 mM carbonate buffer, pH 9.2. Patches of adsorbed control proteins were prepared similarly. Those included collagens type I and IV, fibronectin, laminin and gelatin (Sigma products), diluted and adsorbed according to the manufacturer's recommendations; FCS and BSA were also included. After aspiration of the drops, the dishes were rinsed 2× with PBS and saturated for 1 hour with DMEM supplied with 5% FCS. The plates were seeded with 5×10$^5$ cells in 5 ml of DMEM+5% FCS and incubated overnight at 37° C. The plates were rinsed with PBS, and the attached cells were fixed with formaldehyde, post-fixed with methanol and Giemsa stained.

Results

1. Transformation and Reversion of CGL1 Cells Transfected with MN-cDNA

Since the expression of MN protein correlated with the tumorigenicity of HeLa×fibroblast hybrids [Zavada et al. (1993), supra], the non-tumorigenic hybrid CGL1 cells were first tested. Those cells, transfected with the pMAM.MN construct, after selection with Geneticin, formed colonies with varying degrees of transformation; some of them appeared normal. While normal CGL1 cells are contact inhibited, growing in a parallel orientation, the transformed cells formed very dense colonies, showing the loss of contact inhibition. Such colonies grew more slowly than the original CGL 1.

After subcloning, the cells isolated from transformed colonies segregated revertants. The reversion was a gradual, stepwise process; there were colonies with different degrees of reversion. After 2 passages, all the cell population became morphologically indistinguishable from normal CGL1. This was due to the reversion of some cells and to the selective advantage of the revertants, which grew faster than the transformed cells. Despite repeated attempts, not even one single stably transformed cell clone was obtained. No transformed colonies were found in CGL1 cells transfected with an "empty" pMAM control plasmid. Growth of the CGL1+ pMAM.MN revertants in media supplied with 5 µg/ml of dexamethasone for 7 days enhanced the production of MN protein, but the morphology of the cells did not return to transformed.

2. Rescue of Transforming MN from the Revertants

The reversion of MN-transformed cells to normal phenotype could have at least 4 causes: A) loss of the MN insert; B) silencing of the MN insert, e.g., by methylation; C) mutation of the MN insert; D) activation of a suppressor gene, coding for a product which neutralizes transforming activity of MN protein; E) loss of a MN-binding protein. To decide among those alternatives, the following experiment was designed.

MN-cDNA was inserted into pGD, a vector derived from mouse leukemia virus—MLV. A defective virus was thereby engineered, which contained the MN gene and the selective marker neo instead of genes coding for viral structural proteins. With this construct, mouse NIH3T3 cells were transfected. In media supplied with Geneticin, the cells formed colonies with phenotypes ranging from strongly transformed to apparently normal. All of the transformed colonies and about 50% of the normal colonies expressed MN protein. Contrasting with normal NIH3T3 cells, the transformants were also able to form colonies in soft agar, reflective of the loss of anchorage dependence, characteristic of cell transformation. Upon passaging, the cells isolated from transformed colonies reverted to normal morphology, and at the same time, they lost the capacity to form colonies in soft agar, while still expressing the MN protein. This permanent presence of MN protein in revertants ruled out alternatives A) and B) supra, that is, loss or silencing of the MN gene as a cause of reversion.

To decide among the other 3 alternatives, the revertants were superinfected with live, replication competent MLV. This virus grows in NIH3T3 cells without any morphologic manifestations, and it works as a "helper" for the pGD.MN construct. Virus progeny from MLV-infected revertants represents an artificial virus complex [pGD.MN+MLV]. This consists of 2 types of virions: of standard type MLV particles and virions containing the pGD.MN genome, enveloped in structural proteins provided by the "helper" virus. This virus complex was infectious for fresh NIH3T3 cells; it again induced in them morphologic transformation and the capacity to form agar colonies.

Contrasting with NIH3T3 transfected with pGD.MN, all the colonies of cells infected with [pGD.MN+MLV] complex, which grew in the presence of Geneticin, were uniformly transformed and contained MN proteins. The transformants once more reverted to normal phenotype although they kept producing infectious [pGD.MN+MLV] complex, which induced transformation in fresh NIH3T3 cells. This cycle of infection-transformation-reversion was repeated 3 times with the same result. This ruled out alternative C)—mutation of MN-cDNA as a cause of reversion.

Normal NIH3T3 cells formed a contact inhibited monolayer of flat cells, which did not stain with Mab M75 and immunoperoxidase. Cells infected with [pGD.MN+MLV] complex were clearly transformed: they grew in a chaotic pattern and showed loss of contact inhibition. Some of the cells showed signs of apoptosis. Two passages later, the cell population totally reverted to original phenotype as a result of frequent emergence of revertants and of their selective advantages (faster growth and a higher efficiency of plating). In fact, the revertants appeared to grow to a somewhat lower saturation density than the original NIH3T3 cells, showing a higher degree of contact inhibition.

The control NIH3T3 cells did not contain any MN protein (Western blot); while both transformed cells and revertants contained the same amount and the same proportion of 54 and 58 kDa bands of MN protein. In a non-reducing gel, MN protein was present in the form of oligomers of 153 kDa. Consistently, by competition RIA, approximately 40 ng MN/mg total protein was found in both of the transformed cells and revertants.

3. Carbonic Anhydrase Activity and its Inhibition

Since the carbonic anhydrase domain represents a considerable part of the MN protein (see FIG. 8), tests were performed to determine whether it is indeed enzymatically active. Vero cells infected with the vaccinia.MN construct, which contained more of the MN protein than other cells used in the present experiments, served as a source of MN protein. The cells were extracted with RIPA buffer, and MN protein was concentrated and partially purified by precipitation with MAb M75 and SAC. The immunoprecipitate was tested for CA activity. 78 µl of precipitate contained 1 unit of the enzyme. From the extract, the concentration of total proteins and of MN protein was determined; 1 unit of enzyme corresponded to 145 ng of MN protein or to 0.83 mg of total protein. The immunoprecipitate from Vero cells infected with control virus had no enzyme activity. Activity of MN carbonic anhydrase was inhibited by acetazolamide; $1.53 \times 10^{-8}$ M concentration of the drug reduced enzyme activity to 50%.

Preliminary tests showed that confluent cultures of HeLa or of NIH3T3 cells tolerated $10^{-5}$-$10^{-3}$ M concentration of acetazolamide for 3 days without any signs of toxicity and without any effect on cell morphology. In sparse cultures, $10^{-5}$ M acetazolamide did not inhibit cell growth, but $10^{-4}$ M already caused a partial inhibition. Thus, $10^{-5}$ M acetazolamide was added to NIH3T3 cells freshly transformed with the [pGD.MN+MLV] complex. After 4 days of incubation, the colonies were fixed and stained. No difference was seen between cells growing in the presence or absence of acetazolamide; both were indistinguishable from correctly transformed NIH3T3 cells. Thus, the enzymatic activity of carbonic anhydrase is not relevant for the transforming activity of MN protein.

4. Cell Adhesion Assay

To determine whether or not MN protein is a cell adhesion molecule (CAM), adhesion assays were performed in plastic bacteriological Petri dishes (not treated for use with tissue culture). Cells do not adhere to the surfaces of such dishes, unless the dishes are coated with a binding protein. NIH3T3 cells adhered, spread and grew on patches of adsorbed MN protein. Only very few cells attached outside the areas coated with MN protein.

Other variants of the experiment demonstrated that NIH3T3 cells adhered and spread on patches of adsorbed collagen I and IV, fibronectin and laminin. NIH3T3 cells did not attach to dots of adsorbed gelatin, FCS or BSA.

CGL1, HeLa and Vero cells also adhered to MN protein, but 3 leukemia cell lines showed no adherence. CGL3 cells, strongly expressing MN protein adhered less efficiently to MN protein dots then did CGL1. The presence of $10^{-4}$ M acetazolamide in the media did not affect the cell adhesion.

To confirm the specificity of adhesion, MN protein was absorbed with SAC loaded with MAb M75 (directed to MN) or MAb M67, directed to an unrelated antigen (Pastorekova et al., supra), before it was applied to the surface of the Petri dishes. Absorption with the SAC-M75 complex totally abrogated the cell binding activity, whereas absorption with SAC-M67 was without any effect.

Additional Cell Adhesion Results

A shortened MN, missing TM and IC segments, is shed into the medium by 5ET1 cells (a HeLa X fibroblast hybrid, analogous to CGL3 cells that express MN protein abundantly) or by Vero cells infected with VV carrying MN-DNA with deleted TM and IC sequences. The shed MN protein was purified from the media, and tested in cell adhesion assays. The cells adhered, spread and grew only on the patches covered with adsorbed complete MN protein, but not on the dots of MN lacking TM and IC regions. Analogous results have been described also for some other adhesion molecules. A variety of cells (NIH3T3, CGL1, CGL3, HeLa, XC) attached to MN protein dots suggesting that the MN receptor(s) is common on the surface of vertebrate cells.

Tests were also performed with extracellular matrix proteins or control proteins dotted on nitrocellulose. The dot-blots were treated with MN protein solution. Bound MN protein was detected with MAb M75. MN protein absorbed to the dots of collagen I and IV, but not to fibronectin, laminin, gelatine or BSA.

Prospects for therapy. There are many new principles of cancer therapy employing oncoproteins or molecules that interact with them as targets [Mendelsohn and Lippman, "Principles of molecular cell biology of cancer: growth factors," In: DeVita et al., eds., *Cancer: principles and practice of oncology*, pp. 114-133 4th ed., Philadelphia: Lippinocott (1993); DeVita et al., eds., *Biologic therapy of cancer*, 2nd ed., Philadelphia: Lippinocott (1995)]. The MN protein and at least some of its ligands (or receptors) appear to be particularly suitable for such purposes.

Example 2

Identification of MN's Binding Site

MN protein is a tumor-associated cell adhesion molecule (CAM). To identify its binding site, a series of overlapping oligopeptides, spanning the N-terminal domain of the MN protein were synthesized. The N-terminal domain is homologous to that of proteoglycans and contains a tandem repeat of six amino acids.

The series of oligopeptides were tested by the cell adhesion assay procedure essentially as described above in Example 1. The synthetic oligopeptides were immobilized on hydrophobic plastic surfaces to see if they would mediate the attachment, spreading and growth of cells. Also investigated were whether the oligopeptides or antibodies inhibited attachment of cells (NIH3T3, HeLa and CGL1) to purified MN protein coated onto such plastic surfaces. The MN protein was affinity purified on agarose covalently linked to sulfonamide, as the MN protein encompasses a CA domain.

Several of the oligopeptides were found to be biologically active: (i) when immobilized onto the plastic, they mediate attachment of cells (NIH3T3, HeLa and to CGL1); (ii) when added to the media, they compete for attachment to cells with the immobilized MN protein; (iii) these oligopeptides, present in the media do not inhibit attachment of cells to TC plastic, but they prevent cell-cell adhesion and formation of intercellular contacts; (iv) treatment of immobilized MN protein and of active peptides with MAb M75 abrogates their affinity for the cells; and (v) the binding site of MN was determined to be closely related or identical to the epitope for MAb M75, at least two copies of which are located in the 6-fold tandem repeat of 6 amino acids [aa 61-96 (SEQ ID NO: 97)] in the proteoglycan-like domain of MN protein.

It was concluded that ectopically expressed MN protein most likely participates in oncogenesis by intervention into normal cell-cell contacts. MN's binding site represents a potential target for which therapeutic agents can be designed.

Materials and Methods

Affinity chromatography of MN/CA IX. MN/CA IX was purified by a single cycle of adsorption—elution on sulfonamide-agarose, as described for other CAs [Falkbring et al., *FEBS Letters*, 24: 229 (1972)]. We used columns of p-aminoethylbenzenesulfonamide-agarose (Sigma). Columns with adsorbed MN/CA IX were extensively washed with PBS (NaCl 8.0 g/l, KCl 0.2 g/l, $KH_2PO_4$ 0.2 g/l, $Na_2HPO_4$ 1.15 g/l, pH=7.2) and eluted with 0.1 mM acetazolamide (Sigma). All steps of purification were carried out at 0-5° C., pH 7.2, at physiological concentration of salts. Complete MN/CA IX+ was extracted with 1% Triton X-100 in PBS from Vero cells infected with vaccinia virus containing an insert of complete coding region of MN/CA IX as described in Zavada et al., *Int. J. Oncol.*, 10: 857 (1997). Before chromatography, the extract was diluted 1:6 with PBS and centrifuged for 1 h at 1500×g. Truncated MN/CA IX ΔTM ΔIC was produced from an analogous construct except that the 3' downstream primer for PCR was: 5'CGT CTA GAA GGA ATT CAG CTA GAC TGG CTC AGC A 3' [SEQ ID NO: 117]. MN/CA IX Δ was shed into the medium, from which it was affinity purified after centrifugation as above. All steps of purification were monitored by dot-blots.

Cells and media. The following cell lines were used: HeLa, CGL1=non-tumorigenic hybrid HeLa×fibroblast, CGL3=tumorigenic segregant from this hybrid, NIH3T3 cells=mouse fibroblasts. The origin of the cells and growth media are described in Zavada et al., *Int. J. Cancer*, 54: 268 (1993) and Zavada et al., *Int. J. Oncol.*, 857 (1997). In addition, we used also HT29, a cell line derived from colorectal carcinoma (ATCC No. HBT-38).

Cell adhesion assay. The conditions of the assay are basically as described in Example 1. Briefly, 1 μg/ml of purified MN/CA IX in 50 mM mono/bicarbonate buffer, pH 9.2, was adsorbed in 30 μl drops on the bottom of bacteriological 5 cm Petri dishes for 1.5 hr. Then the drops were removed by aspiration and the dishes were 3× rinsed with PBS and blocked with 50% FCS in culture medium for 30 min. There were two variants of the test. In the first one, the whole bottom of the Petri dish was blocked with 50% FCS, and the dishes were seeded with 5 ml of cell suspension ($10^5$ cells/ml). After overnight incubation, the cultures were rinsed with PBS, fixed and stained. In the other variant, only the area of adsorbed MN/CA IX was blocked and on top of MN/CA IX dots were added 30 μl drops of cell suspension in growth medium, containing added oligopeptides (or control without peptides). After incubation, rinsing and fixation, the cultures were stained with 0.5% Trypan blue in 50 mM Tris buffer pH 8.5 for 1 h. rinsed with water and dried. Stained areas of attached cells were extracted with 10% acetic acid, the extracts transferred to 96-well plates and absorbance was measured at 630 nm on microplate reader.

ELISA. Purified GST-MN [Zavada et al. (1993), supra] at concentration 10 ng/ml in carbonate buffer pH 9.2 was adsorbed for 3 h in Maxisorb strips (NUNC). After washing and blocking (1 h) with 0.05% Tween 20 in PBS, 50 μl/well of the antibody+antigen mixtures were added. Final dilution of MAb 75 ascites fluid was $10^{-6}$; concentration of the peptides varied according to their affinity for M75 so as to allow determination of 50% end-point. These mixtures were adsorbed for 1.5 h, followed by washing with Tween-PBS. Bound antibody was detected by antimouse IgG conjugate with peroxidase (SwAM-Px, SEVAC, Prague), diluted 1:1000. In the color reaction OPD (o-phenylenediamine dihydrochloride, Sigma) 1 mg/ml in 0.1 M citrate buffer pH 5.0 was used. To this $H_2O_2$ was added to final concentration 0.03%. This system is balanced so as to allow assay for antigen competing for M75 as well as for peptides binding to the epitope of immobilized GST-MN.

Peptides. The peptides used in this study were prepared by the solid phase method [Merrifield et al., IN: Gutte, B. (ed.), *Peptides: Synthesis, Structures and Applications*, pp. 93-169 (San Diego; Academic Press; 1995)] using the Boc/Bzl strategy. The peptide acids were prepared on PAM-resin and peptide amides on MeBHA resin. Deprotection and splitting from the resin was done by liquid hydrogen fluoride. The peptides were purified by C18 RP HPLC and characterized by amino acid analysis and FAB MS spectroscopy.

Western blots. MN/CA IX antigens from PAGE gels were transferred to PVDF membranes (Immobilon P, Millipore) and developed with M75, followed by SwAM-Px (see above) and diaminobenzidine (Sigma) with $H_2O_2$. For dot-blots we used nitrocellulose membranes.

Phage display. Ph.D.-7 Phage Display Peptide Library kit was used for screening as recommended by manufacturer (New England Biolabs). 96-well plate was coated with peptide SEQ ID NO: 106. Biopanning was carried out by incubating $2 \times 10^{11}$ phage with target coated plate for 1 h. Unbound phages were washed away with TBST (50 mM Tris-HCl pH 7.5, 150 mM NaCl, 0.1% Tween-20) and specifically bound phages were eluted with M75 antibody (2 μg in 100 μl of TBS/well). Eluted phage was amplified and used for additional binding and amplification cycles to enrich the pool in favour of binding sequence. After 5 rounds, individual clones were picked, amplified and sequenced using T7 sequencing kit (Pharmacia).

Results

Affinity chromatography of MN/CA IX protein. For purification of MN/CA IX protein we decided to use affinity chromatography on sulfonamide-agarose column, described previously for other CAs [Falkbring et al., supra]. The advantages of this method are simplicity and the fact that the whole procedure is carried out under non-denaturing conditions. Vaccinia virus vector with an insert of the complete MN/CA9 cDNA, or with truncated cDNA (lacking transmembrane and intracellular domains) was employed as a source of MN/CA IX protein.

A single cycle of adsorption—elution yielded relatively pure proteins: MN/CA IX+ gave 2 bands of 54 and 58 kDa, MN/CA IXΔ of 54.5 and 56 kDa. These proteins strongly reacted with MAb M75 on Western blots. In extracts from HeLa, CGL3 and HT29 the blot revealed 2 bands of the same size as MN/CA IX+ purified from vaccinia virus construct.

Adhesion of cells to MN/CA IX protein. MN/CA IX immobilized on hydrophobic plastic enabled attachment, spreading and growth of cells. Extremely low concentrations of MN/CA IX corresponding to 1 μg/ml of purified protein in adsorption buffer were sufficient to cause this effect; other cell adhesion molecules are used in 10-50× higher concentrations. Only complete MN/CA IX protein was active in cell adhesion test, truncated MN/CA IX did not support cell adhesion at all or it showed only a low adhesion activity and in some instances it even acted as a cell "repellent".

Treatment of the dots of immobilized MN/CA IX with MAb M75 abrogated its capacity to attach the cells, but the control MAb M16, irrelevant for MN/CA IX had no effect. Blocking of cell attachment by M75 shows that the epitope is identical to or overlapping with the binding site of MN/CA IX for cell receptors.

Identification of the epitope recognized by Mab M75. Preliminary mapping of M75 epitope employing partial sequences of extracellular parts of MN/CA9 cDNA expressed from bacterial vectors and tested on Western blots located it in PG region. For exact mapping, our strategy was to synthesize partially overlapping oligopeptides of 15-25 aa covering the PG domain and test them in competition ELISA with M75. According to the results, this was followed by a series of 6-12 aa oligopeptides. A major part of the PG domain consists of a 6-fold tandem repeat of 6 aa (aa 61-96) [SEQ ID NO: 97]; 4 repeats are identical (GEEDLP) [SEQ ID NO: 98] and 2 contain 2 aa exchanged (SEEDSP [SEQ ID NO: 141] and REEDPP [SEQ ID NO: 142]).

Following are the results of competition ELISA with recombinant MN/CA IX and oligopeptides synthesized according to partial sequences of the PG region. MN/CA IX+ and Δ produced in mammalian cells possessed a higher serological activity than any other protein or peptide included in this experiment; fusion protein GST-MN synthesized in bacteria was less active. The following peptides span the PG region: GGSSGEDDPLGEEDLPSEEDSPC (aa 51-72) [SEQ ID NO: 104]; GEEDLPSEEDSPREEDPPGEEDLPGEC (aa 61-85) [SEQ ID NO: 105]; EDPPGEEDLPGEEDLPGEEDLPEVC (aa 75-98) [SEQ ID NO: 106]; and EVKPKSEEEGSLKLE (aa 97-111) [SEQ ID NO: 118]. SEQ ID NOS: 104 and 106 caused 50% inhibition at 1 ng/ml. Those 2 oligopeptides are mutually non-overlapping, thus the epitope is repeated in both of them. SEQ ID NO: 105 was 1000× less active, probably due to a different conformation. SEQ ID NO: 118 was inactive; thus it does not contain the M75 epitope.

The next step for identifying the epitope was to synthesize oligopeptides containing all circular permutations of the motif GEEDLP [SEQ ID NO: 98] repeated twice. All 6 of the following dodecapeptides [SEQ ID NOS: 119-124) were serologically active (2 more and 4 less so): GEEDLPGEEDLP (SEQ ID NO: 119]; EEDLPGEEDLPG [SEQ ID NO: 120]; EDLPGEEDLP [SEQ ID NO: 121]; DLPGEEDLPGEE [SEQ ID NO: 122]; LPGEEDLPGEED [SEQ ID NO: 123]; and PGEEDLPGEEDL [SEQ ID NO: 124]. The following series of 7 aa sequences, flanked by alanine on both ends were tested: APGEEDLPA [SEQ ID NO: 125];

AGEEDLPGA [SEQ ID NO: 126]; AEEDLPGEA [SEQ ID NO: 127]; AEDLPGEEA [SEQ ID NO: 128]; ADLPGEEDA [SEQ ID NO. 129]; and ALPOEEDLA [SEQ ID NO: 130]. The results showed that the minimum serologically active sequence is the oligopeptide APGEEDLPA (SEQ ID NO: 125]. SEQ ID NOS: 127-130 proved negative in competition at 100 µg/ml. Further, none of the following still shorter oligopeptides (6+2aa) competed in ELISA for M75: AGEEDLPA [SEQ ID NO: 131]; AEEDLPGA [SEQ ID NO: 132]: AEDLPGEA [SEQ ID NO: 133]; ADLPGEEA [SEQ ID NO: 134]: ALPGEEDA [SEQ ID NO: 135]; and APGEEDLA [SEQ ID NO: 136].

In the oligopeptides of SEQ ID NOS: 104, 105, 106 and 118, the C-terminal amino acid was present as an acid, whereas in all the other oligopeptides, the C-terminal amino acid was present as an amide. It is clear that the affinity between these oligopeptides and MAb M75 very strongly increases with the size of peptide molecule.

Attempts to demonstrate adhesion of cells to immobilized oligopeptides. Our initial plan was to follow the pioneering work of Piersbacher and Ruoslahti, *PNAS,* 81: 5985 (1984). They linked tested oligopeptides to adsorbed bovine serum albumin by cross-linking agent SPDP (N-succinimidyl 3[pyridylhydro] propionate). This is why we added onto the C-end of oligopeptides SEQ ID NOS: 104-106 cysteine, which would enable oriented linking to adsorbed albumin. We demonstrated linking of the peptides directly in Petri dishes by immunoperoxidase staining with M75. Unfortunately, CGL1 or CGL3 cells adhered to control albumin treated with SPDP and blocked with ethanolamine (in place of oligopeptides) as strongly as to BSA dots with linked oligopeptides. We were unable to abrogate this non-specific adhesion. Oligopeptides SEQ ID NOS: 104-106 adsorb only very poorly to bacteriological Petri dishes, thereby not allowing the performance of the cell adhesion assay.

Alternatively, we tested inhibition of cell adhesion to MN/CA IX dots by oligopeptides added to the media together with the cell suspension, as described by Piersbacher and Ruoslahti, supra. All peptides SEQ ID NOS: 104-106 and 118-136, were tested at concentrations of 100 and 10 µg/ml. None of them inhibited reproducibly the adhesion of CGL1 cells.

Oligopeptides with affinity to M75 epitope which inhibit cell adhesion to MN/CA IX. As an alternative to monoclonal antibodies, we set out to select oligopeptides exerting affinity to M75 epitope as well as to MN/CA IX receptor binding site from a phage display library of random heptapeptides—Ph.D.-7. Our aim was to select phages containing the desired heptapeptides by panning on immobilized peptide SEQ ID NO: 106 and subsequent elution with M75. Eluted phage was multiplied in appropriate bacteria and subjected to 4 more cycles of panning and elution. From the selected phage population, 10 plaques were picked, amplified and the heptapeptide-coding region was sequenced. Only 3 heptapeptides were represented. Those three heptapeptides, after adding alanine on both sides, are the following nonapeptides: AKKMKRRKA [SEQ ID NO: 137]; AITFNAQYA [SEQ ID NO: 138]; and ASASAPVSA [SEQ ID NO: 139]. The last heptapeptide, synthesized again with added terminal alanines as nonapeptide AGQTRSPLA [SEQ ID NO: 140], was identified by panning on GST-MN and eluted with acetazolamide. This last peptide has affinity to the active site of MN/CA IX carbonic anhydrase. We synthesized these peptides of 7+2 aa and tested them in competition ELISA and in cell adhesion inhibition. Both tests yielded essentially consistent results: peptide SEQ ID NO: 138 showed the highest activity, peptide SEQ ID NO: 137 was less active, peptide SEQ ID NO: 139 was marginally positive only in ELISA, and peptide SEQ ID NO: 140 was inactive. In all of those 4 nonapeptides, the C-terminal amide was present as amide.

Discussion

Purification of transmembrane proteins like MN/CA IX often poses technical problems because they tend to form aggregates with other membrane proteins due to their hydrophobic TM segments. To avoid this, we engineered truncated MN/CA IX ΔICΔTM, which is secreted into the medium. Indeed, truncated MN/CA IX was obtained in higher purity than MN/CA IX+. Unfortunately, this protein was of little use for our purposes, since it was inactive in the cell adhesion assay. Such a situation has also been described for other cell adhesion molecules: their shed, shortened form either assumes an inactive conformation, or it adsorbs to hydrophobic plastic "upside down," while complete proteins adsorb by hydrophobic TM segments in the "correct" position.

MN/CA IX protein forms oligomers of 150 kDa, linked by disulfidic bonds. It was not known whether these are homo- or hetero-oligomers, but PAGE and Western blot analysis suggest that these are probably homo-oligomers, most likely trimers, since on the gel stained with Coomassie Blue no additional bands of intensity comparable to 2 bands specific for MN/CA IX appeared. It is also unlikely that there could exist an additional protein co-migrating with one of the 2 major MN/CA IX bands, since the intensity of their staining on the gel and on Western blots is well comparable.

There can be no doubt on the specificity of cell attachment to purified MN/CA IX+. It is abrogated by specific MAb M75, at a dilution 1:1000 of ascites fluid. This is a correction to our previous report in Zavada et al., *Int. J. Oncol.,* 10: 857 (1997) in which we observed that MN/CA IX produced by vaccinia virus vector and fusion protein GST-MN support cell adhesion, but we did not realize that GST anchor itself contains another binding site, which is not blocked by M75.

MAb M75 reacts excellently with MN/CA IX under any circumstances—with native antigen on the surface of living cells, with denatured protein on Western blots and with antigen in paraffin sections of biopsies fixed with formaldehyde, suggesting that the epitope is small and contiguous. In competition ELISA the smallest sequence reactive with M75 was 7+2 aa, but the affinity between M75 and tested peptides strongly depended on their molecular weight. Complete MN/CA IX was 100,000× more active than the smallest serologically active peptide in terms of weight/volume concentration. In terms of molar concentration this difference would be 150,000,000×. Oligopeptides of intermediate size also showed intermediate activities. It remains to be elucidated whether such differences in activity are due to the conformation depending on the size of the molecule, or to the fact that complete MN/CA IX contains several copies of the epitope, but the smallest molecule only one.

Considering the possibility that the epitope is identical with the cell adhesion structure in MN/CA IX, we can understand why we failed to detect inhibition of cell adhesion by the oligopeptides. The binding site is just not as simple as the prototype peptide, RGD [Winter, J., IN Cleland and Craik (eds.), *Protein Engineering, Principles and Practice,* pp. 349-369 (N.Y.; Wiley-Liss; 1996)].

Naturally, one can argue that the size of MN/CA IX is about the same as of immunoglobulin molecule, and that binding of M75 to its epitope may sterically hinder a different sequence of cell attachment site. This objection has been made unlikely by blocking of both M75 epitope and of cell binding site by nonapeptides 7+2 aa. That result strongly suggests that the epitope and the binding site are indeed identical.

MN/CA IX and its PG region in particular appears to be a potential target molecule for therapy for the following reasons: (i) it is exposed on the cell surface; (ii) it is present in high percentage of certain human carcinomas; (iii) it is normally expressed MN/CA IX in the mucosa of alimentary tract which is not accessible to circulating antibodies, in contrast with the tumors; (iv) it is not shed (or only minimally) into the body fluids; (v) the motif GEEDLP [SEQ ID NO: 98] is repeated 18× on the surface of every MN/CA IX molecule. Oligopeptide display libraries are being employed in the first steps to develop new drugs [Winter, J., supra]. Selected oligopeptides can serve as lead compounds for the computerized design of new molecules, with additional properties required from a drug [DeCamp et al., IN Cleland and Craik (eds.), supra at pp. 467-505].

Example 3

Identification of Peptides Binding to MN Protein Using Phage Display (a) To identify peptides that are recognized by MN protein, a heptapeptide phage display library [Ph.D.®-7 Peptide 7-mer Library Kit (phage display peptide library kit); New England Biolabs; Beverly, Mass. (USA)] was screened. In screening the library, a selection process, i.e., biopanning [Parmley and Smith, Gene, 73: 308 (1988); Noren, C. J., NEB Transcript, 8(1): 1 (1996)] was carried out by incubating the phages encoding the peptides with a plate coated with MN protein, washing away the unbound phage, eluting and amplifying the specifically bound phage.

The target MN protein in this process was a glutathione-S-transferase (GST) MN fusion protein (GST-MN). GST-MN is a recombinantly produced fusion protein expressed from pGEX-3X-MN containing the cDNA for the MN protein without the signal peptide. GST-MN was produced in bacteria under modified cultivation conditions (decreased optical density, decreased temperature). Such cultivation prevented premature termination of translation and resulted in synthesis of the protein molecules which were in vast majority of the full length. The GST-MN protein was used for coating of the wells and binding the relevant phages. The bound phages were then eluted by acetazolamide, amplified and used for two additional rounds of screening.

After sequencing of several independent phage clones obtained after the third round of screening, the following heptapeptides were obtained:

| (1) | GETRAPL | (SEQ ID NO: 107) |
| (2) | GETREPL | (SEQ ID NO: 108) |
| (3) | GQTRSPL | (SEQ ID NO: 109) |
| (4) | GQTRSPL | (SEQ ID NO: 109) |
| (5) | GQTRSPL | (SEQ ID NO: 109) |
| (6) | GQTRSPL | (SEQ ID NO: 109) |
| (7) | GQTRSPL | (SEQ ID NO: 109) |

The heptapeptides show very similar or identical sequences indicating that the binding is specific. The fact that phages bearing these heptapeptides were eluted by acetazolamide, an inhibitor of carbonic anhydrase activity, indicates that the peptides bind to the CA domain of MN protein.

(b) Analogous screening of the heptapeptide phage display library is done using collagen I, shown to bind MN protein, for elution of phages. Different peptide(s) binding to different part(s) of the MN protein molecule are expected to be identified. After identifying such MN-binding peptides, the corresponding synthetic peptides shall then be analysed for their biological effects.

Example 4

Accessibility In Vivo of MN Protein Expressed in Tumor Cells and in Stomach

Lewis rats (384 g) carrying a BP6 subcutaneous tumor (about 1 cm in diameter) expressing rat MN protein were injected intraperitoneally (i.p.) with $^{125}$I-M75 Mab ($2.5 \times 10^6$ cpm). Five days later, 0.5-1 g pieces of the tumor and organs were weighed and their radioactivity was measured by a gamma counter.

Table 2? summarizes the results. The highest radioactivity was present in the tumor. Relatively high radioactivity was found in the liver and kidney, apparently reflecting the clearance of mouse IgG from the blood. The stomach continued a relatively low level of radioactivity, indicating that the M75 Mab had only limited access to MN protein exposed in the gastric mucosa.

TABLE 2

Distribution of radioactivity of $^{125}$I-M75 in rat organs and in the tumor

| Organ | cpm/g | | | | |
|---|---|---|---|---|---|
| Kidney | 2153 | 2184 | | | |
| Spleen | 653 | 555 | | | |
| Liver | 1993 | 1880 | | | |
| Lung | 1183 | 1025 | | | |
| Blood | 1449 | | | | |
| Heart | 568 | 477 | | | |
| Stomach | 1184 | 1170 | | | |
| Testis | 812 | 779 | | | |
| Tail | 647 | | | | |
| Tumor | 3646 | 4058 | 3333 | 8653 | 3839 |

Example 5

FACS Analysis of MN Protein Expression in CGL3 Cells—Apoptosis

A FACS investigation was designed to determine the conditions that influence the synthesis of MN protein and to analyse the cell cycle distribution of MN-positive versus MN-negative cells in a CGL3 population stimulated to apoptosis. Previous Western blotting analyses have shown CGL3 cells to express a relatively high amount of MN protein under different cultivation conditions. CGL3 cells are considered a constitutive producer of MN proteins. However, Western blotting does not recognize small differences in the level of protein. In contrast FACS allows the detection of individual MN-positive cells, a calculation of their percentage in the analysed population, an estimation of the level of MN protein in the cells, and a determination of the cell cycle distribution.

To study the effect of cultivation conditions on MN expression in CGL3 cells, the CGL3 cells were plated in different relative densities and serum concentrations. Three days after plating, the cells were collected, surface labeled by M75 Mab followed by FITC-conjugated anti-mouse IgG and immediately analysed by FACS.

The analysis showed that in adherent cells, MN expression is dependent on cell density as is HeLa cells. However, low density cultures still produced detectable amounts of MN protein. In low density cultures, serum concentration does not seem to play a role. In relatively high density cultures, a decreasing serum concentration resulted in slightly diminished MN expression, probably due to a lower density that the cells were able to reach during the three days of cultivation.

The effect of the actual cell density is remarkable, and MN expression (detectable in 15-90% of the cells) represents a very sensitive monitoring factor. In all experiments, there was about a 5% higher percentage of cycling cells in the MN-positive part of the population, compared to the MN-negative part. That fact prompted the analysis of the cell cycle distribution of MN-positive CGL3 cells under unfavorable growth conditions, that is, after induction of apoptosis.

Apoptosis

CGL3 cells were stimulated to apoptotic death by several drugs, including cycloheximide, actimonycin D and dexamethasone. The FACS study showed that the onset of apoptosis is delayed in MN-positive cells suggesting a protective role of MN in this process. It was also observed that the induction of apoptosis resulted in the down-regulation of MN expression in a time-dependent manner. That same phenomenon was described for Bcl-2 anti-apoptotic protein, and there is existing opinion that the down-regulation of certain regulatory genes during apoptosis sensitizes the cells to undergo apoptotic death. To prove the role of MN in apoptosis, a similar study with cells transfected by MN cDNA is to be performed.

The preliminary results indicate the possible involvement of MN in the suppression of apoptosis. The recent view that tumors arise both as a consequence of increased proliferation and decreased cell death appears to be consistent with the association of the MN protein with tumors in vivo.

ATCC Deposits

The materials listed below were deposited with the American Type Culture Collection (ATCC) now at 10810 University Blvd., Manassus, Va. 20110-2209 (USA). The deposits were made under the provisions of the Budapest Treaty on the International Recognition of Deposited Microorganisms for the Purposes of Patent Procedure and Regulations thereunder (Budapest Treaty). Maintenance of a viable culture is assured for thirty years from the date of deposit. The hybridomas and plasmids will be made available by the ATCC under the terms of the Budapest Treaty, and subject to an agreement between the Applicants and the ATCC which assures unrestricted availability of the deposited hybridomas and plasmids to the public upon the granting of patent from the instant application. Availability of the deposited strain is not to be construed as a license to practice the invention in contravention of the rights granted under the authority of any Government in accordance with its patent laws.

|  | Deposit Date | ATCC # |
|---|---|---|
| Hybridoma |  |  |
| VU-M75 | Sep. 17, 1992 | HB 11128 |
| MN 12.2.2 | Jun. 9, 1994 | HB 11647 |
| Plasmid |  |  |
| A4a | Jun. 6, 1995 | 97199 |
| XE1 | Jun. 6, 1995 | 97200 |
| XE3 | Jun. 6, 1995 | 97198 |

The description of the foregoing embodiments of the invention have been presented for purposes of illustration and description. They are not intended to be exhaustive or to limit the invention to the precise form disclosed, and obviously many modifications and variations are possible in light of the above teachings. The embodiments were chosen and described in order to explain the principles of the invention and its practical application to enable thereby others skilled in the art to utilize the invention in various embodiments and with various modifications as are suited to the particular use contemplated.

All references cited herein are hereby incorporated by reference.

SEQUENCE LISTING

```
<160> NUMBER OF SEQ ID NOS: 143

<210> SEQ ID NO 1
<211> LENGTH: 1522
<212> TYPE: DNA
<213> ORGANISM: HUMAN
<220> FEATURE:
<221> NAME/KEY: CDS
<222> LOCATION: (13)..(1389)
<220> FEATURE:
<221> NAME/KEY: mat_peptide
<222> LOCATION: (124)..(1389)

<400> SEQUENCE: 1
acagtcagcc gc atg gct ccc ctg tgc ccc agc ccc tgg ctc cct ctg ttg      51
            Met Ala Pro Leu Cys Pro Ser Pro Trp Leu Pro Leu Leu
                -35                 -30                 -25 atc ccg gcc cct gct cca ggc ctc act gtg caa ctg ctg ctg tca ctg      99
Ile Pro Ala Pro Ala Pro Gly Leu Thr Val Gln Leu Leu Leu Ser Leu
            -20                 -15                 -10 ctg ctt ctg atg cct gtc cat ccc cag agg ttg ccc cgg atg cag gag     147
Leu Leu Leu Met Pro Val His Pro Gln Arg Leu Pro Arg Met Gln Glu
        -5                  -1   1                   5
```

```
gat tcc ccc ttg gga gga ggc tct tct ggg gaa gat gac cca ctg ggc     195
Asp Ser Pro Leu Gly Gly Gly Ser Ser Gly Glu Asp Asp Pro Leu Gly
    10                  15                  20 gag gag gat ctg ccc agt gaa gag gat tca ccc aga gag gag gat cca     243
Glu Glu Asp Leu Pro Ser Glu Glu Asp Ser Pro Arg Glu Glu Asp Pro
25                  30                  35                  40 ccc gga gag gag gat cta cct gga gag gag gat cta cct gga gag gag     291
Pro Gly Glu Glu Asp Leu Pro Gly Glu Glu Asp Leu Pro Gly Glu Glu
                45                  50                  55 gat cta cct gaa gtt aag cct aaa tca gaa gaa gag ggc tcc ctg aag     339
Asp Leu Pro Glu Val Lys Pro Lys Ser Glu Glu Glu Gly Ser Leu Lys
            60                  65                  70 tta gag gat cta cct act gtt gag gct cct gga gat cct caa gaa ccc     387
Leu Glu Asp Leu Pro Thr Val Glu Ala Pro Gly Asp Pro Gln Glu Pro
        75                  80                  85 cag aat aat gcc cac agg gac aaa gaa ggg gat gac cag agt cat tgg     435
Gln Asn Asn Ala His Arg Asp Lys Glu Gly Asp Asp Gln Ser His Trp
    90                  95                  100 cgc tat gga ggc gac ccg ccc tgg ccc cgg gtg tcc cca gcc tgc gcg     483
Arg Tyr Gly Gly Asp Pro Pro Trp Pro Arg Val Ser Pro Ala Cys Ala
105                 110                 115                 120 ggc cgc ttc cag tcc ccg gtg gat atc cgc ccc cag ctc gcc gcc ttc     531
Gly Arg Phe Gln Ser Pro Val Asp Ile Arg Pro Gln Leu Ala Ala Phe
                125                 130                 135 tgc ccg gcc ctg cgc ccc ctg gaa ctc ctg ggc ttc cag ctc ccg ccg     579
Cys Pro Ala Leu Arg Pro Leu Glu Leu Leu Gly Phe Gln Leu Pro Pro
            140                 145                 150 ctc cca gaa ctg cgc ctg cgc aac aat ggc cac agt gtg caa ctg acc     627
Leu Pro Glu Leu Arg Leu Arg Asn Asn Gly His Ser Val Gln Leu Thr
        155                 160                 165 ctg cct cct ggg cta gag atg gct ctg ggt ccc ggg cgg gag tac cgg     675
Leu Pro Pro Gly Leu Glu Met Ala Leu Gly Pro Gly Arg Glu Tyr Arg
    170                 175                 180 gct ctg cag ctg cat ctg cac tgg ggg gct gca ggt cgt ccg ggc tcg     723
Ala Leu Gln Leu His Leu His Trp Gly Ala Ala Gly Arg Pro Gly Ser
185                 190                 195                 200 gag cac act gtg gaa ggc cac cgt ttc cct gcc gag atc cac gtg gtt     771
Glu His Thr Val Glu Gly His Arg Phe Pro Ala Glu Ile His Val Val
                205                 210                 215 cac ctc agc acc gcc ttt gcc aga gtt gac gag gcc ttg ggg cgc ccg     819
His Leu Ser Thr Ala Phe Ala Arg Val Asp Glu Ala Leu Gly Arg Pro
            220                 225                 230 gga ggc ctg gcc gtg ttg gcc gcc ttt ctg gag gag ggc ccg gaa gaa     867
Gly Gly Leu Ala Val Leu Ala Ala Phe Leu Glu Glu Gly Pro Glu Glu
        235                 240                 245 aac agt gcc tat gag cag ttg ctg tct cgc ttg gaa gaa atc gct gag     915
Asn Ser Ala Tyr Glu Gln Leu Leu Ser Arg Leu Glu Glu Ile Ala Glu
    250                 255                 260 gaa ggc tca gag act cag gtc cca gga ctg gac ata tct gca ctc ctg     963
Glu Gly Ser Glu Thr Gln Val Pro Gly Leu Asp Ile Ser Ala Leu Leu
265                 270                 275                 280 ccc tct gac ttc agc cgc tac ttc caa tat gag ggg tct ctg act aca    1011
Pro Ser Asp Phe Ser Arg Tyr Phe Gln Tyr Glu Gly Ser Leu Thr Thr
                285                 290                 295 ccg ccc tgt gcc cag ggt gtc atc tgg act gtg ttt aac cag aca gtg    1059
Pro Pro Cys Ala Gln Gly Val Ile Trp Thr Val Phe Asn Gln Thr Val
            300                 305                 310 atg ctg agt gct aag cag ctc cac acc ctc tct gac acc ctg tgg gga    1107
Met Leu Ser Ala Lys Gln Leu His Thr Leu Ser Asp Thr Leu Trp Gly
        315                 320                 325
```

```
cct ggt gac tct cgg cta cag ctg aac ttc cga gcg acg cag cct ttg     1155
Pro Gly Asp Ser Arg Leu Gln Leu Asn Phe Arg Ala Thr Gln Pro Leu
330                 335                 340 aat ggg cga gtg att gag gcc tcc ttc cct gct gga gtg gac agc agt     1203
Asn Gly Arg Val Ile Glu Ala Ser Phe Pro Ala Gly Val Asp Ser Ser
345                 350                 355                 360 cct cgg gct gct gag cca gtc cag ctg aat tcc tgc ctg gct gct ggt     1251
Pro Arg Ala Ala Glu Pro Val Gln Leu Asn Ser Cys Leu Ala Ala Gly
                365                 370                 375 gac atc cta gcc ctg gtt ttt ggc ctc ctt ttt gct gtc acc agc gtc     1299
Asp Ile Leu Ala Leu Val Phe Gly Leu Leu Phe Ala Val Thr Ser Val
            380                 385                 390 gcg ttc ctt gtg cag atg aga agg cag cac aga agg gga acc aaa ggg     1347
Ala Phe Leu Val Gln Met Arg Arg Gln His Arg Arg Gly Thr Lys Gly
        395                 400                 405 ggt gtg agc tac cgc cca gca gag gta gcc gag act gga gcc                 1389
Gly Val Ser Tyr Arg Pro Ala Glu Val Ala Glu Thr Gly Ala
410                 415                 420 tagaggctgg atcttggaga atgtgagaag ccagccagag gcatctgagg gggagccggt    1449
aactgtcctg tcctgctcat tatgccactt ccttttaact gccaagaaat ttttaaaat     1509 aaatatttat aat                                                      1522

<210> SEQ ID NO 2
<211> LENGTH: 459
<212> TYPE: PRT
<213> ORGANISM: HUMAN

<400> SEQUENCE: 2

Met Ala Pro Leu Cys Pro Ser Pro Trp Leu Pro Leu Leu Ile Pro Ala
        -35                 -30                 -25

Pro Ala Pro Gly Leu Thr Val Gln Leu Leu Leu Ser Leu Leu Leu Leu
    -20                 -15                 -10

Met Pro Val His Pro Gln Arg Leu Pro Arg Met Gln Glu Asp Ser Pro
 -5              -1   1                  5                  10

Leu Gly Gly Gly Ser Ser Gly Glu Asp Asp Pro Leu Gly Glu Glu Asp
                15                  20                  25

Leu Pro Ser Glu Glu Asp Ser Pro Arg Glu Glu Asp Pro Pro Gly Glu
        30                  35                  40

Glu Asp Leu Pro Gly Glu Glu Asp Leu Pro Gly Glu Glu Asp Leu Pro
    45                  50                  55

Glu Val Lys Pro Lys Ser Glu Glu Gly Ser Leu Lys Leu Glu Asp
60                  65                  70                  75

Leu Pro Thr Val Glu Ala Pro Gly Asp Pro Gln Glu Pro Gln Asn Asn
                80                  85                  90

Ala His Arg Asp Lys Glu Gly Asp Asp Gln Ser His Trp Arg Tyr Gly
            95                 100                 105

Gly Asp Pro Pro Trp Pro Arg Val Ser Pro Ala Cys Ala Gly Arg Phe
        110                 115                 120

Gln Ser Pro Val Asp Ile Arg Pro Gln Leu Ala Ala Phe Cys Pro Ala
    125                 130                 135

Leu Arg Pro Leu Glu Leu Leu Gly Phe Gln Leu Pro Pro Leu Pro Glu
140                 145                 150                 155

Leu Arg Leu Arg Asn Asn Gly His Ser Val Gln Leu Thr Leu Pro Pro
                160                 165                 170

Gly Leu Glu Met Ala Leu Gly Pro Gly Arg Glu Tyr Arg Ala Leu Gln
            175                 180                 185
```

```
Leu His Leu His Trp Gly Ala Ala Gly Arg Pro Gly Ser Glu His Thr
        190                 195                 200

Val Glu Gly His Arg Phe Pro Ala Glu Ile His Val His Leu Ser
205                 210                 215

Thr Ala Phe Ala Arg Val Asp Glu Ala Leu Gly Arg Pro Gly Leu
220                 225                 230                 235

Ala Val Leu Ala Ala Phe Leu Glu Glu Gly Pro Glu Glu Asn Ser Ala
            240                 245                 250

Tyr Glu Gln Leu Leu Ser Arg Leu Glu Glu Ile Ala Glu Glu Gly Ser
                255                 260                 265

Glu Thr Gln Val Pro Gly Leu Asp Ile Ser Ala Leu Leu Pro Ser Asp
            270                 275                 280

Phe Ser Arg Tyr Phe Gln Tyr Glu Gly Ser Leu Thr Thr Pro Pro Cys
285                 290                 295

Ala Gln Gly Val Ile Trp Thr Val Phe Asn Gln Thr Val Met Leu Ser
300                 305                 310                 315

Ala Lys Gln Leu His Thr Leu Ser Asp Thr Leu Trp Gly Pro Gly Asp
                320                 325                 330

Ser Arg Leu Gln Leu Asn Phe Arg Ala Thr Gln Pro Leu Asn Gly Arg
                335                 340                 345

Val Ile Glu Ala Ser Phe Pro Ala Gly Val Asp Ser Ser Pro Arg Ala
            350                 355                 360

Ala Glu Pro Val Gln Leu Asn Ser Cys Leu Ala Ala Gly Asp Ile Leu
365                 370                 375

Ala Leu Val Phe Gly Leu Leu Phe Ala Val Thr Ser Val Ala Phe Leu
380                 385                 390                 395

Val Gln Met Arg Arg Gln His Arg Arg Gly Thr Lys Gly Gly Val Ser
            400                 405                 410

Tyr Arg Pro Ala Glu Val Ala Glu Thr Gly Ala
                415                 420

<210> SEQ ID NO 3
<211> LENGTH: 29
<212> TYPE: DNA
<213> ORGANISM: HUMAN

<400> SEQUENCE: 3
cgcccagtgg gtcatcttcc ccagaagag                                        29

<210> SEQ ID NO 4
<211> LENGTH: 19
<212> TYPE: DNA
<213> ORGANISM: HUMAN

<400> SEQUENCE: 4
ggaatcctcc tgcatccgg                                                   19

<210> SEQ ID NO 5
<211> LENGTH: 10898
<212> TYPE: DNA
<213> ORGANISM: HUMAN
<220> FEATURE:
<221> NAME/KEY: gene
<222> LOCATION: (1)..(10898)
<223> OTHER INFORMATION: full-length MN genomic sequence
<220> FEATURE:
<221> NAME/KEY: unsure of base at position 1974
<222> LOCATION: (1974)
<223> OTHER INFORMATION: unsure of base at position 1974, which is in
      the 5' region flanking the transcription initiation site (3507)
      as determined by RNase protection assay.
```

```
<400> SEQUENCE: 5
ggatcctgtt gactcgtgac cttaccccca accctgtgct ctctgaaaca tgagctgtgt      60
ccactcaggg ttaaatggat taagggcggt gcaagatgtg ctttgttaaa cagatgcttg     120
aaggcagcat gctcgttaag agtcatcacc aatccctaat ctcaagtaat cagggacaca     180
aacactgcgg aaggccgcag ggtcctctgc ctaggaaaac cagagacctt tgttcacttg     240
tttatctgac cttccctcca ctattgtcca tgaccctgcc aaatcccct ctgtgagaaa      300 cacccaagaa ttatcaataa aaaataaat ttaaaaaaaa aatacaaaaa aaaaaaaaa       360 aaaaaaaaa gacttacgaa tagttattga taaatgaata gctattggta aagccaagta     420
aatgatcata ttcaaaacca gacggccatc atcacagctc aagtctacct gatttgatct     480
ctttatcatt gtcattcttt ggattcacta gattagtcat catcctcaaa attctccccc     540
aagttctaat tacgttccaa acatttaggg gttacatgaa gcttgaacct actaccttct     600
ttgcttttga gccatgagtt gtaggaatga tgagtttaca ccttacatgc tggggattaa     660
tttaaacttt acctctaagt cagttgggta gcctttggct tattttttgta gctaattttg     720 tagttaatgg atgcactgtg aatcttgcta tgatagtttt cctccacact ttgccactag     780
gggtaggtag gtactcagtt ttcagtaatt gcttacctaa gaccctaagc cctatttctc     840
ttgtactggc ctttatctgt aatatgggca tatttaatac aatataattt ttggagtttt     900
tttgtttgtt tgtttgtttg ttttttgag acggagtctt gcatctgtca tgcccaggct     960
ggagtagcag tggtgccatc tcggctcact gcaagctcca cctcccgagt tcacgccatt    1020
ttcctgcctc agcctcccga gtagctggga ctacaggcgc ccgccaccat gcccggctaa    1080 tttttttgtat ttttggtaga gacggggttt caccgtgtta gccagaatgg tctcgatctc    1140
ctgacttcgt gatccacccg cctcggcctc ccaaagttct gggattacag gtgtgagcca    1200
ccgcacctgg ccaattttt gagtcttta aagtaaaaat atgtcttgta agctggtaac     1260
tatggtacat ttccttttat taatgtggtg ctgacggtca tataggttct tttgagtttg    1320
gcatgcatat gctactttt gcagtccttt cattacattt ttctctcttc atttgaagag     1380
catgttatat cttttagctt cacttggctt aaaaggttct ctcattagcc taacacagtg    1440
tcattgttgg taccacttgg atcataagtg gaaaaacagt caagaaattg cacagtaata    1500
cttgtttgta agagggatga ttcaggtgaa tctgacacta agaaactccc ctacctgagg    1560
tctgagattc ctctgacatt gctgtatata ggcttttcct ttgacagcct gtgactgcgg    1620
actatttttc ttaagcaaga tatgctaaag ttttgtgagc cttttttccag agagaggtct    1680 catatctgca tcaagtgaga acatataatg tctgcatgtt tccatatttc aggaatgttt    1740
gcttgtgttt tatgctttta tatagacagg gaaacttgtt cctcagtgac ccaaaagagg    1800
tgggaattgt tattggatat catcattggc ccacgctttc tgaccttgga aacaattaag    1860
ggttcataat ctcaattctg tcagaattgg tacaagaaat agctgctatg tttcttgaca    1920
ttccacttgg taggaaataa gaatgtgaaa ctcttcagtt ggtgtgtgtc cctngttttt    1980
ttgcaatttc cttcttactg tgttaaaaaa agtatgatc ttgctctgag aggtgaggca     2040
ttcttaatca tgatctttaa agatcaataa tataatcctt tcaaggatta tgtctttatt    2100
ataataaaga taatttgtct ttaacagaat caataatata atcccttaaa ggattatatc    2160
tttgctgggc gcagtggctc acacctgtaa tcccagcact tgggtggcc aaggtggaag     2220 gatcaaattt gcctacttct atattatctt ctaaagcaga attcatctct cttccctcaa    2280
tatgatgata ttgacagggt ttgccctcac tcactagatt gtgagctcct gctcagggca    2340
```

```
ggtagcgttt tttgtttttg ttttttgtttt tcttttttga cagagggtct tgctctgtca    2400
cccaggccag agtgcaatgg tacagtctca gctcactgca gcctcaaccg cctcggctca    2460
aaccatcatc ccatttcagc ctcctgagta gctgggacta caggcacatg ccattacacc    2520
tggctaattt ttttgtattt ctagtagaga cagggtttgg ccatgttgcc cgggctggtc    2580
tcgaactcct ggactcaagc aatccaccca cctcagcctc ccaaaatgag gaccgtgtc    2640
ttattcattt ccatgtccct agtccatagc ccagtgctgg acctatggta gtactaaata    2700
aatatttgtt gaatgcaata gtaaatagca tttcagggag caagaactag attaacaaag    2760
gtggtaaaag gtttggagaa aaaaataata gtttaatttg gctagagtat gagggagagt    2820
agtaggagac aagatggaaa ggtctcttgg gcaaggtttt gaaggaagtt ggaagtcaga    2880
agtacacaat gtgcatatcg tggcaggcag tggggagcca atgaaggctt ttgagcagga    2940
gagtaatgtg ttgaaaaata aatataggtt aaacctatca gagcccctct gacacataca    3000
cttgcttttc attcaagctc aagtttgtct cccacatacc cattacttaa ctcaccctcg    3060
ggctccccta gcagcctgcc ctacctcttt acctgcttcc tggtggagtc agggatgtat    3120
acatgagctg cttccctct cagccagagg acatgggggg ccccagctcc cctgcctttc    3180
cccttctgtg cctggagctg gaagcaggc cagggttagc tgaggctggc tggcaagcag    3240
ctgggtggtg ccaggagag cctgcatagt gccaggtggt gccttgggtt ccaagctagt    3300
ccatggcccc gataaccttc tgcctgtgca cacacctgcc cctcactcca cccccatcct    3360
agctttggta tggggagag ggcacagggc cagacaaacc tgtgagactt tggctccatc    3420
tctgcaaaag ggcgctctgt gagtcagcct gctcccctcc aggcttgctc ctccccacc    3480
cagctctcgt ttccaatgca cgtacagccc gtacacaccg tgtgctggga cacccccacag    3540
tcagccgcat ggctcccctg tgcccagcc cctggctccc tctgttgatc ccggcccctg    3600
ctccaggcct cactgtgcaa ctgctgctgt cactgctgct tctggtgcct gtccatcccc    3660
agaggttgcc ccggatgcag gaggattccc ccttgggagg aggctcttct ggggaagatg    3720
acccactggg cgaggaggat ctgcccagtg aagaggattc acccagagag gaggatccac    3780
ccggagagga ggatctacct ggagaggagg atctacctgg agaggaggat ctacctgaag    3840
ttaagcctaa atcagaagaa gagggctccc tgaagttaga ggatctacct actgttgagg    3900
ctcctggaga tcctcaagaa ccccagaata atgcccacag ggacaaagaa ggtaagtggt    3960
catcaatctc caaatccagg ttccaggagg ttcatgactc ccctcccata ccccagccta    4020
ggctctgttc actcagggaa ggaggggaga ctgtactccc cacagaagcc cttccagagg    4080
tcccatacca atatccccat ccccactctc ggaggtagaa agggacagat gtggagagaa    4140
aataaaaagg gtgcaaaagg agagaggtga gctggatgag atgggagaga aggggaggc    4200
tggagaagag aaagggatga gaactgcaga tgagagaaaa aatgtgcaga cagaggaaaa    4260
aaataggtgg agaaggagag tcagagagtt tgaggggaag agaaaaggaa agcttgggag    4320
gtgaagtggg taccagagac aagcaagaag agctggtaga agtcatctca tcttaggcta    4380
caatgaggaa ttgagaccta ggaagaaggg acacagcagg tagagaaacg tggcttcttg    4440
actcccaagc caggaatttg gggaaagggg ttggagacca tacaaggcag agggatgagt    4500
ggggagaaga aagaagggag aaaggaaaga tggtgtactc actcatttgg gactcaggac    4560
tgaagtgccc actcactttt ttttttttt ttttgagac aaactttcac ttttgttgcc    4620
caggctggag tgcaatggcg cgatctcggc tcactgcaac ctccacctcc cgggttcaag    4680
tgattctcct gcctcagcct ctagccaagt agctgcgatt acaggcatgc gccaccacgc    4740
```

```
ccggctaatt tttgtatttt tagtagagac ggggtttcgc catgttggtc aggctggtct    4800
cgaactcctg atctcaggtg atccaaccac cctggcctcc caaagtgctg ggattatagg    4860
cgtgagccac agcgcctggc ctgaagcagc cactcacttt tacagaccct aagacaatga    4920
ttgcaagctg gtaggattgc tgtttggccc acccagctgc ggtgttgagt ttgggtgcgg    4980
tctcctgtgc tttgcacctg gcccgcttaa ggcatttgtt acccgtaatg ctcctgtaag    5040
gcatctgcgt ttgtgacatc gttttggtcg ccaggaaggg attggggctc taagcttgag    5100
cggttcatcc ttttcattta tacaggggat gaccagagtc attggcgcta tggaggtgag    5160
acacccaccc gctgcacaga cccaatctgg gaacccagct ctgtggatct ccctacagc     5220 cgtccctgaa cactggtccc gggcgtccca ccgccgccc accgtcccac ccctcacct      5280 tttctacccg ggttccctaa gttcctgacc taggcgtcag acttcctcac tatactctcc    5340
caccccaggc gacccgccct ggccccgggt gtcccagcc tgcgcgggcc gcttccagtc     5400
cccggtggat atccgcccc agctcgccgc cttctgcccg ccctgcgcc cctggaact       5460 cctgggcttc cagctcccgc cgctcccaga actgcgcctg cgcaacaatg ccacagtgg     5520 tgaggggtc tccccgccga cttgggga tggggcgggg cgcagggaag gaaccgtcg        5580 cgcagtgcct gcccggggt tgggctggcc ctaccgggcg gggccggctc acttgcctct    5640
ccctacgcag tgcaactgac cctgcctcct gggctagaga tggctctggg tcccgggcgg    5700
gagtaccggg ctctgcagct gcatctgcac tggggggctg caggtcgtcc gggctcggag    5760
cacactgtgg aaggccaccg tttccctgcc gaggtgagcg cggactggcc gagaaggggc    5820
aaaggagcgg ggcggacggg ggccagagac gtggccctct cctaccctcg tgtccttttc    5880
agatccacgt ggttcacctc agcaccgcct ttgccagagt tgacgaggcc ttggggcgcc    5940
cgggaggcct ggccgtgttg gccgcctttc tggaggtacc agatcctgga caccccctac    6000
tccccgcttt cccatcccat gctcctcccg gactctatcg tggagccaga daccccatcc    6060
cagcaagctc actcaggccc ctggctgaca aactcattca cgcactgttt gttcatttaa    6120
cacccactgt gaaccaggca ccagccccca acaaggattc tgaagctgta ggtccttgcc    6180
tctaaggagc ccacagccag tgggggaggc tgacatgaca gacacatagg aaggacatag    6240
taaagatggt ggtcacagag gaggtgacac ttaaagcctt cactggtaga aaagaaaagg    6300
aggtgttcat tgcagaggaa acagaatgtg caaagactca gaatatggcc tatttaggga    6360
atggctacat acaccatgat tagaggaggc ccagtaaagg gaagggatgg tgagatgcct    6420
gctaggttca ctcactcact tttatttatt tatttatttt tttgacagtc tctctgtcgc    6480
ccaggctgga gtgcagtggt gtgatcttgg gtcactgcaa cttccgcctc ccgggttcaa    6540
gggattctcc tgcctcagct tcctgagtag ctggggttac aggtgtgtgc caccatgccc    6600
agctaatttt ttttgtatt tttagtagac agggtttcac catgttggtc aggctggtct     6660
caaactcctg gcctcaagtg atccgcctga ctcagcctac caaagtgctg attacaagtg    6720
tgagccaccg tgcccagcca cactcactga ttctttaatg ccagccacac agcacaaagt    6780
tcagagaaat gcctccatca tagcatgtca atatgttcat actcttaggt tcatgatgtt    6840
cttaacatta ggttcataag caaaataaga aaaagaata ataataaaa gaagtggcat      6900 gtcaggacct cacctgaaaa gccaaacaca gaatcatgaa ggtgaatgca gaggtgacac    6960
caacacaaag gtgtatatat ggtttcctgt ggggagtatg tacggaggca gcagtgagtg    7020
agactgcaaa cgtcagaagg gcacgggtca ctgagagcct agtatcctag taaagtgggc    7080
tctctccctc tctctccagc ttgtcattga aaaccagtcc accaagcttg ttggttcgca    7140
```

```
cagcaagagt acatagagtt tgaaataata cataggattt taagagggag acactgtctc    7200
taaaaaaaaa aacaacagca acaacaaaaa gcaacaacca ttacaatttt atgttccctc    7260
agcattctca gagctgagga atgggagagg actatgggaa cccccttcat gttccggcct    7320
tcagccatgg ccctggatac atgcactcat ctgtcttaca atgtcattcc cccaggaggg    7380
cccggaagaa aacagtgcct atgagcagtt gctgtctcgc ttggaagaaa tcgctgagga    7440
aggtcagttt gttggtctgg ccactaatct ctgtggccta gttcataaag aatcacccct    7500
tggagcttca ggtctgaggc tggagatggg ctccctccag tgcaggaggg attgaagcat    7560
gagccagcgc tcatcttgat aataaccatg aagctgacag acacagttac ccgcaaacgg    7620
ctgcctacag attgaaaacc aagcaaaaac cgccgggcac ggtggctcac gcctgtaatc    7680
ccagcacttt gggaggccaa ggcaggtgga tcacgaggtc aagagatcaa gaccatcctg    7740
gccaacatgg tgaaacccca tctctactaa aaatacgaaa aaatagccag gcgtggtggc    7800
gggtgcctgt aatcccagct actcgggagg ctgaggcagg agaatggcat gaacccggga    7860
ggcagaagtt gcagtgagcc gagatcgtgc cactgcactc cagcctgggc aacagagcga    7920
gactcttgtc tcaaaaaaaa aaaaaaaaaa gaaaaccaag caaaaaccaa aatgagacaa    7980
aaaaaacaag accaaaaaat ggtgtttgga aattgtcaag gtcaagtctg gagagctaaa    8040
cttttttctga gaactgttta tctttaataa gcatcaaata ttttaacttt gtaaatactt    8100
ttgttggaaa tcgttctctt cttagtcact cttgggtcat tttaaatctc acttactcta    8160
ctagaccttt taggtttctg ctagactagg tagaactctg cctttgcatt tcttgtgtct    8220
gttttgtata gttatcaata ttcatattta tttacaagtt attcagatca tttttttctt    8280
tcttttttt tttttttttt tttttacat ctttagtaga gacagggttt caccatattg    8340
gccaggctgc tctcaaactc ctgaccttgt gatccaccag cctcggcctc ccaaagtgct    8400
gggattcatt ttttctttt aatttgctct gggcttaaac ttgtggccca gcactttatg    8460
atggtacaca gagttaagag tgtagactca gacggtctt cttcttctt tctcttcctt    8520
cctcccttcc ctcccacctt cccttctctc cttcctttct ttcttcctct cttgcttcct    8580
caggcctctt ccagttgctc caaagccctg tactttttt tgagttaacg tcttatggga    8640
agggcctgca cttagtgaag aagtggtctc agagttgagt taccttggct tctgggaggt    8700
gaaactgtat ccctataccc tgaagcttta agggggtgca atgtagatga accccaaca    8760
tagatcctct tcacaggctc agagactcag gtcccaggac tggacatatc tgcactcctg    8820
ccctctgact tcagccgcta cttccaatat gaggggtctc tgactacacc gccctgtgcc    8880
cagggtgtca tctggactgt gtttaaccag acagtgatgc tgagtgctaa gcaggtgggc    8940
ctggggtgtg tgtggacaca gtgggtgcgg gggaagagg atgtaagatg agatgagaaa    9000
caggagaaga aagaaatcaa ggctgggctc tgtggcttac gcctataatc ccaccacgtt    9060
gggaggctga ggtgggagaa tggtttgagc ccaggagttc aagacaaggc ggggcaacat    9120
agtgtgaccc catctctacc aaaaaaaccc aacaaaaacc aaaatagcc gggcatggtg    9180
gtatgcggcc tagtcccagc tactcaagga ggctgaggtg ggaagatcgc ttgattccag    9240
gagtttgaga ctgcagtgag ctatgatccc accactgcct accatcttta ggatacattt    9300
atttatttat aaaagaaatc aagaggctgg atggggaata caggagctgg agggtggagc    9360
cctgaggtgc tggttgtgag ctggcctggg accttgttt cctgtcatgc catgaaccca    9420
cccacactgt ccactgacct ccctagctcc acacctctc tgacaccctg tggggacctg    9480
gtgactctcg gctacagctg aacttccgag cgacgcagcc tttgaatggg cgagtgattg    9540
```

```
aggcctcctt ccctgctgga gtggacagca gtcctcgggc tgctgagcca ggtacagctt    9600
tgtctggttt cccccagcc agtagtccct tatcctccca tgtgtgtgcc agtgtctgtc     9660
attggtggtc acagcccgcc tctcacatct ccttttctc tccagtccag ctgaattcct     9720
gcctggctgc tggtgagtct gcccctcctc ttggtcctga tgccaggaga ctcctcagca    9780
ccattcagcc cagggctgc tcaggaccgc tctgctccc tctccttttc tgcagaacag      9840
accccaaccc caatattaga gaggcagatc atggtgggga ttcccccatt gtccccagag    9900
gctaattgat tagaatgaag cttgagaaat ctcccagcat ccctctcgca aaagaatccc    9960 ccccccttttt tttaaagata gggtctcact ctgtttgccc caggctgggg tgttgtggca  10020
cgatcatagc tcactgcagc ctcgaactcc taggctcagg caatcctttc accttagctt   10080
ctcaaagcac tgggactgta ggcatgagcc actgtgcctg gccccaaacg gcccttttac   10140
ttggctttta ggaagcaaaa acggtgctta tcttacccct tctcgtgtat ccaccctcat   10200
cccttggctg gcctcttctg gagactgagg cactatgggg ctgcctgaga actcggggca   10260
ggggtggtgg agtgcactga ggcaggtgtt gaggaactct gcagaccct cttccttccc    10320 aaagcagccc tctctgctct ccatcgcagg tgacatccta gccctggttt ttggcctcct   10380
ttttgctgtc accagcgtcg cgttccttgt gcagatgaga aggcagcaca ggtattacac    10440
tgaccctttc ttcaggcaca agcttccccc acccttgtgg agtcacttca tgcaaagcgc   10500
atgcaaatga gctgctcctg ggccagtttt ctgattagcc tttcctgttg tgtacacaca   10560 gaagggaac caaggggt gtgagctacc gcccagcaga ggtagccgag actggagcct      10620
agaggctgga tcttggagaa tgtgagaagc cagccagagg catctgaggg ggagccggta   10680
actgtcctgt cctgctcatt atgccacttc cttttaactg ccaagaaatt ttttaaaata   10740
aatatttata ataaaatatg tgttagtcac ctttgttccc caaatcagaa ggaggtattt   10800
gaatttccta ttactgttat tagcaccaat ttagtggtaa tgcatttatt ctattacagt   10860
tcggcctcct tccacacatc actccaatgt gttgctcc                            10898
```

```
<210> SEQ ID NO 6
<211> LENGTH: 37
<212> TYPE: PRT
<213> ORGANISM: HUMAN

<400> SEQUENCE: 6

Met Ala Pro Leu Cys Pro Ser Pro Trp Leu Pro Leu Leu Ile Pro Ala
1               5                   10                  15

Pro Ala Pro Gly Leu Thr Val Gln Leu Leu Leu Ser Leu Leu Leu Leu
            20                  25                  30

Met Pro Val His Pro
        35

<210> SEQ ID NO 7
<211> LENGTH: 25
<212> TYPE: DNA
<213> ORGANISM: HUMAN

<400> SEQUENCE: 7
tggggttctt gaggatctcc aggag                                          25

<210> SEQ ID NO 8
<211> LENGTH: 26
<212> TYPE: DNA
<213> ORGANISM: HUMAN
```

-continued

```
<400> SEQUENCE: 8
ctctaacttc agggagccct cttctt                                              26

<210> SEQ ID NO 9
<211> LENGTH: 48
<212> TYPE: DNA
<213> ORGANISM: HUMAN
<220> FEATURE:
<221> NAME/KEY: primer_bind
<222> LOCATION: (1)..(48)
<223> OTHER INFORMATION: anchor primer that anneals to the homopolymeric
      tail.
<220> FEATURE:
<221> NAME/KEY: inosine
<222> LOCATION: (36)..(37) (41)..(42) (46)..(47)
<223> OTHER INFORMATION: each of the modified_bases at positions (36),
      (37), (41), (42), (46) and (47) are inosine

<400> SEQUENCE: 9
cuacuacuac uaggccacgc gtcgactagt acgggaaggg aagggaag                      48

<210> SEQ ID NO 10
<211> LENGTH: 6
<212> TYPE: PRT
<213> ORGANISM: HUMAN

<400> SEQUENCE: 10

Glu Glu Asp Leu Pro Ser
 1               5

<210> SEQ ID NO 11
<211> LENGTH: 6
<212> TYPE: PRT
<213> ORGANISM: HUMAN

<400> SEQUENCE: 11

Gly Glu Asp Asp Pro Leu
 1               5

<210> SEQ ID NO 12
<211> LENGTH: 21
<212> TYPE: PRT
<213> ORGANISM: HUMAN

<400> SEQUENCE: 12

Asn Asn Ala His Arg Asp Lys Glu Gly Asp Asp Gln Ser His Trp Arg
 1               5                  10                  15

Tyr Gly Gly Asp Pro
                20

<210> SEQ ID NO 13
<211> LENGTH: 16
<212> TYPE: PRT
<213> ORGANISM: HUMAN

<400> SEQUENCE: 13

His Pro Gln Arg Leu Pro Arg Met Gln Glu Asp Ser Pro Leu Gly Gly
 1               5                  10                  15

<210> SEQ ID NO 14
<211> LENGTH: 24
<212> TYPE: PRT
<213> ORGANISM: HUMAN

<400> SEQUENCE: 14

Glu Glu Asp Ser Pro Arg Glu Glu Asp Pro Pro Gly Glu Glu Asp Leu
```

```
                1               5                  10                 15
Pro Gly Glu Glu Asp Leu Pro Gly
                20
```

<210> SEQ ID NO 15
<211> LENGTH: 13
<212> TYPE: PRT
<213> ORGANISM: HUMAN

<400> SEQUENCE: 15

```
Leu Glu Glu Gly Pro Glu Glu Asn Ser Ala Tyr Glu Gln
  1               5                  10
```

<210> SEQ ID NO 16
<211> LENGTH: 16
<212> TYPE: PRT
<213> ORGANISM: HUMAN

<400> SEQUENCE: 16

```
Met Arg Arg Gln His Arg Arg Gly Thr Lys Gly Gly Val Ser Tyr Arg
  1               5                  10                 15
```

<210> SEQ ID NO 17
<211> LENGTH: 45
<212> TYPE: DNA
<213> ORGANISM: HUMAN

<400> SEQUENCE: 17
gtcgctagct ccatgggtca tatgcagagg ttgccccgga tgcag           45

<210> SEQ ID NO 18
<211> LENGTH: 43
<212> TYPE: DNA
<213> ORGANISM: HUMAN

<400> SEQUENCE: 18
gaagatctct tactcgagca ttctccaaga tccagcctct agg             43

<210> SEQ ID NO 19
<211> LENGTH: 10
<212> TYPE: DNA
<213> ORGANISM: HUMAN

<400> SEQUENCE: 19
ctccatctct                                                  10

<210> SEQ ID NO 20
<211> LENGTH: 10
<212> TYPE: DNA
<213> ORGANISM: HUMAN

<400> SEQUENCE: 20
ccacccccat                                                  10

<210> SEQ ID NO 21
<211> LENGTH: 205
<212> TYPE: DNA
<213> ORGANISM: HUMAN

<400> SEQUENCE: 21
acctgcccct cactccaccc ccatcctagc tttggtatgg gggagagggc acagggccag    60
acaaacctgt gagactttgg ctccatctct gcaaagggc gctctgtgag tcagcctgct    120
cccctccagg cttgctcctc ccccacccag ctctcgtttc caatgcacgt acagcccgta    180

```
cacaccgtgt gctgggacac cccac                                              205

<210> SEQ ID NO 22
<211> LENGTH: 8
<212> TYPE: PRT
<213> ORGANISM: HUMAN

<400> SEQUENCE: 22

Leu Glu His His His His His His
 1               5

<210> SEQ ID NO 23
<211> LENGTH: 10
<212> TYPE: DNA
<213> ORGANISM: HUMAN
<220> FEATURE:
<221> NAME/KEY: misc_feature
<222> LOCATION: (1)..(10)

<400> SEQUENCE: 23 yyycayyyyy                                                                10

<210> SEQ ID NO 24
<211> LENGTH: 10
<212> TYPE: DNA
<213> ORGANISM: HUMAN
<300> PUBLICATION INFORMATION:
<301> AUTHORS: Locker and Buzard,
<303> JOURNAL: DNA Sequencing and Mapping
<304> VOLUME: 1
<306> PAGES: 3-11
<307> DATE: 1990

<400> SEQUENCE: 24
tgtgagactt                                                                10

<210> SEQ ID NO 25
<211> LENGTH: 4
<212> TYPE: PRT
<213> ORGANISM: HUMAN
<220> FEATURE:
<221> NAME/KEY: SITE
<222> LOCATION: (1)..(4)
<223> OTHER INFORMATION: sequence element defined by Suzuki, J. Mol.
      Biol., 207: 61-84 (1989) as motif frequently found in gene
      regulatory proteins.
<220> FEATURE:
<221> NAME/KEY: VARIANTS
<222> LOCATION: (3)..(4)
<223> OTHER INFORMATION: variants in sequence element defined by Suzuki,
      J. Mol. Biol., 207: 61-84 (1989) as motif frequently found in
      gene regulatory proteins.

<400> SEQUENCE: 25

Ser Pro Xaa Xaa
 1

<210> SEQ ID NO 26
<211> LENGTH: 4
<212> TYPE: PRT
<213> ORGANISM: HUMAN
<220> FEATURE:
<221> NAME/KEY: SITE
<222> LOCATION: (1)..(4)
<223> OTHER INFORMATION: sequence element defined by Suzuki, J. Mol.
      Biol., 207: 61-84 (1989) as a motif frequently found in gene
      regulatory proteins.
<220> FEATURE:
<221> NAME/KEY: VARIANTS
<222> LOCATION: (3)..(4)
```

<223> OTHER INFORMATION: variants in sequence element defined by Suzuki,
      J. Mol. Biol., 207: 61-84 (1989) as a motif frequently found in
      gene regulatory proteins.

<400> SEQUENCE: 26

Thr Pro Xaa Xaa
 1

<210> SEQ ID NO 27
<211> LENGTH: 540
<212> TYPE: DNA
<213> ORGANISM: HUMAN
<220> FEATURE:
<221> NAME/KEY: promoter
<222> LOCATION: (1)..(540)

<400> SEQUENCE: 27
cttgcttttc attcaagctc aagtttgtct cccacatacc cattacttaa ctcaccctcg      60
ggctccccta gcagcctgcc ctacctcttt acctgcttcc tggtggagtc agggatgtat    120
acatgagctg ctttccctct cagccagagg acatgggggg ccccagctcc cctgcctttc    180
cccttctgtg cctggagctg ggaagcaggc cagggttagc tgaggctggc tggcaagcag    240
ctgggtggtg ccagggagag cctgcatagt gccaggtggt gccttgggtt ccaagctagt    300
ccatggcccc gataaccttc tgcctgtgca cacacctgcc cctcactcca ccccatcct     360 agctttggta tgggggagag ggcacagggc cagacaaacc tgtgagactt tggctccatc    420
tctgcaaaag ggcgctctgt gagtcagcct gctcccctcc aggcttgctc ctcccccacc    480
cagctctcgt ttccaatgca cgtacagccc gtacacaccg tgtgctggga caccccacag    540

<210> SEQ ID NO 28
<211> LENGTH: 445
<212> TYPE: DNA
<213> ORGANISM: HUMAN
<220> FEATURE:
<221> NAME/KEY: exon
<222> LOCATION: (1)
<223> OTHER INFORMATION: 1st MN exon

<400> SEQUENCE: 28
gcccgtacac accgtgtgct gggacacccc acagtcagcc gcatggctcc cctgtgcccc      60 agccctggc tccctctgtt gatcccggcc cctgctccag gcctcactgt gcaactgctg     120
ctgtcactgc tgcttctggt gcctgtccat ccccagaggt tgccccggat gcaggaggat    180 tccccttgg gaggaggctc ttctggggaa gatgacccac tgggcgagga ggatctgccc     240
agtgaagagg attcacccag agaggaggat ccacccggag aggaggatct acctggagag    300
gaggatctac ctggagagga ggatctacct gaagttaagc ctaaatcaga agagagggc     360 tccctgaagt tagaggatct acctactgtt gaggctcctg gagatcctca agaacccccag    420 aataatgccc acaggacaa agaag                                           445

<210> SEQ ID NO 29
<211> LENGTH: 30
<212> TYPE: DNA
<213> ORGANISM: HUMAN
<220> FEATURE:
<221> NAME/KEY: exon
<222> LOCATION: (1)
<223> OTHER INFORMATION: 2nd MN exon

<400> SEQUENCE: 29
gggatgacca gagtcattgg cgctatggag                                       30

-continued

```
<210> SEQ ID NO 30
<211> LENGTH: 171
<212> TYPE: DNA
<213> ORGANISM: HUMAN
<220> FEATURE:
<221> NAME/KEY: exon
<222> LOCATION: (1)
<223> OTHER INFORMATION: 3rd MN exon

<400> SEQUENCE: 30
gcgacccgcc ctggccccgg gtgtccccag cctgcgcggg ccgcttccag tccccggtgg      60
atatccgccc ccagctcgcc gccttctgcc cggccctgcg ccccctggaa ctcctgggct     120
tccagctccc gccgctccca gaactgcgcc tgcgcaacaa tggccacagt g              171

<210> SEQ ID NO 31
<211> LENGTH: 143
<212> TYPE: DNA
<213> ORGANISM: HUMAN
<220> FEATURE:
<221> NAME/KEY: exon
<222> LOCATION: (1)
<223> OTHER INFORMATION: 4th MN exon

<400> SEQUENCE: 31
tgcaactgac cctgcctcct gggctagaga tggctctggg tcccgggcgg gagtaccggg      60
ctctgcagct gcatctgcac tgggggctg caggtcgtcc gggctcggag cacactgtgg     120
aaggccaccg tttccctgcc gag                                             143

<210> SEQ ID NO 32
<211> LENGTH: 93
<212> TYPE: DNA
<213> ORGANISM: HUMAN
<220> FEATURE:
<221> NAME/KEY: exon
<222> LOCATION: (1)
<223> OTHER INFORMATION: 5th MN exon

<400> SEQUENCE: 32
atccacgtgg ttcacctcag caccgccttt gccagagttg acgaggcctt ggggcgcccg      60
ggaggcctgg ccgtgttggc cgcctttctg gag                                  93

<210> SEQ ID NO 33
<211> LENGTH: 67
<212> TYPE: DNA
<213> ORGANISM: HUMAN
<220> FEATURE:
<221> NAME/KEY: exon
<222> LOCATION: (1)
<223> OTHER INFORMATION: 6th MN exon

<400> SEQUENCE: 33
gagggcccgg aagaaaacag tgcctatgag cagttgctgt ctcgcttgga agaaatcgct      60
gaggaag                                                               67

<210> SEQ ID NO 34
<211> LENGTH: 158
<212> TYPE: DNA
<213> ORGANISM: HUMAN
<220> FEATURE:
<221> NAME/KEY: exon
<222> LOCATION: (1)
<223> OTHER INFORMATION: 7th MN exon

<400> SEQUENCE: 34
```

-continued

```
gctcagagac tcaggtccca ggactggaca tatctgcact cctgccctct gacttcagcc    60
gctacttcca atatgagggg tctctgacta caccgccctg tgcccagggt gtcatctgga   120
ctgtgtttaa ccagacagtg atgctgagtg ctaagcag                            158
```

```
<210> SEQ ID NO 35
<211> LENGTH: 145
<212> TYPE: DNA
<213> ORGANISM: HUMAN
<220> FEATURE:
<221> NAME/KEY: exon
<222> LOCATION: (1)
<223> OTHER INFORMATION: 8th MN exon

<400> SEQUENCE: 35
ctccacaccc tctctgacac cctgtgggga cctggtgact ctcggctaca gctgaacttc    60
cgagcgacgc agcctttgaa tgggcgagtg attgaggcct ccttccctgc tggagtggac   120
agcagtcctc gggctgctga gccag                                         145
```

```
<210> SEQ ID NO 36
<211> LENGTH: 27
<212> TYPE: DNA
<213> ORGANISM: HUMAN
<220> FEATURE:
<221> NAME/KEY: exon
<222> LOCATION: (1)
<223> OTHER INFORMATION: 9th MN exon

<400> SEQUENCE: 36
tccagctgaa ttcctgcctg gctgctg                                        27
```

```
<210> SEQ ID NO 37
<211> LENGTH: 82
<212> TYPE: DNA
<213> ORGANISM: HUMAN
<220> FEATURE:
<221> NAME/KEY: exon
<222> LOCATION: (1)
<223> OTHER INFORMATION: 10th MN exon

<400> SEQUENCE: 37
gtgacatcct agccctggtt tttggcctcc tttttgctgt caccagcgtc gcgttccttg    60
tgcagatgag aaggcagcac ag                                             82
```

```
<210> SEQ ID NO 38
<211> LENGTH: 191
<212> TYPE: DNA
<213> ORGANISM: HUMAN
<220> FEATURE:
<221> NAME/KEY: exon
<222> LOCATION: (1)
<223> OTHER INFORMATION: 11th MN exon

<400> SEQUENCE: 38
aaggggaacc aaaggggggtg tgagctaccg cccagcagag gtagccgaga ctggagccta    60
gaggctggat cttggagaat gtgagaagcc agccagaggc atctgagggg gagccggtaa   120
ctgtcctgtc ctgctcatta tgccacttcc ttttaactgc caagaaattt tttaaaataa   180
atatttataa t                                                        191
```

```
<210> SEQ ID NO 39
<211> LENGTH: 1174
<212> TYPE: DNA
<213> ORGANISM: HUMAN
<220> FEATURE:
```

<221> NAME/KEY: intron
<222> LOCATION: (1)..(1174)
<223> OTHER INFORMATION: 1st MN intron

<400> SEQUENCE: 39

| | | | | | |
|---|---|---|---|---|---|
| gtaagtggtc | atcaatctcc | aaatccaggt | tccaggaggt | tcatgactcc | cctcccatac | 60 |
| cccagcctag | gctctgttca | ctcagggaag | gaggggagac | tgtactcccc | acagaagccc | 120 |
| ttccagaggt | cccataccaa | tatcccatc | cccactctcg | gaggtagaaa | gggacagatg | 180 |
| tggagagaaa | ataaaaaggg | tgcaaaagga | gagaggtgag | ctggatgaga | tgggagagaa | 240 |
| gggggaggct | ggagaagaga | aagggatgag | aactgcagat | gagagaaaaa | atgtgcagac | 300 |
| agaggaaaaa | aataggtgga | gaaggagagt | cagagagttt | gaggggaaga | gaaaaggaaa | 360 |
| gcttgggagg | tgaagtgggt | accagagaca | agcaagaaga | gctggtagaa | gtcatctcat | 420 |
| cttaggctac | aatgaggaat | tgagacctag | gaagaaggga | cacagcaggt | agagaaacgt | 480 |
| ggcttcttga | ctcccaagcc | aggaatttgg | ggaaagggggt | tggagaccat | acaaggcaga | 540 |
| gggatgagtg | gggagaagaa | agaagggaga | aggaaagat | ggtgtactca | ctcatttggg | 600 |
| actcaggact | gaagtgccca | ctcactttt | tttttttttt | ttttgagaca | aactttcact | 660 |
| tttgttgccc | aggctggagt | gcaatggcgc | gatctcggct | cactgcaacc | tccacctccc | 720 |
| gggttcaagt | gattctcctg | cctcagcctc | tagccaagta | gctgcgatta | caggcatgcg | 780 |
| ccaccacgcc | cggctaattt | ttgtatttt | agtagagacg | gggtttcgcc | atgttggtca | 840 |
| ggctggtctc | gaactcctga | tctcaggtga | tccaaccacc | ctggcctccc | aaagtgctgg | 900 |
| gattataggc | gtgagccaca | gcgcctggcc | tgaagcagcc | actcacttt | acagaccta | 960 |
| agacaatgat | tgcaagctgg | taggattgct | gtttggccca | cccagctgcg | gtgttgagtt | 1020 |
| tgggtgcggt | ctcctgtgct | ttgcacctgg | cccgcttaag | gcatttgtta | cccgtaatgc | 1080 |
| tcctgtaagg | catctgcgtt | tgtgacatcg | ttttggtcgc | caggaaggga | ttggggctct | 1140 |
| aagcttgagc | ggttcatcct | tttcatttat | acag | | | 1174 |

<210> SEQ ID NO 40
<211> LENGTH: 193
<212> TYPE: DNA
<213> ORGANISM: HUMAN
<220> FEATURE:
<221> NAME/KEY: intron
<222> LOCATION: (1)..(193)
<223> OTHER INFORMATION: 2nd MN intron

<400> SEQUENCE: 40

| | | | | | |
|---|---|---|---|---|---|
| gtgagacacc | cacccgctgc | acagacccaa | tctgggaacc | cagctctgtg | gatctcccct | 60 |
| acagccgtcc | ctgaacactg | gtcccggcg | tcccacccgc | cgccaccgt | cccaccccct | 120 |
| cacctttct | acccgggttc | cctaagttcc | tgacctaggc | gtcagacttc | ctcactatac | 180 |
| tctcccaccc | cag | | | | | 193 |

<210> SEQ ID NO 41
<211> LENGTH: 131
<212> TYPE: DNA
<213> ORGANISM: HUMAN
<220> FEATURE:
<221> NAME/KEY: intron
<222> LOCATION: (1)..(131)
<223> OTHER INFORMATION: 3rd MN intron

<400> SEQUENCE: 41

| | | | | | |
|---|---|---|---|---|---|
| gtgaggggt | ctccccgccg | agacttgggg | atggggcggg | gcgcagggaa | gggaaccgtc | 60 |

```
gcgcagtgcc tgcccggggg ttgggctggc cctaccgggc ggggccggct cacttgcctc    120
tccctacgca g                                                          131
```

```
<210> SEQ ID NO 42
<211> LENGTH: 89
<212> TYPE: DNA
<213> ORGANISM: HUMAN
<220> FEATURE:
<221> NAME/KEY: intron
<222> LOCATION: (1)..(89)
<223> OTHER INFORMATION: 4th MN intron

<400> SEQUENCE: 42
gtgagcgcgg actggccgag aaggggcaaa ggagcggggc ggacgggggc cagagacgtg     60
gccctctcct accctcgtgt ccttttcag                                       89
```

```
<210> SEQ ID NO 43
<211> LENGTH: 1400
<212> TYPE: DNA
<213> ORGANISM: HUMAN
<220> FEATURE:
<221> NAME/KEY: intron
<222> LOCATION: (1)..(1400)
<223> OTHER INFORMATION: 5th MN intron

<400> SEQUENCE: 43
gtaccagatc ctggacaccc cctactcccc gctttcccat cccatgctcc tcccggactc     60
tatcgtggag ccagagaccc catcccagca agctcactca ggcccctggc tgacaaactc    120
attcacgcac tgtttgttca tttaacaccc actgtgaacc aggcaccagc ccccaacaag    180
gattctgaag ctgtaggtcc ttgcctctaa ggagcccaca gccagtgggg gaggctgaca    240
tgacagacac ataggaagga catagtaaag atggtggtca cagaggaggt gacacttaaa    300
gccttcactg gtagaaaaga aaaggaggtg ttcattgcag aggaaacaga atgtgcaaag    360
actcagaata tggcctattt agggaatggc tacatacacc atgattagag gaggcccagt    420
aaagggaagg gatggtgaga tgcctgctag gttcactcac tcacttttat ttatttattt    480 attttttga cagtctctct gtcgcccagg ctggagtgca gtggtgtgat cttgggtcac    540
tgcaacttcc gcctcccggg ttcaagggat tctcctgcct cagcttcctg agtagctggg    600
gttacaggtg tgtgccacca tgcccagcta atttttttt gtattttag tagacagggt    660 ttcaccatgt tggtcaggct ggtctcaaac tcctggcctc aagtgatccg cctgactcag    720
cctaccaaag tgctgattac aagtgtgagc caccgtgccc agccacactc actgattctt    780
taatgccagc cacacagcac aaagttcaga gaatgcctc catcatagca tgtcaatatg    840
ttcatactct taggttcatg atgttcttaa cattaggttc ataagcaaaa taagaaaaaa    900
gaataataaa taaagaagt ggcatgtcag gacctcacct gaaaagccaa acacagaatc    960
atgaaggtga atgcagaggt gacaccaaca caaaggtgta tatatggttt cctgtgggga   1020
gtatgtacgg aggcagcagt gagtgagact gcaaacgtca gaagggcacg ggtcactgag   1080
agcctagtat cctagtaaag tgggctctct ccctctctct ccagcttgtc attgaaaacc   1140
agtccaccaa gcttgttggt tcgcacagca agagtacata gagtttgaaa taatacatag   1200
gattttaaga gggagacact gtctctaaaa aaaaaacaa cagcaacaac aaaaagcaac   1260
aaccattaca atttatgtt ccctcagcat tctcagagct gaggaatggg agaggactat   1320
gggaaccccc ttcatgttcc ggccttcagc catggccctg gatacatgca ctcatctgtc   1380
ttacaatgtc attcccccag                                                1400
```

<210> SEQ ID NO 44
<211> LENGTH: 1334
<212> TYPE: DNA
<213> ORGANISM: HUMAN
<220> FEATURE:
<221> NAME/KEY: intron
<222> LOCATION: (1)..(1334)
<223> OTHER INFORMATION: 6th MN intron

<400> SEQUENCE: 44

```
gtcagtttgt tggtctggcc actaatctct gtggcctagt tcataaagaa tcacccttg      60
gagcttcagg tctgaggctg gagatgggct ccctccagtg caggagggat tgaagcatga     120
gccagcgctc atcttgataa taaccatgaa gctgacagac acagttaccc gcaaacggct     180
gcctacagat tgaaaaccaa gcaaaaaccg ccgggcacgg tggctcacgc ctgtaatccc     240
agcactttgg gaggccaagg caggtggatc acgaggtcaa gagatcaaga ccatcctggc     300
caacatggtg aaaccccatc tctactaaaa atacgaaaaa atagccaggc gtggtggcgg     360
gtgcctgtaa tcccagctac tcgggaggct gaggcaggag aatggcatga acccgggagg     420
cagaagttgc agtgagccga gatcgtgcca ctgcactcca gcctgggcaa cagagcgaga     480
ctcttgtctc aaaaaaaaaa aaaaaaaga aaccaagca aaaccaaaa tgagacaaaa         540
aaaacaagac caaaaaatgg tgtttggaaa ttgtcaaggt caagtctgga gagctaaact     600
ttttctgaga actgtttatc tttaataagc atcaaatatt ttaactttgt aaatactttt     660
gttggaaatc gttctcttct tagtcactct tgggtcattt taaatctcac ttactctact     720
agacctttta ggtttctgct agactaggta gaactctgcc tttgcatttc ttgtgtctgt     780
tttgtatagt tatcaatatt catatttatt tacaagttat tcagatcatt ttttcttttc     840
tttttttttt tttttttttt ttttacatct ttagtagaga cagggtttca ccatattggc     900
caggctgctc tcaaaactcct gaccttgtga tccaccagcc tcggcctccc aaagtgctgg    960
gattcatttt ttcttttttaa tttgctctgg gcttaaactt gtggcccagc actttatgat   1020
ggtacacaga gttaagagtg tagactcaga cggtctttct tctttccttc tcttccttcc   1080
tcccttccct cccaccttcc cttctctcct tcctttcttt cttcctctct tgcttcctca   1140
ggcctcttcc agttgctcca aagccctgta cttttttttg agttaacgtc ttatgggaag   1200
ggcctgcact tagtgaagaa gtggtctcag agttgagtta ccttggcttc tgggaggtga   1260
aactgtatcc ctatacctg aagctttaag ggggtgcaat gtagatgaga ccccaacata    1320
gatcctcttc acag                                                       1334
```

<210> SEQ ID NO 45
<211> LENGTH: 512
<212> TYPE: DNA
<213> ORGANISM: HUMAN
<220> FEATURE:
<221> NAME/KEY: intron
<222> LOCATION: (1)..(512)
<223> OTHER INFORMATION: 7th MN intron

<400> SEQUENCE: 45

```
gtgggcctgg ggtgtgtgtg gacacagtgg gtgcggggga aagaggatgt aagatgagat      60
gagaaacagg agaagaaaga atcaaggct gggctctgtg gcttacgcct ataatcccac      120
cacgttggga ggctgaggtg ggagaatggt ttgagcccag gagttcaaga caaggcgggg    180
caacatagtg tgaccccatc tctaccaaaa aaacccaac aaaaccaaaa atagccgggc     240
atggtggtat gcggcctagt cccagctact caaggaggct gaggtgggaa gatcgcttga    300
```

```
ttccaggagt tgagactgc agtgagctat gatcccacca ctgcctacca tctttaggat      360
acatttattt atttataaaa gaaatcaaga ggctggatgg ggaatacagg agctggaggg      420
tggagccctg aggtgctggt tgtgagctgg cctgggaccc ttgtttcctg tcatgccatg      480
aacccaccca cactgtccac tgacctccct ag                                    512

<210> SEQ ID NO 46
<211> LENGTH: 114
<212> TYPE: DNA
<213> ORGANISM: HUMAN
<220> FEATURE:
<221> NAME/KEY: intron
<222> LOCATION: (1)..(114)
<223> OTHER INFORMATION: 8th MN intron

<400> SEQUENCE: 46
gtacagcttt gtctggtttc cccccagcca gtagtccctt atcctcccat gtgtgtgcca       60
gtgtctgtca ttggtggtca cagcccgcct ctcacatctc ctttttctct ccag            114

<210> SEQ ID NO 47
<211> LENGTH: 617
<212> TYPE: DNA
<213> ORGANISM: HUMAN
<220> FEATURE:
<221> NAME/KEY: intron
<222> LOCATION: (1)..(617)
<223> OTHER INFORMATION: 9th MN intron

<400> SEQUENCE: 47
gtgagtctgc ccctcctctt ggtcctgatg ccaggagact cctcagcacc attcagcccc       60
agggctgctc aggaccgcct ctgctccctc tccttttctg cagaacagac cccaacccca      120
atattagaga ggcagatcat ggtggggatt ccccccattgt ccccagaggc taattgatta     180
gaatgaagct tgagaaatct cccagcatcc ctctcgcaaa agaatccccc ccctttttt      240 taaagatagg gtctcactct gtttgcccca ggctggggtg ttgtggcacg atcatagctc     300
actgcagcct cgaactccta ggctcaggca atccttcac cttagcttct caaagcactg      360
ggactgtagg catgagccac tgtgcctggc cccaaacggc ccttttactt ggcttttagg     420
aagcaaaaac ggtgcttatc ttaccccttc tcgtgtatcc accctcatcc cttggctggc     480
ctcttctgga gactgaggca ctatggggct gcctgagaac tcggggcagg ggtggtggag     540
tgcactgagg caggtgttga ggaactctgc agacccctct tccttcccaa agcagccctc     600
tctgctctcc atcgcag                                                    617

<210> SEQ ID NO 48
<211> LENGTH: 130
<212> TYPE: DNA
<213> ORGANISM: HUMAN
<220> FEATURE:
<221> NAME/KEY: intron
<222> LOCATION: (1)..(130)
<223> OTHER INFORMATION: 10th MN intron

<400> SEQUENCE: 48
gtattacact gacccttct tcaggcacaa gcttccccca cccttgtgga gtcacttcat        60
gcaaagcgca tgcaaatgag ctgctcctgg gccagttttc tgattagcct ttcctgttgt      120
gtacacacag                                                             130

<210> SEQ ID NO 49
<211> LENGTH: 1401
<212> TYPE: DNA
```

```
<213> ORGANISM: HUMAN

<400> SEQUENCE: 49
caaactttca cttttgttgc ccaggctgga gtgcaatggc gcgatctcgg ctcactgcaa      60
cctccacctc ccgggttcaa gtgattctcc tgcctcagcc tctagccaag tagctgcgat     120
tacaggcatg cgccaccacg cccggctaat ttttgtattt ttagtagaga cggggtttcg     180
ccatgttggt caggctggtc tcgaactcct gatctcaggt gatccaacca ccctggcctc     240
ccaaagtgct gggattatag gcgtgagcca cagcgcctgg cctgaagcag ccactcactt     300
ttacagaccc taagacaatg attgcaagct ggtaggattg ctgtttggcc cacccagctg     360
cggtgttgag tttgggtgcg gtctcctgtg ctttgcacct ggcccgctta aggcatttgt     420
tacccgtaat gctcctgtaa ggcatctgcg tttgtgacat cgttttggtc gccaggaagg     480
gattggggct ctaagcttga gcggttcatc cttttcattt atacagggga tgaccagagt     540
cattggcgct atggaggtga gacacccacc cgctgcacag acccaatctg gaacccagc      600
tctgtggatc tcccctacag ccgtccctga acactggtcc cgggcgtccc acccgccgcc     660
caccgtccca cccctcacc ttttctaccc gggttccct a agttcctgac ctaggcgtca    720
gacttcctca ctatactctc ccaccccagg cgacccgccc tggccccggg tgtcccagc      780
ctgcgcgggc cgcttccagt ccccggtgga tatccgcccc cagctcgccg ccttctgccc     840
ggccctgcgc ccctggaac tcctgggctt ccagctcccg ccgctcccag aactgcgcct     900
gcgcaacaat ggccacagtg gtgagggggt ctccccgccg agacttgggg atggggcggg     960
gcgcagggaa gggaaccgtc gcgcagtgcc tgcccggggg ttgggctggc cctaccgggc    1020
ggggccggct cacttgcctc tccctacgca gtgcaactga ccctgcctcc tgggctagag    1080
atggctctgg gtcccgggcg ggagtaccgg gctctgcagc tgcatctgca ctgggggggct    1140
gcaggtcgtc cggctcgga gcacactgtg gaaggccacc gtttccctgc gaggtgagc     1200
gcggactggc cgagaagggg caaggagcg gggcggacgg gggccagaga cgtggccctc    1260
tcctaccctc gtgtcctttt cagatccacg tggttcacct cagcaccgcc tttgccagag    1320
ttgacgaggc cttgggcgc ccggggaggcc tggccgtgtt ggccgccttt ctggaggtac    1380
cagatcctgg acaccccta c                                              1401

<210> SEQ ID NO 50
<211> LENGTH: 59
<212> TYPE: PRT
<213> ORGANISM: HUMAN

<400> SEQUENCE: 50

Ser Ser Gly Glu Asp Asp Pro Leu Gly Glu Glu Asp Leu Pro Ser Glu
 1               5                  10                  15

Glu Asp Ser Pro Arg Glu Glu Asp Pro Pro Gly Glu Glu Asp Leu Pro
             20                  25                  30

Gly Glu Glu Asp Leu Pro Gly Glu Glu Asp Leu Pro Glu Val Lys Pro
         35                  40                  45

Lys Ser Glu Glu Glu Gly Ser Leu Lys Leu Glu
     50                  55

<210> SEQ ID NO 51
<211> LENGTH: 257
<212> TYPE: PRT
<213> ORGANISM: HUMAN

<400> SEQUENCE: 51
```

Gly Asp Asp Gln Ser His Trp Arg Tyr Gly Asp Pro Pro Trp Pro
1               5                   10                  15

Arg Val Ser Pro Ala Cys Ala Gly Arg Phe Gln Ser Pro Val Asp Ile
                20                  25                  30

Arg Pro Gln Leu Ala Ala Phe Cys Pro Ala Leu Arg Pro Leu Glu Leu
            35                  40                  45

Leu Gly Phe Gln Leu Pro Pro Leu Pro Glu Leu Arg Leu Arg Asn Asn
    50                  55                  60

Gly His Ser Val Gln Leu Thr Leu Pro Pro Gly Leu Glu Met Ala Leu
65                  70                  75                  80

Gly Pro Gly Arg Glu Tyr Arg Ala Leu Gln Leu His Leu His Trp Gly
                85                  90                  95

Ala Ala Gly Arg Pro Gly Ser Glu His Thr Val Glu Gly His Arg Phe
            100                 105                 110

Pro Ala Glu Ile His Val Val His Leu Ser Thr Ala Phe Ala Arg Val
            115                 120                 125

Asp Glu Ala Leu Gly Arg Pro Gly Gly Leu Ala Val Leu Ala Ala Phe
            130                 135                 140

Leu Glu Glu Gly Pro Glu Glu Asn Ser Ala Tyr Glu Gln Leu Leu Ser
145                 150                 155                 160

Arg Leu Glu Glu Ile Ala Glu Glu Gly Ser Glu Thr Gln Val Pro Gly
                165                 170                 175

Leu Asp Ile Ser Ala Leu Leu Pro Ser Asp Phe Ser Arg Tyr Phe Gln
            180                 185                 190

Tyr Glu Gly Ser Leu Thr Thr Pro Pro Cys Ala Gln Gly Val Ile Trp
            195                 200                 205

Thr Val Phe Asn Gln Thr Val Met Leu Ser Ala Lys Gln Leu His Thr
210                 215                 220

Leu Ser Asp Thr Leu Trp Gly Pro Gly Asp Ser Arg Leu Gln Leu Asn
225                 230                 235                 240

Phe Arg Ala Thr Gln Pro Leu Asn Gly Arg Val Ile Glu Ala Ser Phe
                245                 250                 255

Pro

<210> SEQ ID NO 52
<211> LENGTH: 20
<212> TYPE: PRT
<213> ORGANISM: HUMAN

<400> SEQUENCE: 52

Ile Leu Ala Leu Val Phe Gly Leu Leu Phe Ala Val Thr Ser Val Ala
1               5                   10                  15

Phe Leu Val Gln
            20

<210> SEQ ID NO 53
<211> LENGTH: 25
<212> TYPE: PRT
<213> ORGANISM: HUMAN

<400> SEQUENCE: 53

Met Arg Arg Gln His Arg Arg Gly Thr Lys Gly Gly Val Ser Tyr Arg
1               5                   10                  15

Pro Ala Glu Val Ala Glu Thr Gly Ala
            20                  25

<210> SEQ ID NO 54

```
<211> LENGTH: 59
<212> TYPE: PRT
<213> ORGANISM: HUMAN

<400> SEQUENCE: 54

Ser Ala Ser Glu Glu Pro Ser Pro Ser Glu Val Pro Phe Pro Ser Glu
  1               5                  10                  15

Glu Pro Ser Pro Ser Glu Glu Pro Phe Pro Ser Val Arg Pro Phe Pro
             20                  25                  30

Ser Val Val Leu Phe Pro Ser Glu Glu Pro Phe Pro Ser Lys Glu Pro
         35                  40                  45

Ser Pro Ser Glu Glu Pro Ser Ala Ser Glu Glu
     50                  55

<210> SEQ ID NO 55
<211> LENGTH: 470
<212> TYPE: RNA
<213> ORGANISM: HUMAN

<400> SEQUENCE: 55 cauggcccccg auaaccuucu gccugugcac acaccugccc cucacuccac ccccauccua    60
gcuuugguau gggggagagg gcacagggcc agacaaaccu gugagacuuu ggcuccaucu   120
cugcaaaagg gcgcucugug agucagccug cucccccucca ggcuugcucc uccccaccc   180 agcucucguu ccaaugcac guacagcccg uacacaccgu gugcugggac accccacagu   240
cagccgcaug gcucccccugu gcccagccc cuggcucccu cguugauccc ggcccccugc   300
uccaggccuc acugugcaac ugcugcuguc acugcugcuu cuggugccug uccauccccca   360 gagguugccc cggaugcagg aggauucccc cuugggagga ggcucuucug gggaagauga   420
cccacugggc gaggaggauc ugcccagug agaggauuca cccagagagg              470

<210> SEQ ID NO 56
<211> LENGTH: 292
<212> TYPE: DNA
<213> ORGANISM: HUMAN

<400> SEQUENCE: 56 gttttttttga gacggagtct tgcatctgtc atgcccaggc tggagtagca gtggtgccat    60
ctcggctcac tgcaagctcc acctcccgag ttcacgccat tttcctgcct cagcctcccg   120
agtagctggg actacaggcg cccgccacca tgcccggcta atttttttgta tttttggtag   180 agacggggtt tcaccgtgtt agccagaatg gtctcgatct cctgacttcg tgatccaccc   240
gcctcggcct cccaaagttc tgggattaca ggtgtgagcc accgcacctg gc            292

<210> SEQ ID NO 57
<211> LENGTH: 262
<212> TYPE: DNA
<213> ORGANISM: HUMAN

<400> SEQUENCE: 57
tttctttttt gagacagggt cttgctctgt cacccaggcc agagtgcaat ggtacagtct    60
cagctcactg cagcctcaac cgcctcggct caaaccatca tcccatttca gcctcctgag   120
tagctgggac tacaggcaca tgccattaca cctggctaat ttttttgtat ttctagtaga   180
gacagggttt ggccatgttg cccgggctgg tctcgaactc ctggactcaa gcaatccacc   240
cacctcagcc tcccaaaatg ag                                            262

<210> SEQ ID NO 58
```

```
<211> LENGTH: 2501
<212> TYPE: DNA
<213> ORGANISM: HUMAN
<220> FEATURE:
<221> NAME/KEY: misc_feature
<222> LOCATION: (1)..(2501)
<223> OTHER INFORMATION: region 5' to transcription initiation site as
      determined by RNase protection assay (nucleotide 3507 of Figures
      2A-2F and of SEQ ID NO: 5), corresponding to region of SEQ ID NO:
      5 and Figures 2A-2F from nucleotide (7) to nucleotide (2507), in
      which region some regulatory elements are probably situated.
<220> FEATURE:
<221> NAME/KEY: unsure what base is at position 1968
<222> LOCATION: (1968)
<223> OTHER INFORMATION: unsure of base at position 1968, which is the
      same unknown base as that at position 1974 of SEQ ID NO. 5, i.e.,
      the full-length MN genomic sequence, and of that unknown at
      position 1968 of SEQ ID NO: 90, and unknown at position 647 of SEQ
      ID NO: 110. That unknown base is in the 5' region flanking the
      transcription initiation site (3507) as determined by RNase
      protection assay.

<400> SEQUENCE: 58
tgttgactcg tgaccttacc cccaaccctg tgctctctga aacatgagct gtgtccactc      60
agggttaaat ggattaaggg cggtgcaaga tgtgctttgt taaacagatg cttgaaggca     120
gcatgctcgt taagagtcat caccaatccc taatctcaag taatcaggga cacaaacact     180
gcggaaggcc gcagggtcct ctgcctagga aaccagaga cctttgttca cttgtttatc      240
tgaccttccc tccactattg tccatgaccc tgccaaatcc ccctctgtga gaaacaccca     300
agaattatca ataaaaaaat aaatttaaaa aaaaaataca aaaaaaaaaa aaaaaaaaa      360 aaaagactta cgaatagtta ttgataaatg aatagctatt ggtaaagcca agtaaatgat     420
catattcaaa accagacggc catcatcaca gctcaagtct acctgatttg atctctttat     480
cattgtcatt ctttggattc actagattag tcatcatcct caaaattctc ccccaagttc     540
taattacgtt ccaaacattt aggggttaca tgaagcttga acctactacc ttctttgctt     600
ttgagccatg agttgtagga atgatgagtt tacaccttac atgctgggga ttaatttaaa     660
ctttacctct aagtcagttg ggtagccttt ggcttatttt tgtagctaat tttgtagtta     720
atggatgcac tgtgaatctt gctatgatag ttttcctcca cactttgcca ctaggggtag     780
gtaggtactc agttttcagt aattgcttac ctaagaccct aagccctatt tctcttgtac     840
tggcctttat ctgtaatatg ggcatattta atacaatata attttggag ttttttttgtt      900 tgtttgtttg tttgttttt tgagacggag tcttgcatct gtcatgccca ggctggagta     960
gcagtggtgc catctcggct cactgcaagc tccacctccc gagttcacgc cattttcctg    1020
cctcagcctc ccgagtagct gggactacag gcgcccgcca ccatgcccgg ctaattttt     1080 gtattttgg tagagacggg gtttcaccgt gttagccaga atggtctcga tctcctgact    1140
tcgtgatcca cccgcctcgg cctcccaaag ttctgggatt acaggtgtga gccaccgcac    1200
ctggccaatt ttttgagtct tttaaagtaa aaatatgtct tgtaagctgg taactatggt    1260
acatttcctt ttattaatgt ggtgctgacg gtcatatagg ttcttttgag tttggcatgc    1320
atatgctact ttttgcagtc ctttcattac attttttctct cttcatttga agagcatgtt   1380 atatcttta gcttcacttg gcttaaaagg ttctctcatt agcctaacac agtgtcattg    1440
ttggtaccac ttggatcata agtggaaaaa cagtcaagaa attgcacagt aatacttgtt    1500
tgtaagaggg atgattcagg tgaatctgac actaagaaac tcccctacct gaggtctgag    1560
attcctctga cattgctgta tataggcttt tcctttgaca gcctgtgact gcggactatt    1620
tttcttaagc aagatatgct aaagttttgt gagccttttt ccagagagag gtctcatatc    1680
```

```
tgcatcaagt gagaacatat aatgtctgca tgtttccata tttcaggaat gtttgcttgt   1740
gttttatgct tttatataga cagggaaact tgttcctcag tgacccaaaa gaggtgggaa   1800
ttgttattgg atatcatcat tggcccacgc tttctgacct tggaaacaat taagggttca   1860
taatctcaat tctgtcagaa ttggtacaag aaatagctgc tatgtttctt gacattccac   1920
ttggtaggaa ataagaatgt gaaactcttc agttggtgtg tgtccctngt ttttttgcaa   1980
tttccttctt actgtgttaa aaaaaagtat gatcttgctc tgagaggtga ggcattctta   2040
atcatgatct ttaaagatca ataatataat cctttcaagg attatgtctt tattataata   2100
aagataattt gtctttaaca gaatcaataa tataatccct taaaggatta tatctttgct   2160
gggcgcagtg gctcacacct gtaatcccag cactttgggt ggccaaggtg gaaggatcaa   2220
atttgcctac ttctatatta tcttctaaag cagaattcat ctctcttccc tcaatatgat   2280
gatattgaca gggtttgccc tcactcacta gattgtgagc tcctgctcag ggcaggtagc   2340
gttttttgtt tttgttttg ttttcttt tgagacagg gtcttgctct gtcacccagg   2400
ccagagtgca atggtacagt ctcagctcac tgcagcctca accgcctcgg ctcaaaccat   2460
catcccattt cagcctcctg agtagctggg actacaggca c                      2501

<210> SEQ ID NO 59
<211> LENGTH: 292
<212> TYPE: DNA
<213> ORGANISM: HUMAN
<220> FEATURE:
<221> NAME/KEY: misc_feature
<222> LOCATION: (1)

<400> SEQUENCE: 59 ttttttgag acggagtctt gcatctgtca tgcccaggct ggagtagcag tggtgccatc     60
tcggctcact gcaagctcca cctcccgagt tcacgccatt ttcctgcctc agcctcccga   120
gtagctggga ctacaggcgc ccgccaccat gcccggctaa tttttttgtat ttttggtaga  180 gacggggttt caccgtgtta gccagaatgg tctcgatctc ctgacttcgt gatccacccg   240
cctcggcctc ccaaagttct gggattacag gtgtgagcca ccgcacctgg cc           292

<210> SEQ ID NO 60
<211> LENGTH: 262
<212> TYPE: DNA
<213> ORGANISM: HUMAN

<400> SEQUENCE: 60 ttctttttg agacagggtc ttgctctgtc acccaggcca gagtgcaatg gtacagtctc     60
agctcactgc agcctcaacc gcctcggctc aaaccatcat cccatttcag cctcctgagt   120
agctgggact acaggcacat gccattacac ctggctaatt ttttgtatt tctagtagag    180 acagggtttg ccatgttgc ccgggctggt ctcgaactcc tggactcaag caatccaccc   240
acctcagcct cccaaaatga gg                                            262

<210> SEQ ID NO 61
<211> LENGTH: 294
<212> TYPE: DNA
<213> ORGANISM: HUMAN

<400> SEQUENCE: 61
tttttttttg agacaaactt tcacttttgt tgcccaggct ggagtgcaat ggcgcgatct    60
cggctcactg caacctccac ctcccgggtt caagtgattc tcctgcctca gcctctagcc   120
aagtagctgc gattacaggc atgcgccacc acgcccggct aatttttgta ttttagtag   180
```

```
agacggggtt tcgccatgtt ggtcaggctg gtctcgaact cctgatctca ggtgatccaa    240
ccaccctggc ctcccaaagt gctgggatta taggcgtgag ccacagcgcc tggc          294

<210> SEQ ID NO 62
<211> LENGTH: 276
<212> TYPE: DNA
<213> ORGANISM: HUMAN

<400> SEQUENCE: 62
tgacagtctc tctgtcgccc aggctggagt gcagtggtgt gatcttgggt cactgcaact     60
tccgcctccc gggttcaagg gattctcctg cctcagcttc ctgagtagct ggggttacag    120
gtgtgtgcca ccatgcccag ctaattttt tttgtatttt tagtagacag ggtttcacca    180
tgttggtcag gctggtctca aactcctggc ctcaagtgat ccgcctgact cagcctacca    240
aagtgctgat tacaagtgtg agccaccgtg cccagc                              276

<210> SEQ ID NO 63
<211> LENGTH: 289
<212> TYPE: DNA
<213> ORGANISM: HUMAN

<400> SEQUENCE: 63
cgccgggcac ggtggctcac gcctgtaatc ccagcacttt gggaggccaa ggcaggtgga     60
tcacgaggtc aagagatcaa gaccatcctg gccaacatgg tgaaacccca tctctactaa    120
aaatacgaaa aaatagccag gcgtggtggc gggtgcctgt aatcccagct actcgggagg    180
ctgaggcagg agaatggcat gaacccggga ggcagaagtt gcagtgagcc gagatcgtgc    240
cactgcactc cagcctgggc aacagagcga gactcttgtc tcaaaaaaa                289

<210> SEQ ID NO 64
<211> LENGTH: 298
<212> TYPE: DNA
<213> ORGANISM: HUMAN

<400> SEQUENCE: 64
aggctgggct ctgtggctta cgcctataat cccaccacgt tgggaggctg aggtgggaga     60
atggtttgag cccaggagtt caagacaagg cggggcaaca tagtgtgacc ccatctctac    120
caaaaaaacc ccaacaaaac caaaaatagc cgggcatggt ggtatgcggc ctagtcccag    180
ctactcaagg aggctgaggt gggaagatcg cttgattcca ggagtttgag actgcagtga    240
gctatgatcc caccactgcc taccatcttt aggatacatt tatttattta taaaagaa     298

<210> SEQ ID NO 65
<211> LENGTH: 105
<212> TYPE: DNA
<213> ORGANISM: HUMAN

<400> SEQUENCE: 65 tttttttacat ctttagtaga gacagggttt caccatattg gccaggctgc tctcaaactc     60
ctgaccttgt gatccaccag cctcggcctc ccaaagtgct gggat                   105

<210> SEQ ID NO 66
<211> LENGTH: 83
<212> TYPE: DNA
<213> ORGANISM: HUMAN

<400> SEQUENCE: 66
cctcgaactc ctaggctcag gcaatccttt cacccttagct tctcaaagca ctgggactgt    60
```

| | |
|---|---|
| aggcatgagc cactgtgcct ggc | 83 |

<210> SEQ ID NO 67
<211> LENGTH: 11
<212> TYPE: DNA
<213> ORGANISM: HUMAN

<400> SEQUENCE: 67

| | |
|---|---|
| agaaggtaag t | 11 |

<210> SEQ ID NO 68
<211> LENGTH: 11
<212> TYPE: DNA
<213> ORGANISM: HUMAN

<400> SEQUENCE: 68

| | |
|---|---|
| tggaggtgag a | 11 |

<210> SEQ ID NO 69
<211> LENGTH: 11
<212> TYPE: DNA
<213> ORGANISM: HUMAN

<400> SEQUENCE: 69

| | |
|---|---|
| cagtcgtgag g | 11 |

<210> SEQ ID NO 70
<211> LENGTH: 11
<212> TYPE: DNA
<213> ORGANISM: HUMAN

<400> SEQUENCE: 70

| | |
|---|---|
| ccgaggtgag c | 11 |

<210> SEQ ID NO 71
<211> LENGTH: 11
<212> TYPE: DNA
<213> ORGANISM: HUMAN

<400> SEQUENCE: 71

| | |
|---|---|
| tggaggtacc a | 11 |

<210> SEQ ID NO 72
<211> LENGTH: 11
<212> TYPE: DNA
<213> ORGANISM: HUMAN

<400> SEQUENCE: 72

| | |
|---|---|
| ggaaggtcag t | 11 |

<210> SEQ ID NO 73
<211> LENGTH: 11
<212> TYPE: DNA
<213> ORGANISM: HUMAN

<400> SEQUENCE: 73

| | |
|---|---|
| agcaggtggg c | 11 |

<210> SEQ ID NO 74
<211> LENGTH: 11
<212> TYPE: DNA
<213> ORGANISM: HUMAN

<400> SEQUENCE: 74
gccaggtaca g                                           11

<210> SEQ ID NO 75
<211> LENGTH: 11
<212> TYPE: DNA
<213> ORGANISM: HUMAN

<400> SEQUENCE: 75
tgctggtgag t                                           11

<210> SEQ ID NO 76
<211> LENGTH: 11
<212> TYPE: DNA
<213> ORGANISM: HUMAN

<400> SEQUENCE: 76
cacaggtatt a                                           11

<210> SEQ ID NO 77
<211> LENGTH: 11
<212> TYPE: DNA
<213> ORGANISM: HUMAN

<400> SEQUENCE: 77
atacagggga t                                           11

<210> SEQ ID NO 78
<211> LENGTH: 11
<212> TYPE: DNA
<213> ORGANISM: HUMAN

<400> SEQUENCE: 78
ccccaggcga c                                           11

<210> SEQ ID NO 79
<211> LENGTH: 11
<212> TYPE: DNA
<213> ORGANISM: HUMAN

<400> SEQUENCE: 79
acgcagtgca a                                           11

<210> SEQ ID NO 80
<211> LENGTH: 11
<212> TYPE: DNA
<213> ORGANISM: HUMAN

<400> SEQUENCE: 80
tttcagatcc a                                           11

<210> SEQ ID NO 81
<211> LENGTH: 11
<212> TYPE: DNA
<213> ORGANISM: HUMAN

<400> SEQUENCE: 81
ccccaggagg g                                           11

<210> SEQ ID NO 82
<211> LENGTH: 11
<212> TYPE: DNA
<213> ORGANISM: HUMAN

<400> SEQUENCE: 82

```
tcacaggctc a                                                          11
```

<210> SEQ ID NO 83
<211> LENGTH: 11
<212> TYPE: DNA
<213> ORGANISM: HUMAN

<400> SEQUENCE: 83

```
ccctagctcc a                                                          11
```

<210> SEQ ID NO 84
<211> LENGTH: 11
<212> TYPE: DNA
<213> ORGANISM: HUMAN

<400> SEQUENCE: 84

```
ctccagtcca g                                                          11
```

<210> SEQ ID NO 85
<211> LENGTH: 12
<212> TYPE: DNA
<213> ORGANISM: HUMAN

<400> SEQUENCE: 85

```
tcgcaggtga ca                                                         12
```

<210> SEQ ID NO 86
<211> LENGTH: 11
<212> TYPE: DNA
<213> ORGANISM: HUMAN

<400> SEQUENCE: 86

```
acacagaagg g                                                          11
```

<210> SEQ ID NO 87
<211> LENGTH: 377
<212> TYPE: PRT
<213> ORGANISM: HUMAN

<400> SEQUENCE: 87

```
Gln Arg Leu Pro Arg Met Gln Glu Asp Ser Pro Leu Gly Gly Ser
 1               5                  10                  15

Ser Gly Glu Asp Asp Pro Leu Gly Glu Glu Asp Leu Pro Ser Glu
                20                  25                  30

Asp Ser Pro Arg Glu Glu Asp Pro Pro Gly Glu Glu Asp Leu Pro Gly
                35                  40                  45

Glu Glu Asp Leu Pro Gly Glu Glu Asp Leu Pro Glu Val Lys Pro Lys
 50                  55                  60

Ser Glu Glu Glu Gly Ser Leu Lys Leu Glu Asp Leu Pro Thr Val Glu
 65                  70                  75                  80

Ala Pro Gly Asp Pro Gln Glu Pro Gln Asn Asn Ala His Arg Asp Lys
                85                  90                  95

Glu Gly Asp Asp Gln Ser His Trp Arg Tyr Gly Gly Asp Pro Pro Trp
                100                 105                 110

Pro Arg Val Ser Pro Ala Cys Ala Gly Arg Phe Gln Ser Pro Val Asp
                115                 120                 125

Ile Arg Pro Gln Leu Ala Ala Phe Cys Pro Ala Leu Arg Pro Leu Glu
                130                 135                 140

Leu Leu Gly Phe Gln Leu Pro Pro Leu Pro Glu Leu Arg Leu Arg Asn
145                 150                 155                 160
```

```
Asn Gly His Ser Val Gln Leu Thr Leu Pro Pro Gly Leu Glu Met Ala
            165                 170                 175

Leu Gly Pro Gly Arg Glu Tyr Arg Ala Leu Gln Leu His Leu His Trp
        180                 185                 190

Gly Ala Ala Gly Arg Pro Gly Ser Glu His Thr Val Glu Gly His Arg
        195                 200                 205

Phe Pro Ala Glu Ile His Val Val His Leu Ser Thr Ala Phe Ala Arg
        210                 215                 220

Val Asp Glu Ala Leu Gly Arg Pro Gly Gly Leu Ala Val Leu Ala Ala
225                 230                 235                 240

Phe Leu Glu Glu Gly Pro Glu Glu Asn Ser Ala Tyr Glu Gln Leu Leu
                245                 250                 255

Ser Arg Leu Glu Glu Ile Ala Glu Glu Gly Ser Glu Thr Gln Val Pro
        260                 265                 270

Gly Leu Asp Ile Ser Ala Leu Leu Pro Ser Asp Phe Ser Arg Tyr Phe
        275                 280                 285

Gln Tyr Glu Gly Ser Leu Thr Thr Pro Pro Cys Ala Gln Gly Val Ile
        290                 295                 300

Trp Thr Val Phe Asn Gln Thr Val Met Leu Ser Ala Lys Gln Leu His
305                 310                 315                 320

Thr Leu Ser Asp Thr Leu Trp Gly Pro Gly Asp Ser Arg Leu Gln Leu
                325                 330                 335

Asn Phe Arg Ala Thr Gln Pro Leu Asn Gly Arg Val Ile Glu Ala Ser
                340                 345                 350

Phe Pro Ala Gly Val Asp Ser Ser Pro Arg Ala Ala Glu Pro Val Gln
        355                 360                 365

Leu Asn Ser Cys Leu Ala Ala Gly Asp
        370                 375

<210> SEQ ID NO 88
<211> LENGTH: 34
<212> TYPE: DNA
<213> ORGANISM: HUMAN

<400> SEQUENCE: 88
tagacagatc tacgatggct cccctgtgcc ccag                              34

<210> SEQ ID NO 89
<211> LENGTH: 34
<212> TYPE: DNA
<213> ORGANISM: HUMAN

<400> SEQUENCE: 89
attcctctag acagttaccg gctcccccctc agat                             34

<210> SEQ ID NO 90
<211> LENGTH: 3532
<212> TYPE: DNA
<213> ORGANISM: HUMAN
<220> FEATURE:
<221> NAME/KEY: misc_feature which includes the MN gene promoter
<222> LOCATION: (1)..(3532)
<223> OTHER INFORMATION: region including the transcription initiation
      site (nucleotide 3507 of SEQ ID NO: 5 and of Figures 2A-2F) as
      determined by RNase protection assay, which region is inclusive of
      the MN gene promoter, and corresponds to nucleotide 7 to
      nucleotide 3538 of SEQ ID NO: 5 and of Figures 2A-2F.
<220> FEATURE:
<221> NAME/KEY: unsure what base is at position 1968
<222> LOCATION: (1968)
<223> OTHER INFORMATION: unsure of the base at position 1968, which is
``` the same unknown base at position 1974 of SEQ ID NO: 5 (the full-
length MN genomic sequence), position 1968 of SEQ ID NO: 58 and
position 647 of SEQ ID NO: 110. That unknown base is in the region
that includes the transcription initiation site (nucleotide 3507
of SEQ ID NO: 5 and of Figures 2A-2F) as determined by RNase
protection assay, which region is inclusive of the MN gene
promoter.

<400> SEQUENCE: 90

```
tgttgactcg tgaccttacc cccaaccctg tgctctctga aacatgagct gtgtccactc      60
agggttaaat ggattaaggg cggtgcaaga tgtgctttgt aaacagatg cttgaaggca     120
gcatgctcgt taagagtcat caccaatccc taatctcaag taatcaggga cacaaacact     180
gcggaaggcc gcagggtcct ctgcctagga aaccagaga cctttgttca cttgtttatc     240
tgaccttccc tccactattg tccatgaccc tgccaaatcc ccctctgtga gaaacaccca     300
agaattatca ataaaaaaat aaatttaaaa aaaaaataca aaaaaaaaa aaaaaaaaa      360
aaaagactta cgaatagtta ttgataaatg aatagctatt ggtaaagcca agtaaatgat     420
catattcaaa accagacggc catcatcaca gctcaagtct acctgatttg atctctttat     480
cattgtcatt ctttggattc actagattag tcatcatcct caaaattctc ccccaagttc     540
taattacgtt ccaaacattt aggggttaca tgaagcttga acctactacc ttctttgctt     600
ttgagccatg agttgtagga atgatgagtt tacaccttac atgctgggga ttaatttaaa     660
ctttacctct aagtcagttg ggtagccttt ggcttatttt tgtagctaat tttgtagtta     720
atggatgcac tgtgaatctt gctatgatag ttttcctcca cactttgcca ctaggggtag    780
gtaggtactc agttttcagt aattgcttac ctaagaccct aagccctatt tctcttgtac     840
tggcctttat ctgtaatatg ggcatattta atacaatata attttggag ttttttttgtt     900
tgtttgtttg tttgtttttt tgagacggag tcttgcatct gtcatgccca ggctggagta     960
gcagtggtgc catctcggct cactgcaagc tccacctccc gagttcacgc cattttcctg    1020
cctcagcctc ccgagtagct gggactacag gcgcccgcca ccatgcccgg ctaatttttt    1080
gtatttttgg tagagacggg gtttcaccgt gttagccaga atggtctcga tctcctgact    1140
tcgtgatcca cccgcctcgg cctcccaaag ttctgggatt acaggtgtga gccaccgcac    1200
ctggccaatt ttttgagtct tttaaagtaa aaatatgtct tgtaagctgg taactatggt    1260
acatttcctt ttattaatgt ggtgctgacg gtcatatagg ttcttttgag tttggcatgc    1320
atatgctact ttttgcagtc ctttcattac attttttctct cttcatttga agagcatgtt    1380
atatctttta gcttcacttg gcttaaaagg ttctctcatt agcctaacac agtgtcattg    1440
ttggtaccac ttggatcata agtggaaaaa cagtcaagaa attgcacagt aatacttgtt    1500
tgtaagaggg atgattcagg tgaatctgac actaagaaac tcccctacct gaggtctgag    1560
attcctctga cattgctgta tataggcttt tcctttgaca gcctgtgact gcggactatt    1620
tttcttaagc aagatatgct aaagttttgt gagccttttt ccagagagag gtctcatatc    1680
tgcatcaagt gagaacatat aatgtctgca tgtttccata tttcaggaat gtttgcttgt    1740
gttttatgct tttatataga cagggaaact tgttcctcag tgacccaaaa gaggtgggaa    1800
ttgttattgg atatcatcat tggcccacgc tttctgacct tggaaacaat taagggttca    1860
taatctcaat tctgtcagaa ttggtacaag aaatagctgc tatgtttctt gacattccac    1920
ttggtaggaa ataagaatgt gaaactcttc agttggtgtg tgtccctngt tttttttgcaa    1980
tttccttctt actgtgttaa aaaaagtat gatcttgctc tgagaggtga ggcattctta    2040
atcatgatct ttaaagatca ataatataat cctttcaagg attatgtctt tattataata    2100
```

```
aagataattt gtctttaaca gaatcaataa tataatccct taaaggatta tatctttgct    2160
gggcgcagtg gctcacacct gtaatcccag cactttgggt ggccaaggtg aaggatcaa    2220 atttgcctac ttctatatta tcttctaaag cagaattcat ctctcttccc tcaatatgat    2280
gatattgaca gggtttgccc tcactcacta gattgtgagc tcctgctcag ggcaggtagc    2340
gttttttgtt tttgttttttg tttttctttt ttgagacagg gtcttgctct gtcacccagg    2400
ccagagtgca atggtacagt ctcagctcac tgcagcctca accgcctcgg ctcaaaccat    2460
catcccattt cagcctcctg agtagctggg actacaggca catgccatta cacctggcta    2520 attttttttgt atttctagta gagacagggt ttggccatgt tgcccgggct ggtctcgaac    2580
tcctggactc aagcaatcca cccacctcag cctcccaaaa tgagggaccg tgtcttattc    2640
atttccatgt ccctagtcca tagcccagtg ctggacctat ggtagtacta aataaatatt    2700
tgttgaatgc aatagtaaat agcatttcag ggagcaagaa ctagattaac aaaggtggta    2760
aaaggtttgg agaaaaaaat aatagtttaa tttggctaga gtatgaggga gagtagtagg    2820
agacaagatg gaaaggtctc ttgggcaagg ttttgaagga agttggaagt cagaagtaca    2880
caatgtgcat atcgtggcag gcagtgggga gccaatgaag gcttttgagc aggagagtaa    2940
tgtgttgaaa aataaatata ggttaaacct atcagagccc ctctgacaca tacacttgct    3000
tttcattcaa gctcaagttt gtctcccaca tacccattac ttaactcacc ctcgggctcc    3060
cctagcagcc tgccctacct ctttacctgc ttcctggtgg agtcagggat gtatacatga    3120
gctgctttcc ctctcagcca gaggacatgg ggggccccag ctcccctgcc tttcccctc    3180 tgtgcctgga gctgggaagc aggccagggt tagctgaggc tggctggcaa gcagctgggt    3240
ggtgccaggg agagcctgca tagtgccagg tggtgccttg ggttccaagc tagtccatgg    3300
ccccgataac cttctgcctg tgcacacacc tgcccctcac tccacccca tcctagcttt    3360 ggtatggggg agagggcaca gggccagaca aacctgtgag actttggctc catctctgca    3420
aaagggcgct ctgtgagtca gcctgctccc ctccaggctt gctcctcccc cacccagctc    3480
tcgtttccaa tgcacgtaca gcccgtacac accgtgtgct gggacacccc ac    3532
```

<210> SEQ ID NO 91
<211> LENGTH: 204
<212> TYPE: DNA
<213> ORGANISM: HUMAN

<400> SEQUENCE: 91

```
cctgcccctc actccacccc catcctagct ttggtatggg ggagagggca gggccaga     60 caaacctgtg agactttggc tccatctctg caaaagggcg ctctgtgagt cagcctgctc    120
ccctccaggc ttgctcctcc cccacccagc tctcgtttcc aatgcacgta cagcccgtac    180
acaccgtgtg ctgggacacc ccac                                            204
```

<210> SEQ ID NO 92
<211> LENGTH: 132
<212> TYPE: DNA
<213> ORGANISM: HUMAN

<400> SEQUENCE: 92

```
ggatcctgtt gactcgtgac cttaccccca accctgtgct ctctgaaaca tgagctgtgt     60
ccactcaggg ttaaatggat taagggcggt gcaagatgtg cttttgttaaa cagatgcttg    120 aaggcagcat gc                                                          132
```

<210> SEQ ID NO 93

```
<211> LENGTH: 275
<212> TYPE: DNA
<213> ORGANISM: HUMAN

<400> SEQUENCE: 93
gcatagtgcc aggtggtgcc ttgggttcca agctagtcca tggccccgat aaccttctgc    60
ctgtgcacac acctgcccct cactccaccc ccatcctagc tttggtatgg gggagagggc   120
acagggccag acaaacctgt gagactttgg ctccatctct gcaaaagggc gctctgtgag   180
tcagcctgct cccctccagg cttgctcctc ccccacccag ctctcgtttc caatgcacgt   240
acagcccgta cacccgtgt gctgggacac cccac                              275

<210> SEQ ID NO 94
<211> LENGTH: 89
<212> TYPE: DNA
<213> ORGANISM: HUMAN

<400> SEQUENCE: 94
ctgctcccct ccaggcttgc tcctccccca cccagctctc gtttccaatg cacgtacagc    60
ccgtacacac cgtgtgctgg gacacccca                                      89

<210> SEQ ID NO 95
<211> LENGTH: 61
<212> TYPE: DNA
<213> ORGANISM: HUMAN

<400> SEQUENCE: 95
cacccagctc tcgtttccaa tgcacgtaca gcccgtacac accgtgtgct gggacacccc    60
a                                                                    61

<210> SEQ ID NO 96
<211> LENGTH: 116
<212> TYPE: DNA
<213> ORGANISM: HUMAN

<400> SEQUENCE: 96
acctgcccct cactccaccc ccatcctagc tttggtatgg gggagagggc acagggccag    60
acaaacctgt gagactttgg ctccatctct gcaaaagggc gctctgtgag tcagcc       116

<210> SEQ ID NO 97
<211> LENGTH: 36
<212> TYPE: PRT
<213> ORGANISM: HUMAN

<400> SEQUENCE: 97

Gly Glu Glu Asp Leu Pro Ser Glu Glu Asp Ser Pro Arg Glu Glu Asp
 1               5                  10                  15

Pro Pro Gly Glu Glu Asp Leu Pro Gly Glu Glu Asp Leu Pro Gly Glu
            20                  25                  30

Glu Asp Leu Pro
         35

<210> SEQ ID NO 98
<211> LENGTH: 6
<212> TYPE: PRT
<213> ORGANISM: HUMAN

<400> SEQUENCE: 98

Gly Glu Glu Asp Leu Pro
 1               5
```

```
<210> SEQ ID NO 99
<211> LENGTH: 4
<212> TYPE: PRT
<213> ORGANISM: HUMAN

<400> SEQUENCE: 99

Glu Glu Asp Leu
1

<210> SEQ ID NO 100
<211> LENGTH: 5
<212> TYPE: PRT
<213> ORGANISM: HUMAN

<400> SEQUENCE: 100

Glu Glu Asp Leu Pro
1               5

<210> SEQ ID NO 101
<211> LENGTH: 6
<212> TYPE: PRT
<213> ORGANISM: HUMAN

<400> SEQUENCE: 101

Glu Asp Leu Pro Ser Glu
1               5

<210> SEQ ID NO 102
<211> LENGTH: 7
<212> TYPE: PRT
<213> ORGANISM: HUMAN

<400> SEQUENCE: 102

Glu Glu Asp Leu Pro Ser Glu
1               5

<210> SEQ ID NO 103
<211> LENGTH: 6
<212> TYPE: PRT
<213> ORGANISM: HUMAN

<400> SEQUENCE: 103

Asp Leu Pro Gly Glu Glu
1               5

<210> SEQ ID NO 104
<211> LENGTH: 22
<212> TYPE: PRT
<213> ORGANISM: HUMAN

<400> SEQUENCE: 104

Gly Gly Ser Ser Gly Glu Asp Asp Pro Leu Gly Glu Glu Asp Leu Pro
1               5                   10                  15

Ser Glu Glu Asp Ser Pro
            20

<210> SEQ ID NO 105
<211> LENGTH: 25
<212> TYPE: PRT
<213> ORGANISM: HUMAN

<400> SEQUENCE: 105

Gly Glu Glu Asp Leu Pro Ser Glu Glu Asp Ser Pro Arg Glu Glu Asp
1               5                   10                  15
```

-continued

Pro Pro Gly Glu Glu Asp Leu Pro Gly
        20                  25

<210> SEQ ID NO 106
<211> LENGTH: 24
<212> TYPE: PRT
<213> ORGANISM: HUMAN

<400> SEQUENCE: 106

Glu Asp Pro Pro Gly Glu Glu Asp Leu Pro Gly Glu Glu Asp Leu Pro
1               5                   10                  15

Gly Glu Glu Asp Leu Pro Glu Val
            20

<210> SEQ ID NO 107
<211> LENGTH: 7
<212> TYPE: PRT
<213> ORGANISM: HUMAN

<400> SEQUENCE: 107

Gly Glu Thr Arg Ala Pro Leu
1               5

<210> SEQ ID NO 108
<211> LENGTH: 7
<212> TYPE: PRT
<213> ORGANISM: HUMAN

<400> SEQUENCE: 108

Gly Glu Thr Arg Glu Pro Leu
1               5

<210> SEQ ID NO 109
<211> LENGTH: 7
<212> TYPE: PRT
<213> ORGANISM: HUMAN

<400> SEQUENCE: 109

Gly Gln Thr Arg Ser Pro Leu
1               5

<210> SEQ ID NO 110
<211> LENGTH: 1247
<212> TYPE: DNA
<213> ORGANISM: HUMAN
<220> FEATURE:
<221> NAME/KEY: misc_feature
<222> LOCATION: (1)..(1247)
<223> OTHER INFORMATION: region 5' to the transcription initiation site
      as determined by RNase protection assay (nucleotide 3507 of SEQ ID
      NO: 5 and of Figures 2A-2F) in which an activating element is
      localized, which region corresponds to nucleotide 1328 to
      nucleotide 2574 of SEQ ID NO: 5 and of Figures 2A-2F.
<220> FEATURE:
<221> NAME/KEY: unsure what base is at position 647
<222> LOCATION: (647)
<223> OTHER INFORMATION: unsure of the base at position 647, which is
      the same unknown base as that at position 1974 of SEQ ID NO: 5,
      and as that at position 1968 of SEQ ID NOS: 58 and 90. That
      unknown base at position 647 is in a region in which an activating
      element is localized and is 5' to the transcription initiation
      site.

<400> SEQUENCE: 110
tatgctactt tttgcagtcc tttcattaca ttttctctc ttcatttgaa gagcatgtta      60
tatcttttag cttcacttgg cttaaaaggt tctctcatta gcctaacaca gtgtcattgt    120
tggtaccact tggatcataa gtggaaaaac agtcaagaaa ttgcacagta atacttgttt    180

```
gtaagaggga tgattcaggt gaatctgaca ctaagaaact cccctacctg aggtctgaga      240
ttcctctgac attgctgtat ataggctttt cctttgacag cctgtgactg cggactattt      300
ttcttaagca agatatgcta aagttttgtg agccttttc cagagagagg tctcatatct       360
gcatcaagtg agaacatata atgtctgcat gtttccatat ttcaggaatg tttgcttgtg      420
ttttatgctt ttatatagac agggaaactt gttcctcagt gacccaaaag aggtgggaat      480
tgttattgga tatcatcatt ggcccacgct ttctgacctt ggaaacaatt aagggttcat      540
aatctcaatt ctgtcagaat tggtacaaga aatagctgct atgtttcttg acattccact      600
tggtaggaaa taagaatgtg aaactcttca gttggtgtgt gtccctngtt tttttgcaat      660
ttccttctta ctgtgttaaa aaaagtatg atcttgctct gagaggtgag gcattcttaa       720
tcatgatctt taaagatcaa taatataatc ctttcaagga ttatgtcttt attataataa      780
agataatttg tctttaacag aatcaataat ataatccctt aaaggattat atctttgctg      840
ggcgcagtgg ctcacacctg taatcccagc actttgggtg gccaaggtgg aaggatcaaa     900
tttgcctact tctatattat cttctaaagc agaattcatc tctcttccct caatatgatg      960
atattgacag ggtttgccct cactcactag attgtgagct cctgctcagg gcaggtagcg     1020 tttttttgttt ttgttttgt ttttcttttt tgagacaggg tcttgctctg tcacccaggc     1080
cagagtgcaa tggtacagtc tcagctcact gcagcctcaa ccgcctcggc tcaaaccatc     1140
atcccatttc agcctcctga gtagctggga ctacaggcac atgccattac acctggctaa     1200 ttttttttgta tttctagtag agacagggtt tggccatgtt gcccggg                   1247
```

<210> SEQ ID NO 111
<211> LENGTH: 17
<212> TYPE: DNA
<213> ORGANISM: HUMAN

<400> SEQUENCE: 111

```
ctctgtgagt cagcctg                                                      17
```

<210> SEQ ID NO 112
<211> LENGTH: 23
<212> TYPE: DNA
<213> ORGANISM: HUMAN

<400> SEQUENCE: 112

```
aggcttgctc ctcccccacc cag                                               23
```

<210> SEQ ID NO 113
<211> LENGTH: 18
<212> TYPE: DNA
<213> ORGANISM: HUMAN

<400> SEQUENCE: 113

```
agactttggc tccatctc                                                     18
```

<210> SEQ ID NO 114
<211> LENGTH: 20
<212> TYPE: DNA
<213> ORGANISM: HUMAN

<400> SEQUENCE: 114

```
cactccaccc ccatcctagc                                                   20
```

<210> SEQ ID NO 115
<211> LENGTH: 26

```
<212> TYPE: DNA
<213> ORGANISM: HUMAN

<400> SEQUENCE: 115
gggagagggc acagggccag acaaac                                          26

<210> SEQ ID NO 116
<211> LENGTH: 15
<212> TYPE: PRT
<213> ORGANISM: HUMAN

<400> SEQUENCE: 116

Gly Gly Gly Gly Ser Gly Gly Gly Gly Ser Gly Gly Gly Gly Ser
1               5                   10                  15

<210> SEQ ID NO 117
<211> LENGTH: 34
<212> TYPE: DNA
<213> ORGANISM: HUMAN

<400> SEQUENCE: 117
cgtctagaag gaattcagct agactggctc agca                                 34

<210> SEQ ID NO 118
<211> LENGTH: 15
<212> TYPE: PRT
<213> ORGANISM: HUMAN

<400> SEQUENCE: 118

Glu Val Lys Pro Lys Ser Glu Glu Gly Ser Leu Lys Leu Glu
1               5                   10                  15

<210> SEQ ID NO 119
<211> LENGTH: 12
<212> TYPE: PRT
<213> ORGANISM: HUMAN

<400> SEQUENCE: 119

Gly Glu Glu Asp Leu Pro Gly Glu Glu Asp Leu Pro
1               5                   10

<210> SEQ ID NO 120
<211> LENGTH: 12
<212> TYPE: PRT
<213> ORGANISM: HUMAN

<400> SEQUENCE: 120

Glu Glu Asp Leu Pro Gly Glu Glu Asp Leu Pro Gly
1               5                   10

<210> SEQ ID NO 121
<211> LENGTH: 10
<212> TYPE: PRT
<213> ORGANISM: HUMAN

<400> SEQUENCE: 121

Glu Asp Leu Pro Gly Glu Glu Asp Leu Pro
1               5                   10

<210> SEQ ID NO 122
<211> LENGTH: 12
<212> TYPE: PRT
<213> ORGANISM: HUMAN

<400> SEQUENCE: 122
```

-continued

Asp Leu Pro Gly Glu Glu Asp Leu Pro Gly Glu Glu
1               5                   10

<210> SEQ ID NO 123
<211> LENGTH: 12
<212> TYPE: PRT
<213> ORGANISM: HUMAN

<400> SEQUENCE: 123

Leu Pro Gly Glu Glu Asp Leu Pro Gly Glu Glu Asp
1               5                   10

<210> SEQ ID NO 124
<211> LENGTH: 12
<212> TYPE: PRT
<213> ORGANISM: HUMAN

<400> SEQUENCE: 124

Pro Gly Glu Glu Asp Leu Pro Gly Glu Glu Asp Leu
1               5                   10

<210> SEQ ID NO 125
<211> LENGTH: 9
<212> TYPE: PRT
<213> ORGANISM: HUMAN

<400> SEQUENCE: 125

Ala Pro Gly Glu Glu Asp Leu Pro Ala
1               5

<210> SEQ ID NO 126
<211> LENGTH: 9
<212> TYPE: PRT
<213> ORGANISM: HUMAN

<400> SEQUENCE: 126

Ala Gly Glu Glu Asp Leu Pro Gly Ala
1               5

<210> SEQ ID NO 127
<211> LENGTH: 9
<212> TYPE: PRT
<213> ORGANISM: HUMAN

<400> SEQUENCE: 127

Ala Glu Glu Asp Leu Pro Gly Glu Ala
1               5

<210> SEQ ID NO 128
<211> LENGTH: 9
<212> TYPE: PRT
<213> ORGANISM: HUMAN

<400> SEQUENCE: 128

Ala Glu Asp Leu Pro Gly Glu Glu Ala
1               5

<210> SEQ ID NO 129
<211> LENGTH: 9
<212> TYPE: PRT
<213> ORGANISM: HUMAN

<400> SEQUENCE: 129

Ala Asp Leu Pro Gly Glu Glu Asp Ala
1               5

-continued

<210> SEQ ID NO 130
<211> LENGTH: 9
<212> TYPE: PRT
<213> ORGANISM: HUMAN

<400> SEQUENCE: 130

Ala Leu Pro Gly Glu Glu Asp Leu Ala
1               5

<210> SEQ ID NO 131
<211> LENGTH: 8
<212> TYPE: PRT
<213> ORGANISM: HUMAN

<400> SEQUENCE: 131

Ala Gly Glu Glu Asp Leu Pro Ala
1               5

<210> SEQ ID NO 132
<211> LENGTH: 8
<212> TYPE: PRT
<213> ORGANISM: HUMAN

<400> SEQUENCE: 132

Ala Glu Glu Asp Leu Pro Gly Ala
1               5

<210> SEQ ID NO 133
<211> LENGTH: 8
<212> TYPE: PRT
<213> ORGANISM: HUMAN

<400> SEQUENCE: 133

Ala Glu Asp Leu Pro Gly Glu Ala
1               5

<210> SEQ ID NO 134
<211> LENGTH: 8
<212> TYPE: PRT
<213> ORGANISM: HUMAN

<400> SEQUENCE: 134

Ala Asp Leu Pro Gly Glu Glu Ala
1               5

<210> SEQ ID NO 135
<211> LENGTH: 8
<212> TYPE: PRT
<213> ORGANISM: HUMAN

<400> SEQUENCE: 135

Ala Leu Pro Gly Glu Glu Asp Ala
1               5

<210> SEQ ID NO 136
<211> LENGTH: 8
<212> TYPE: PRT
<213> ORGANISM: HUMAN

<400> SEQUENCE: 136

Ala Pro Gly Glu Glu Asp Leu Ala
1               5

<210> SEQ ID NO 137
<211> LENGTH: 9

```
<212> TYPE: PRT
<213> ORGANISM: HUMAN

<400> SEQUENCE: 137

Ala Lys Lys Met Lys Arg Arg Lys Ala
 1               5

<210> SEQ ID NO 138
<211> LENGTH: 9
<212> TYPE: PRT
<213> ORGANISM: HUMAN

<400> SEQUENCE: 138

Ala Ile Thr Phe Asn Ala Gln Tyr Ala
 1               5

<210> SEQ ID NO 139
<211> LENGTH: 9
<212> TYPE: PRT
<213> ORGANISM: HUMAN

<400> SEQUENCE: 139

Ala Ser Ala Ser Ala Pro Val Ser Ala
 1               5

<210> SEQ ID NO 140
<211> LENGTH: 9
<212> TYPE: PRT
<213> ORGANISM: HUMAN

<400> SEQUENCE: 140

Ala Gly Gln Thr Arg Ser Pro Leu Ala
 1               5

<210> SEQ ID NO 141
<211> LENGTH: 6
<212> TYPE: PRT
<213> ORGANISM: HUMAN

<400> SEQUENCE: 141

Ser Glu Glu Asp Ser Pro
 1               5

<210> SEQ ID NO 142
<211> LENGTH: 6
<212> TYPE: PRT
<213> ORGANISM: HUMAN

<400> SEQUENCE: 142

Arg Glu Glu Asp Pro Pro
 1               5

<210> SEQ ID NO 143
<211> LENGTH: 12
<212> TYPE: DNA
<213> ORGANISM: HUMAN

<400> SEQUENCE: 143
agggcacagg gc                                                           12
```

The invention claimed is:

1. A polypeptide that binds specifically to a site on MN protein to which vertebrate cells adhere in a cell adhesion assay, wherein said polypeptide when tested in vitro inhibits the adhesion of cells to MN protein and competes for binding to MN's cell adhesion site with the M75 monoclonal antibody that is secreted from the hybridoma VU-M75, which was deposited at the American Type Culture Collection under ATCC No. HB 11128.

2. The polypeptide of claim 1 wherein said polypeptide, when in contact with a vertebrate preneoplastic or neoplastic cell that abnormally expresses MN protein, inhibits the growth of said cell.

3. The polypeptide of claim 1 wherein said polypeptide comprises an amino acid sequence selected from the group consisting of SEQ ID NOS: 137 and 138.

4. The polypeptide of claim 1 wherein said polypeptide consists of an amino acid sequence selected from the group consisting of SEQ ID NOS: 137 and 138.

5. The polypeptide of claim 1 wherein the site on the MN protein to which said vertebrate cells adhere in said cell adhesion assay is within the proteoglycan-like domain of the MN protein.

6. The polypeptide of claim 1 wherein the site on the MN protein to which said vertebrate cells adhere in said cell adhesion assay comprises an amino acid sequence selected from the group consisting of SEQ ID NOS: 10 and 97-106.

7. The polypeptide of claim 1 wherein the site on the MN protein to which said vertebrate cells adhere in said cell adhesion assay has an amino acid sequence selected from the group consisting of SEQ ID NOS: 10 and 97-106.

8. The polypeptide of claim 1 wherein said vertebrate cells are mammalian.

9. The polypeptide of claim 1 wherein said vertebrate cells are human.

* * * * *

UNITED STATES PATENT AND TRADEMARK OFFICE
CERTIFICATE OF CORRECTION

PATENT NO. : 7,910,691 B2
APPLICATION NO. : 11/929351
DATED : March 22, 2011
INVENTOR(S) : Jan Zavada et al.

Page 1 of 1

It is certified that error appears in the above-identified patent and that said Letters Patent is hereby corrected as shown below:

Cover Page, under "Related U.S. Application Data",
Item (63), "Continuation of application No. 09/807,949, filed as application No. PCT/US99/24879 on Oct. 22, 1999, now Pat No. 7,713,704." should read --Continuation of application No. 09/807,949, filed as application No. PCT/US99/24879 on Oct. 22, 1999, now Pat No. 7,713,704, which is a continuation-in-part of application No. 09/177,776, filed on Oct. 23, 1998, now Pat. No. 6,297,051 and a continuation-in-part of application No. 09/178,115, filed on Oct. 23, 1998, now Pat. No. 6,297,041.--

Signed and Sealed this
Nineteenth Day of July, 2011

David J. Kappos
*Director of the United States Patent and Trademark Office*